(12) United States Patent
Lopez et al.

(10) Patent No.: US 11,547,443 B2
(45) Date of Patent: Jan. 10, 2023

(54) METHOD AND APPARATUS FOR MINIMALLY INVASIVE INSERTION OF INTERVERTEBRAL IMPLANTS

(71) Applicant: DePuy Synthes Products, Inc., Raynham, MA (US)

(72) Inventors: Rudolf Morgenstern Lopez, Barcelona (ES); Robert Flower, Sun City, CA (US); Christopher Warren, Trabuco Canyon, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 377 days.

(21) Appl. No.: 16/913,171

(22) Filed: Jun. 26, 2020

(65) Prior Publication Data

US 2020/0323558 A1     Oct. 15, 2020

Related U.S. Application Data

(60) Continuation of application No. 15/835,534, filed on Dec. 8, 2017, now Pat. No. 10,736,661, which is a
(Continued)

(51) Int. Cl.
*A61B 17/58* (2006.01)
*A61B 17/60* (2006.01)
(Continued)

(52) U.S. Cl.
CPC ............ *A61B 17/3439* (2013.01); *A61B 5/24* (2021.01); *A61B 5/4893* (2013.01);
(Continued)

(58) Field of Classification Search
CPC combination set(s) only.
See application file for complete search history.

(56) References Cited

U.S. PATENT DOCUMENTS

| | | |
|---|---|---|
| 4,573,448 A | 3/1986 | Kambin |
| 4,625,725 A | 12/1986 | Davison et al. |

(Continued)

FOREIGN PATENT DOCUMENTS

| | | |
|---|---|---|
| CA | 2829160 A1 | 9/2012 |
| CN | 1984613 A | 6/2007 |

(Continued)

OTHER PUBLICATIONS

Alfen, et al., "Developments in the Area of Edoscopic Spine Surgery", European Musculoskeletal Review 2006, pp. 23-24, Thessys TM, Transforminal Endoscopic Spine System, Medical Solutions, ioimax Registered.

(Continued)

*Primary Examiner* — Sameh R Boles
(74) *Attorney, Agent, or Firm* — BakerHostetler

(57) ABSTRACT

A dilation introducer for orthopedic surgery is provided for minimally invasive access for insertion of an intervertebral implant. The dilation introducer may be used to provide an access position through Kambin's triangle from a posterolateral approach. A first dilator tube with a first longitudinal axis is provided. A second dilator tube may be introduced over the first, advanced along a second longitudinal axis parallel to but offset from the first. A third dilator tube may be introduced over the second, advanced along a third longitudinal axis parallel to but offset from both the first and the second. An access cannula may be introduced over the third dilator tube. With the first, second, and third dilator tubes removed, surgical instruments may pass through the access cannula to operate on an intervertebral disc and/or insert an intervertebral implant.

15 Claims, 57 Drawing Sheets

Related U.S. Application Data division of application No. 15/290,335, filed on Oct. 11, 2016, now Pat. No. 10,182,842, which is a continuation of application No. 14/454,418, filed on Aug. 7, 2014, now Pat. No. 9,486,149, which is a continuation of application No. 13/934,003, filed on Jul. 2, 2013, now Pat. No. 8,852,243, which is a continuation of application No. 13/416,889, filed on Mar. 9, 2012, now Pat. No. 8,518,087, which is a continuation-in-part of application No. 13/245,130, filed on Sep. 26, 2011, now Pat. No. 8,394,129.

(60) Provisional application No. 61/530,031, filed on Sep. 1, 2011, provisional application No. 61/504,120, filed on Jul. 1, 2011, provisional application No. 61/471,030, filed on Apr. 1, 2011, provisional application No. 61/451,379, filed on Mar. 10, 2011.

(51) Int. Cl.

| | | |
|---|---|---|
| *A61F 2/00* | (2006.01) | |
| *A61B 17/34* | (2006.01) | |
| *A61B 18/14* | (2006.01) | |
| *A61F 2/44* | (2006.01) | |
| *A61F 2/46* | (2006.01) | |
| *A61B 5/00* | (2006.01) | |
| *A61B 5/24* | (2021.01) | |
| *A61B 17/88* | (2006.01) | |
| *A61B 18/00* | (2006.01) | |
| *A61B 17/00* | (2006.01) | |
| *A61F 2/30* | (2006.01) | |

(52) U.S. Cl.
CPC ...... *A61B 17/3421* (2013.01); *A61B 17/3468* (2013.01); *A61B 17/885* (2013.01); *A61B 18/00* (2013.01); *A61B 18/1487* (2013.01); *A61F 2/442* (2013.01); *A61F 2/447* (2013.01); *A61F 2/4455* (2013.01); *A61F 2/4611* (2013.01); *A61B 2017/00261* (2013.01); *A61B 2017/00477* (2013.01); *A61B 2017/3445* (2013.01); *A61B 2018/00339* (2013.01); *A61B 2018/00601* (2013.01); *A61F 2/44* (2013.01); *A61F 2002/3021* (2013.01); *A61F 2002/3041* (2013.01); *A61F 2002/30207* (2013.01); *A61F 2002/30265* (2013.01); *A61F 2002/30266* (2013.01); *A61F 2002/30372* (2013.01); *A61F 2002/30373* (2013.01); *A61F 2002/30387* (2013.01); *A61F 2002/30405* (2013.01); *A61F 2002/30411* (2013.01); *A61F 2002/30482* (2013.01); *A61F 2002/30484* (2013.01); *A61F 2002/30517* (2013.01); *A61F 2002/30523* (2013.01); *A61F 2002/30528* (2013.01); *A61F 2002/30538* (2013.01); *A61F 2002/30556* (2013.01); *A61F 2002/30558* (2013.01); *A61F 2002/30561* (2013.01); *A61F 2002/30579* (2013.01); *A61F 2002/30593* (2013.01); *A61F 2002/30594* (2013.01); *A61F 2002/30601* (2013.01); *A61F 2002/30784* (2013.01); *A61F 2002/30841* (2013.01); *A61F 2002/30904* (2013.01); *A61F 2002/4627* (2013.01); *A61F 2310/00017* (2013.01); *A61F 2310/00023* (2013.01)

(56) References Cited

U.S. PATENT DOCUMENTS

| | | |
|---|---|---|
| 5,342,365 A | 8/1994 | Waldman |
| 5,387,215 A | 2/1995 | Fisher |
| 5,395,317 A | 3/1995 | Kambin |
| 5,484,437 A | 1/1996 | Michelson |
| 5,540,693 A | 7/1996 | Fisher |
| 5,554,191 A | 9/1996 | Lahille et al. |
| 5,575,176 A | 11/1996 | Rohrs et al. |
| 5,730,754 A | 3/1998 | Obenchain |
| 5,749,889 A | 5/1998 | Bacich et al. |
| 5,762,629 A | 6/1998 | Kambin |
| 5,810,776 A | 9/1998 | Bacich et al. |
| 5,865,847 A | 2/1999 | Kohrs et al. |
| 5,885,300 A | 3/1999 | Tokuhashi et al. |
| 5,954,635 A | 9/1999 | Foley et al. |
| 5,964,761 A | 10/1999 | Kambin |
| 5,968,098 A | 10/1999 | Winslow |
| 6,102,950 A | 8/2000 | Vaccaro |
| 6,175,758 B1 | 1/2001 | Kambin |
| 6,224,603 B1 | 5/2001 | Marino |
| 6,251,140 B1 | 6/2001 | Marino et al. |
| 6,290,724 B1 | 9/2001 | Marino |
| 6,368,325 B1 | 4/2002 | McKinley et al. |
| 6,395,007 B1 | 5/2002 | Bhatnagar et al. |
| 6,511,481 B2 | 1/2003 | Von et al. |
| 6,575,899 B1 | 6/2003 | Foley et al. |
| 6,575,979 B1 | 6/2003 | Cragg |
| 6,595,998 B2 | 7/2003 | Johnson et al. |
| 6,596,008 B1 | 7/2003 | Kambin |
| 6,648,915 B2 | 11/2003 | Sazy |
| 6,682,535 B2 | 1/2004 | Hoogland |
| 6,733,496 B2 | 5/2004 | Sharkey et al. |
| 6,740,090 B1 | 5/2004 | Cragg et al. |
| 6,764,491 B2 | 7/2004 | Frey et al. |
| 6,790,210 B1 | 9/2004 | Cragg et al. |
| 6,830,570 B1 | 12/2004 | Frey et al. |
| 6,843,804 B2 | 1/2005 | Bryan |
| 6,852,126 B2 | 2/2005 | Ahlgren |
| 6,887,243 B2 | 5/2005 | Culbert |
| 6,890,333 B2 | 5/2005 | Von et al. |
| 6,908,465 B2 | 6/2005 | Von et al. |
| 6,921,403 B2 | 7/2005 | Cragg et al. |
| 7,041,107 B2 | 5/2006 | Pohjonen et al. |
| 7,128,760 B2 | 10/2006 | Michelson |
| D536,096 S | 1/2007 | Hoogland et al. |
| 7,226,481 B2 | 6/2007 | Kuslich |
| 7,261,738 B2 | 8/2007 | Casey |
| 7,267,683 B2 | 9/2007 | Sharkey et al. |
| 7,282,061 B2 | 10/2007 | Sharkey et al. |
| 7,309,336 B2 | 12/2007 | Ashley et al. |
| 7,320,688 B2 | 1/2008 | Foley et al. |
| 7,361,140 B2 | 4/2008 | Ries et al. |
| 7,361,193 B2 | 4/2008 | Frey et al. |
| 7,400,930 B2 | 7/2008 | Sharkey et al. |
| 7,410,501 B2 | 8/2008 | Michelson |
| 7,445,636 B2 | 11/2008 | Michelson |
| D584,812 S | 1/2009 | Ries |
| 7,473,256 B2 | 1/2009 | Assell et al. |
| 7,481,812 B2 | 1/2009 | Frey et al. |
| 7,534,269 B2 | 5/2009 | Casey |
| 7,547,317 B2 | 6/2009 | Cragg |
| 7,556,651 B2 | 7/2009 | Humphreys et al. |
| 7,588,574 B2 | 9/2009 | Assell et al. |
| 7,641,657 B2 | 1/2010 | Cragg |
| 7,641,670 B2 | 1/2010 | Davison et al. |
| 7,647,123 B2 | 1/2010 | Sharkey et al. |
| 7,648,523 B2 | 1/2010 | Mirkovic et al. |
| 7,655,012 B2 | 2/2010 | Dipoto et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,690,381 B2 | 4/2010 | Bartish et al. |
| 7,691,057 B2 | 4/2010 | Miles et al. |
| 7,691,120 B2 | 4/2010 | Shluzas et al. |
| 7,717,944 B2 | 5/2010 | Foley et al. |
| 7,722,530 B2 | 5/2010 | Davison |
| 7,727,263 B2 | 6/2010 | Cragg |
| 7,740,633 B2 | 6/2010 | Assell et al. |
| 7,744,599 B2 | 6/2010 | Cragg |
| 7,763,025 B2 | 7/2010 | Ainsworth |
| 7,763,055 B2 | 7/2010 | Foley |
| 7,766,930 B2 | 8/2010 | Dipoto et al. |

(56) References Cited

U.S. PATENT DOCUMENTS

| | | |
|---|---|---|
| 7,771,479 B2 | 8/2010 | Humphreys et al. |
| 7,776,094 B2 | 8/2010 | McKinley et al. |
| 7,794,463 B2 | 9/2010 | Cragg |
| 7,799,032 B2 | 9/2010 | Assell et al. |
| 7,799,033 B2 | 9/2010 | Assell et al. |
| 7,799,034 B2 | 9/2010 | Johnson et al. |
| 7,799,036 B2 | 9/2010 | Davison et al. |
| 7,811,303 B2 | 10/2010 | Fallin et al. |
| 7,819,801 B2 | 10/2010 | Miles et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,837,734 B2 | 11/2010 | Zucherman et al. |
| 7,850,695 B2 | 12/2010 | Pagliuca et al. |
| 7,850,733 B2 | 12/2010 | Baynham et al. |
| 7,857,832 B2 | 12/2010 | Culbert et al. |
| 7,862,595 B2 | 1/2011 | Foley et al. |
| 7,867,259 B2 | 1/2011 | Foley et al. |
| 7,875,077 B2 | 1/2011 | Humphreys et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,931,689 B2 | 4/2011 | Hochschuler et al. |
| 7,938,832 B2 | 5/2011 | Culbert et al. |
| 7,972,382 B2 | 7/2011 | Foley et al. |
| 7,993,377 B2 | 8/2011 | Culbert et al. |
| 7,998,176 B2 | 8/2011 | Culbert |
| 8,062,375 B2 | 11/2011 | Glerum et al. |
| 8,105,382 B2 | 1/2012 | Olmos et al. |
| 8,109,977 B2 | 2/2012 | Culbert et al. |
| 8,133,232 B2 | 3/2012 | Levy et al. |
| 8,137,404 B2 | 3/2012 | Lopez et al. |
| 8,147,549 B2 | 4/2012 | Metcalf et al. |
| 8,157,845 B2 | 4/2012 | Warnick et al. |
| 8,216,316 B2 | 7/2012 | Kirschman |
| 8,252,060 B2 | 8/2012 | Hansell et al. |
| 8,262,736 B2 | 9/2012 | Michelson |
| 8,273,129 B2 | 9/2012 | Baynham et al. |
| 8,317,866 B2 | 11/2012 | Palmatier et al. |
| 8,366,777 B2 | 2/2013 | Matthis et al. |
| 8,394,129 B2 | 3/2013 | Morgenstern et al. |
| 8,398,713 B2 | 3/2013 | Weiman |
| 8,518,087 B2 | 8/2013 | Lopez et al. |
| 8,551,092 B2 | 10/2013 | Morgan et al. |
| 8,568,481 B2 | 10/2013 | Olmos et al. |
| 8,574,301 B2 | 11/2013 | Curran et al. |
| 8,597,333 B2 | 12/2013 | Morgenstern et al. |
| 8,623,021 B2 | 1/2014 | Ries et al. |
| 8,679,183 B2 | 3/2014 | Glerum et al. |
| 8,685,098 B2 | 4/2014 | Glerum et al. |
| 8,685,103 B2 | 4/2014 | Hansell et al. |
| 8,690,921 B2 | 4/2014 | Dwyer et al. |
| 8,709,088 B2 | 4/2014 | Kleiner et al. |
| 8,728,123 B2 | 5/2014 | Bucci et al. |
| 8,734,458 B2 | 5/2014 | O'Halloran et al. |
| 8,747,475 B2 | 6/2014 | Kuslich |
| 8,758,440 B2 | 6/2014 | Seifert et al. |
| 8,771,277 B2 | 7/2014 | Zappacosta et al. |
| 8,821,378 B2 | 9/2014 | Morgenstern et al. |
| 8,845,731 B2 | 9/2014 | Weiman |
| 8,845,732 B2 | 9/2014 | Weiman |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,858,598 B2 | 10/2014 | Seifert et al. |
| 8,864,773 B2 | 10/2014 | Paul et al. |
| 8,864,833 B2 | 10/2014 | Glerum et al. |
| 8,870,880 B2 | 10/2014 | Himmelberger et al. |
| 8,870,957 B2 | 10/2014 | Vraney et al. |
| 8,888,853 B2 | 11/2014 | Glerum et al. |
| 8,888,854 B2 | 11/2014 | Glerum et al. |
| 8,906,069 B2 | 12/2014 | Hansell et al. |
| 8,906,094 B2 | 12/2014 | Roche et al. |
| 8,936,626 B1 | 1/2015 | Tohmeh et al. |
| 8,940,048 B2 | 1/2015 | Butler et al. |
| 8,956,361 B2 | 2/2015 | Davenport et al. |
| 8,961,606 B2 | 2/2015 | Laskowitz et al. |
| 8,998,952 B2 | 4/2015 | Fauth et al. |
| 8,998,964 B2 | 4/2015 | Robinson |
| 8,998,991 B2 | 4/2015 | Bennett et al. |
| 9,011,493 B2 | 4/2015 | Zappacosta et al. |
| 9,017,410 B2 | 4/2015 | Hansell et al. |
| 9,034,041 B2 | 5/2015 | Wolters et al. |
| 9,034,045 B2 | 5/2015 | Davenport et al. |
| 9,039,769 B2 | 5/2015 | O'Halloran et al. |
| 9,039,771 B2 | 5/2015 | Glerum et al. |
| 9,044,276 B2 | 6/2015 | Pagano |
| 9,044,342 B2 | 6/2015 | Perloff et al. |
| 9,277,928 B2 | 3/2016 | Morgenstern Lopez |
| 9,387,313 B2 | 7/2016 | Culbert et al. |
| 9,486,149 B2 | 11/2016 | Morgenstern et al. |
| 2002/0091387 A1 | 7/2002 | Hoogland |
| 2002/0147485 A1 | 10/2002 | Mamo et al. |
| 2003/0028251 A1 | 2/2003 | Mathews |
| 2004/0059339 A1 | 3/2004 | Roehm et al. |
| 2004/0106999 A1 | 6/2004 | Mathews |
| 2004/0133280 A1 | 7/2004 | Trieu |
| 2004/0266257 A1 | 12/2004 | Ries et al. |
| 2005/0021031 A1 | 1/2005 | Foley et al. |
| 2005/0080443 A1 | 4/2005 | Fallin et al. |
| 2005/0090443 A1 | 4/2005 | Michael John |
| 2005/0090899 A1 | 4/2005 | Dipoto |
| 2005/0118550 A1 | 6/2005 | Turri |
| 2005/0154467 A1 | 7/2005 | Peterman et al. |
| 2005/0171608 A1 | 8/2005 | Peterman et al. |
| 2005/0171610 A1 | 8/2005 | Humphreys et al. |
| 2005/0222681 A1 | 10/2005 | Richley et al. |
| 2005/0256525 A1 | 11/2005 | Culbert et al. |
| 2006/0004398 A1 | 1/2006 | Binder et al. |
| 2006/0030756 A1 | 2/2006 | Usher et al. |
| 2006/0036241 A1 | 2/2006 | Siegal |
| 2006/0094976 A1 | 5/2006 | Bleich |
| 2006/0111714 A1 | 5/2006 | Foley |
| 2006/0129244 A1 | 6/2006 | Ensign |
| 2006/0142776 A1 | 6/2006 | Iwanari |
| 2006/0178745 A1 | 8/2006 | Bartish et al. |
| 2006/0178746 A1 | 8/2006 | Bartish et al. |
| 2006/0247778 A1 | 11/2006 | Ferree et al. |
| 2007/0093841 A1 | 4/2007 | Hoogland |
| 2007/0123891 A1 | 5/2007 | Ries et al. |
| 2007/0123892 A1 | 5/2007 | Ries et al. |
| 2007/0185491 A1 | 8/2007 | Foley et al. |
| 2007/0233244 A1 | 10/2007 | Lopez et al. |
| 2007/0233253 A1 | 10/2007 | Bray et al. |
| 2007/0255281 A1 | 11/2007 | Simonton et al. |
| 2007/0260318 A1 | 11/2007 | Lawson |
| 2007/0282449 A1 | 12/2007 | De et al. |
| 2008/0015699 A1 | 1/2008 | Voydeville |
| 2008/0015703 A1 | 1/2008 | Casey |
| 2008/0039842 A1 | 2/2008 | Sweeney |
| 2008/0058598 A1 | 3/2008 | Ries et al. |
| 2008/0077148 A1 | 3/2008 | Ries et al. |
| 2008/0125864 A1 | 5/2008 | De et al. |
| 2008/0140207 A1 | 6/2008 | Olmos et al. |
| 2008/0300685 A1 | 12/2008 | Carls et al. |
| 2008/0306481 A1 | 12/2008 | Farr et al. |
| 2009/0062807 A1 | 3/2009 | Song |
| 2009/0093885 A1 | 4/2009 | Levieux et al. |
| 2009/0149857 A1 | 6/2009 | Culbert et al. |
| 2009/0182429 A1 | 7/2009 | Humphreys et al. |
| 2009/0187246 A1 | 7/2009 | Foley |
| 2009/0216196 A1 | 8/2009 | Drontle et al. |
| 2009/0240335 A1 | 9/2009 | Arcenio et al. |
| 2009/0275890 A1 | 11/2009 | Leibowitz et al. |
| 2009/0292361 A1 | 11/2009 | Lopez |
| 2010/0040332 A1 | 2/2010 | Van et al. |
| 2010/0082109 A1 | 4/2010 | Greenhalgh et al. |
| 2010/0114147 A1 | 5/2010 | Biyani |
| 2010/0191336 A1 | 7/2010 | Greenhalgh |
| 2010/0211176 A1 | 8/2010 | Greenhalgh |
| 2010/0241160 A1 | 9/2010 | Murphy |
| 2010/0268231 A1 | 10/2010 | Kuslich et al. |

(56) References Cited

U.S. PATENT DOCUMENTS

| | | |
|---|---|---|
| 2010/0268341 A1 | 10/2010 | Dvorak et al. |
| 2010/0286787 A1 | 11/2010 | Villiers et al. |
| 2010/0292700 A1 | 11/2010 | Ries |
| 2010/0298938 A1 | 11/2010 | Humphreys et al. |
| 2010/0318134 A1 | 12/2010 | Roche et al. |
| 2010/0331891 A1 | 12/2010 | Culbert et al. |
| 2011/0040332 A1 | 2/2011 | Culbert et al. |
| 2011/0054538 A1 | 3/2011 | Zehavi et al. |
| 2011/0071527 A1 | 3/2011 | Nelson et al. |
| 2011/0098531 A1 | 4/2011 | To |
| 2011/0098628 A1 | 4/2011 | Yeung et al. |
| 2011/0130838 A1 | 6/2011 | Morgenstern Lopez |
| 2011/0144687 A1 | 6/2011 | Kleiner |
| 2011/0153020 A1 | 6/2011 | Abdelgany et al. |
| 2011/0172774 A1 | 7/2011 | Varela |
| 2011/0184234 A1 | 7/2011 | Morgenstren et al. |
| 2011/0208226 A1* | 8/2011 | Fatone ............... A61B 5/296 607/117 |
| 2011/0230965 A1 | 9/2011 | Schell et al. |
| 2011/0238072 A1 | 9/2011 | Tyndall |
| 2011/0282453 A1 | 11/2011 | Greenhalgh et al. |
| 2012/0059474 A1 | 3/2012 | Weiman |
| 2012/0059475 A1 | 3/2012 | Weiman |
| 2012/0059480 A1 | 3/2012 | Schell et al. |
| 2012/0065734 A1 | 3/2012 | Barre, I et al. |
| 2012/0089228 A1 | 4/2012 | Poulos |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191194 A1 | 7/2012 | Olmos et al. |
| 2012/0197405 A1 | 8/2012 | Cuevas et al. |
| 2012/0203347 A1 | 8/2012 | Glerum et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0265309 A1 | 10/2012 | Glerum et al. |
| 2012/0277864 A1 | 11/2012 | Brodke et al. |
| 2012/0290090 A1 | 11/2012 | Glerum et al. |
| 2012/0290091 A1 | 11/2012 | Kirschman |
| 2012/0290097 A1 | 11/2012 | Cipoletti et al. |
| 2012/0323328 A1 | 12/2012 | Weiman |
| 2012/0330421 A1 | 12/2012 | Weiman |
| 2012/0330422 A1 | 12/2012 | Weiman |
| 2013/0006361 A1 | 1/2013 | Glerum et al. |
| 2013/0023993 A1 | 1/2013 | Weiman |
| 2013/0023994 A1 | 1/2013 | Glerum |
| 2013/0053894 A1 | 2/2013 | Gamache et al. |
| 2013/0190769 A1 | 7/2013 | Morgenstern et al. |
| 2013/0289726 A1 | 10/2013 | Curran et al. |
| 2013/0297027 A1 | 11/2013 | Cowan |
| 2014/0058513 A1 | 2/2014 | Gahman et al. |
| 2014/0067069 A1 | 3/2014 | Lopez |
| 2014/0074242 A1 | 3/2014 | Hansell |
| 2014/0100595 A1 | 4/2014 | Morgenstern et al. |
| 2014/0100660 A1 | 4/2014 | Morgenstern et al. |
| 2014/0128977 A1 | 5/2014 | Glerum et al. |
| 2014/0135846 A1 | 5/2014 | Butler et al. |
| 2014/0135934 A1 | 5/2014 | Hansell et al. |
| 2014/0142641 A1 | 5/2014 | Black et al. |
| 2014/0142701 A1 | 5/2014 | Weiman |
| 2014/0155695 A1 | 6/2014 | Jansen et al. |
| 2014/0163620 A1 | 6/2014 | Dwyer et al. |
| 2014/0163682 A1 | 6/2014 | Lott et al. |
| 2014/0163685 A1 | 6/2014 | Hansell et al. |
| 2014/0172101 A1 | 6/2014 | Glerum |
| 2014/0214164 A1 | 7/2014 | Schell et al. |
| 2014/0214165 A1 | 7/2014 | Schell et al. |
| 2014/0236296 A1 | 8/2014 | Wagner et al. |
| 2014/0249630 A1 | 9/2014 | Weiman |
| 2014/0257296 A1 | 9/2014 | Morgenstern Lopez |
| 2014/0257490 A1 | 9/2014 | Himmelberger et al. |
| 2014/0277473 A1 | 9/2014 | Perrow |
| 2014/0277487 A1 | 9/2014 | Davenport et al. |
| 2014/0277489 A1 | 9/2014 | Davenport et al. |
| 2014/0277490 A1 | 9/2014 | Perloff et al. |
| 2014/0288606 A1 | 9/2014 | Pagano |
| 2014/0303731 A1 | 10/2014 | Glerum |
| 2014/0303732 A1 | 10/2014 | Rhoda et al. |
| 2014/0316427 A1 | 10/2014 | Yoon et al. |
| 2014/0316522 A1 | 10/2014 | Weiman et al. |
| 2014/0324171 A1 | 10/2014 | Glerum et al. |
| 2014/0371797 A1 | 12/2014 | Seifert et al. |
| 2015/0012101 A1 | 1/2015 | Glerum et al. |
| 2015/0018883 A1 | 1/2015 | Bucci et al. |
| 2015/0025633 A1 | 1/2015 | Mclaughlin et al. |
| 2015/0045889 A1 | 2/2015 | Klimek et al. |
| 2015/0051647 A1 | 2/2015 | Suh |
| 2015/0051701 A1 | 2/2015 | Glerum et al. |
| 2015/0051703 A1 | 2/2015 | Glerum et al. |
| 2015/0051704 A1 | 2/2015 | Duffield et al. |
| 2015/0057754 A1 | 2/2015 | Reed et al. |
| 2015/0066087 A1 | 3/2015 | Ingalhalikar et al. |
| 2015/0073418 A1 | 3/2015 | Landes |
| 2015/0073487 A1 | 3/2015 | Crawford et al. |
| 2015/0080896 A1 | 3/2015 | To et al. |
| 2015/0094610 A1 | 4/2015 | Morgenstern et al. |
| 2015/0094811 A1 | 4/2015 | Roche et al. |
| 2015/0100123 A1 | 4/2015 | Weiman |
| 2015/0100124 A1 | 4/2015 | Whipple |
| 2015/0100128 A1 | 4/2015 | Glerum et al. |
| 2015/0100130 A1 | 4/2015 | Perrow |
| 2015/0100131 A1 | 4/2015 | Rhoda et al. |
| 2015/0112398 A1 | 4/2015 | Morgenstern et al. |
| 2015/0173917 A1 | 6/2015 | Radcliffe et al. |
| 2015/0182234 A1 | 7/2015 | Mahoney et al. |
| 2015/0223948 A1 | 8/2015 | Lopez |

FOREIGN PATENT DOCUMENTS

| | | |
|---|---|---|
| CN | 101573069 A | 11/2009 |
| EP | 1468652 A1 | 10/2004 |
| EP | 2096982 A2 | 9/2009 |
| EP | 2331023 A2 | 6/2011 |
| EP | 2683310 A1 | 1/2014 |
| EP | 2890332 A1 | 7/2015 |
| ES | 2094077 A1 | 1/1997 |
| ES | 2279733 A1 | 8/2007 |
| ES | 2334622 A1 | 3/2010 |
| ES | 2361099 A1 | 6/2011 |
| JP | 2006-500168 | 1/2006 |
| JP | 2008-508943 | 3/2008 |
| JP | 2010-540196 | 12/2010 |
| KR | 10-2009-0086561 A | 8/2009 |
| WO | 97/29680 A1 | 8/1997 |
| WO | 00/76409 A1 | 12/2000 |
| WO | 03/21308 A2 | 3/2003 |
| WO | 2004/076409 A2 | 9/2004 |
| WO | 2006/017507 A2 | 2/2006 |
| WO | 2007/119212 A2 | 10/2007 |
| WO | 2008/064842 A2 | 6/2008 |
| WO | 2009/046414 A1 | 4/2009 |
| WO | 2009/147527 A2 | 12/2009 |
| WO | 2009/152919 A1 | 12/2009 |
| WO | 2010/115134 A1 | 10/2010 |
| WO | 2010/136170 A1 | 12/2010 |
| WO | 2010/148112 A1 | 12/2010 |
| WO | 2011/079910 A2 | 7/2011 |
| WO | 2011/142761 A1 | 11/2011 |
| WO | 2011/150350 A1 | 12/2011 |
| WO | 2012/122294 A1 | 9/2012 |
| WO | 2014/036178 A1 | 3/2014 |

OTHER PUBLICATIONS

Australian Examination Report, re AU Application No. 2012225473, dated Aug. 11, 2015.

Folman, et al., Posterior Lumbar Interbody Fusion for Degenerative Disc Disease Using a Minimally Invasive B-Twin Expandable Spinal Spacer, Journal of Spinal Disorders & Techniques, 2003, vol. 16, No. 5,455-460.

(56) References Cited

OTHER PUBLICATIONS

Gray's Anatomy, Crown Publishers, Inc., 1977, pp. 33-54.
Iprenburg et al., "Transforaminal Endoscopic Surgery in Lumbar Disc Herniation in an Economic Crisis—The Tessys Method". US Musculoskeletal, 2008 pp. 47-49.
Iprenburg, Percutaneous Transforaminal Endoscopic Discectomy: The Thessys Method, Chapter 5(4), 2008, 65-81.
Jun. 25, 2012 International Search Report and Written Opinion for PCT Application No. PCT/US2012/028110, the PCT counterpart of the present application.
Kambin et al., Percutaneous Lateral Discectomy of the Lumbar Spine: A Preliminary Report; Clin. Orthop.; 1983; 174: 127-132.
Kambin, et al; Percutaneous Posterolateral Discectomy, Anatomy and Mechanism; Clin. Orthop. Relat. Res.; Oct. 1987; 223: 145-154.
May 23, 2016 Australian Second Exam Report for Application No. AU 2012225473, the Australian counterpart of the present application.
Morgenstern R; Transforaminal Endoscopic Stenosis Surgery—A Comparative Study of Laser and Reamed Foraminoplasty, In: European Musculoskeletal Review, Issue 1, 2009.
Osman, et al., Endoscopic transforaminal decompression, interbody fusion, and percutaneous pedicle screw implantation of the lumbar spine: A case series report, Inti Journal of Spine Surgery, (6), 2012,157-166.
ProMap Trademark EMG Navigation Probe, Technical Brochure Spineology Inc., Dated May 2009.
Sep. 10, 2013 International Preliminary Report on Patentability (and Written Opinion) for PCT Application No. PCT/US2012/028110, the PCT counterpart of the present application.
Sep. 24, 2013 International Preliminary Report on Patentability (and Written Opinion) for PCT Applicaton No. PCT/US2012/029707, the PCT counterpart of the present application.
Suess et al., Motor Nerve Root Monitoring During Percutaneous Transforaminal Endoscopic Sequestrectomy Under General Anesthesia for Intra- and Extraforaminal Lumbar Disc Herniation, Zentralbl Neurochir, 2005, 66,190-201.

* cited by examiner

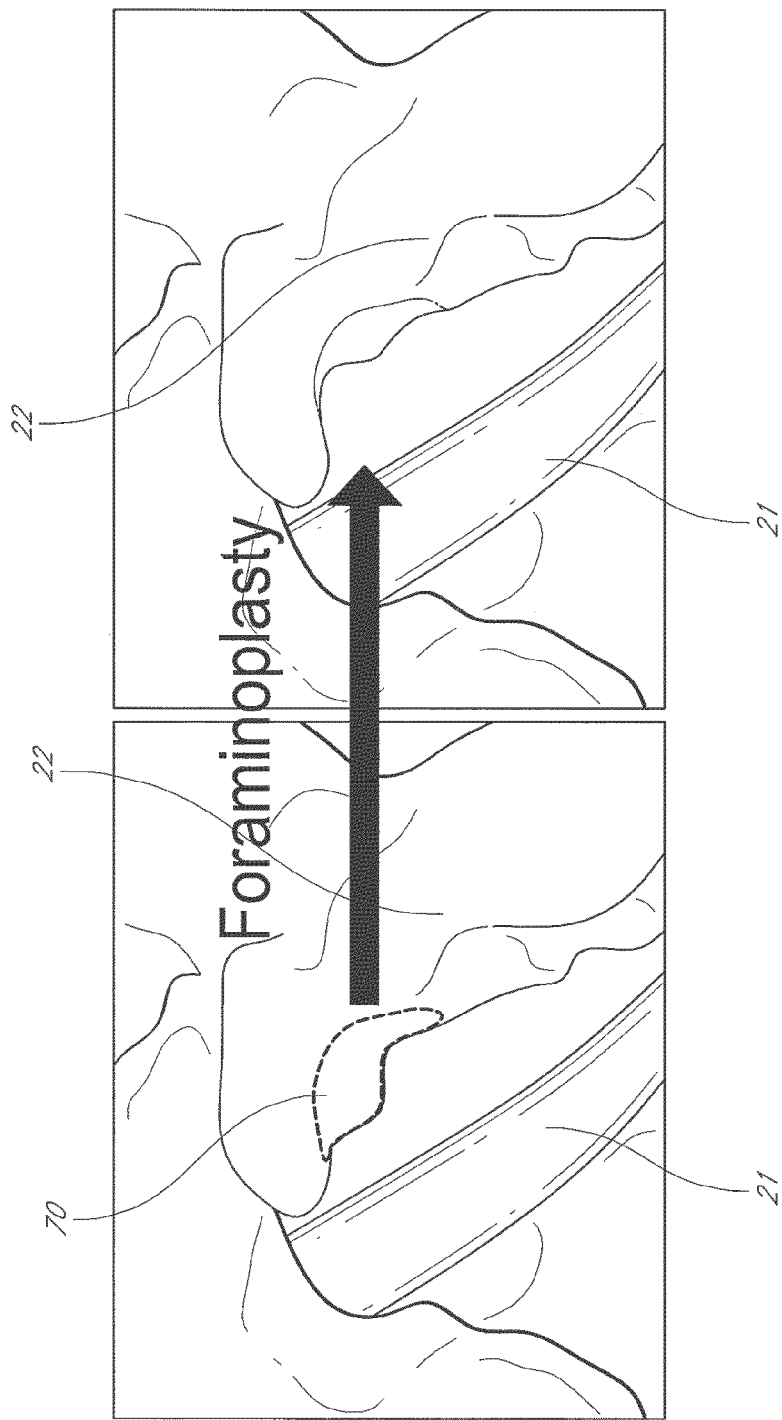

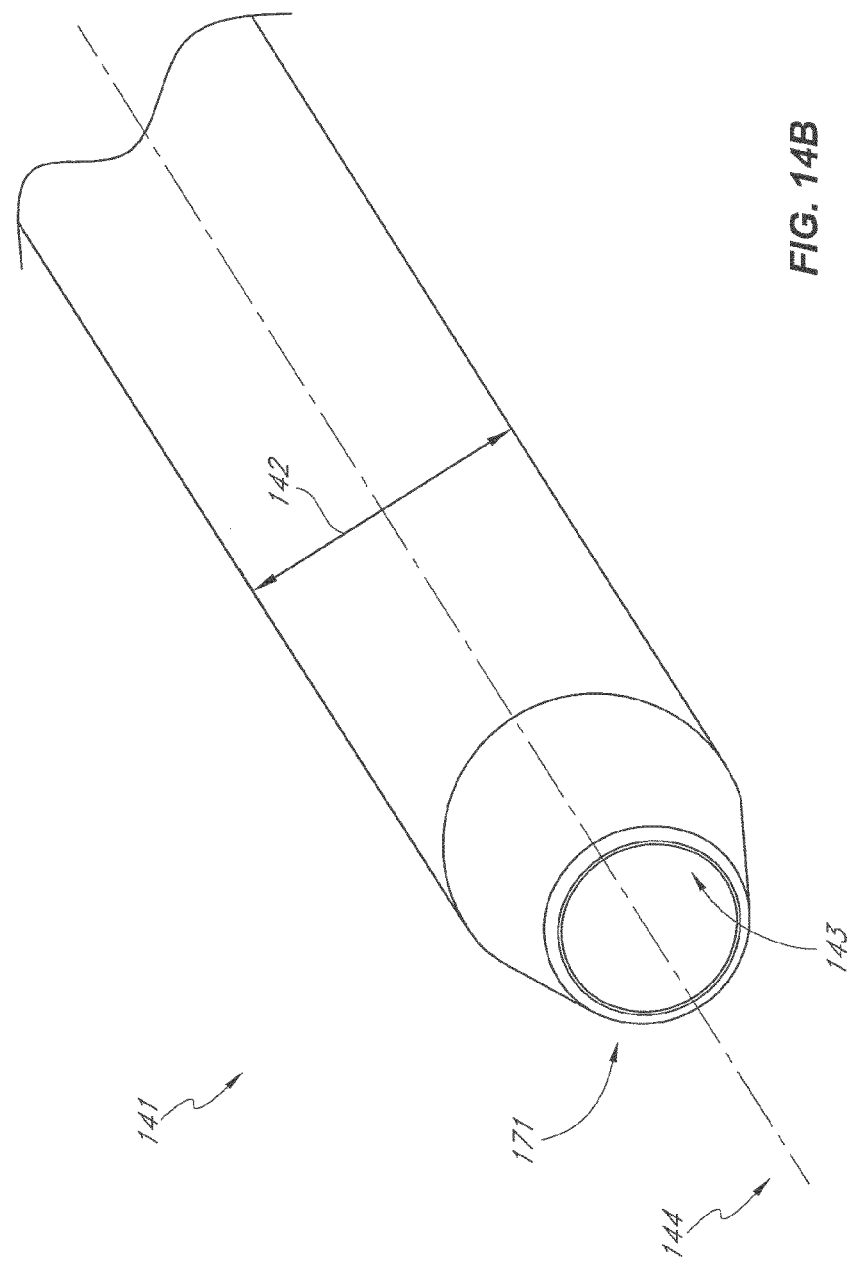

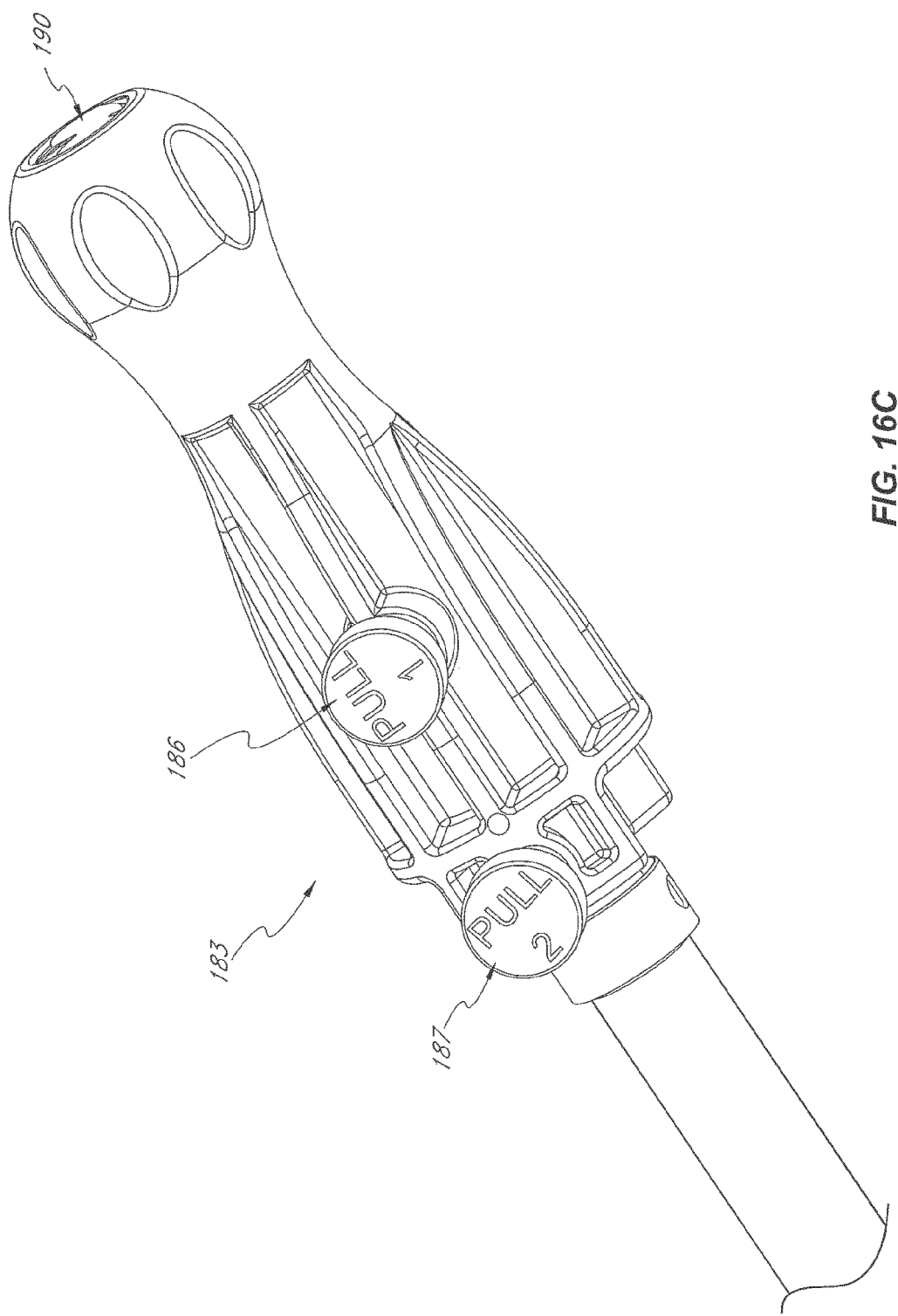

METHOD AND APPARATUS FOR MINIMALLY INVASIVE INSERTION OF INTERVERTEBRAL IMPLANTS

CROSS-REFERENCE TO RELATED APPLICATIONS

This is a continuation of U.S. patent application Ser. No. 15/835,534, filed Dec. 8, 2017, which is a divisional of U.S. patent application Ser. No. 15/290,335, filed Oct. 11, 2016, which is a continuation of U.S. patent application Ser. No. 14/454,418, filed Aug. 7, 2014, which is a continuation of U.S. patent application Ser. No. 13/934,003, filed Jul. 2, 2013, which is a continuation of U.S. patent application Ser. No. 13/416,889, filed Mar. 9, 2012, which claim priority to U.S. Provisional Application No. 61/530,031, filed Sep. 1, 2011, to U.S. Provisional Application No. 61/504,120, filed Jul. 1, 2011, to U.S. Provisional Application No. 61/471,030, filed Apr. 1, 2011, to U.S. Provisional Application No. 61/451,379, filed Mar. 10, 2011, and U.S. patent application Ser. No. 13/416,889, is a continuation-in-part of U.S. application Ser. No. 13/245,130, filed Sep. 26, 2011. The entire disclosures of U.S. patent application Ser. No. 15/835,534, filed Dec. 8, 2017, U.S. patent application Ser. No. 15/290,335, filed Oct. 11, 2016, U.S. patent application Ser. No. 14/454,418, filed Aug. 7, 2014, U.S. patent application Ser. No. 13/934,003, filed Jul. 2, 2013, U.S. patent application Ser. No. 13/416,889, filed Mar. 9, 2012, U.S. Provisional Application No. 61/530,031, filed Sep. 1, 2011, U.S. Provisional Application No. 61/504,120, filed Jul. 1, 2011, U.S. Provisional Application No. 61/471,030, filed Apr. 1, 2011, U.S. Provisional Application No. 61/451,379, filed Mar. 10, 2011, and U.S. application Ser. No. 13/245,130, filed Sep. 26, 2011 are hereby incorporated by reference in their entireties and should be considered a part of this specification.

BACKGROUND OF THE INVENTION

Field of the Invention

The present application relates to medical devices and, more particularly, to a medical device and method for treating the spine.

Description of the Related Art

The human spine is a flexible weight bearing column formed from a plurality of bones called vertebrae. There are thirty-three vertebrae, which can be grouped into one of five regions (cervical, thoracic, lumbar, sacral, and coccygeal). Moving down the spine, there are generally seven cervical vertebrae, twelve thoracic vertebrae, five lumbar vertebrae, five sacral vertebrae, and four coccygeal vertebrae. The vertebrae of the cervical, thoracic, and lumbar regions of the spine are typically separate throughout the life of an individual. In contrast, the vertebra of the sacral and coccygeal regions in an adult are fused to form two bones, the five sacral vertebrae which form the sacrum and the four coccygeal vertebrae which form the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. In addition, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Spinal fusion is one such method. In spinal fusion, one or more of the vertebra of the spine are united together ("fused") so that motion no longer occurs between them. Thus, spinal fusion is the process by which the damaged disc is replaced and the spacing between the vertebrae is restored, thereby eliminating the instability and removing the pressure on neurological elements that cause pain.

Spinal fusion can be accomplished by providing an intervertebral implant between adjacent vertebrae to recreate the natural intervertebral spacing between adjacent vertebrae. Once the implant is inserted into the intervertebral space, osteogenic substances, such as autogenous bone graft or bone allograft, can be strategically implanted adjacent the implant to prompt bone ingrowth in the intervertebral space. The bone ingrowth promotes long-term fixation of the adjacent vertebrae. Various posterior fixation devices (e.g., fixation rods, screws etc.) can also be utilize to provide additional stabilization during the fusion process.

Notwithstanding the variety of efforts in the prior art described above, these intervertebral implants and techniques are associated with another disadvantage. In particular, these techniques typically involve an open surgical procedure, which results in higher cost, lengthy in-patient hospital stays and the pain associated with open procedures. In addition, many intervertebral implants are inserted anteriorly while posterior fixation devices are inserted posteriorly. This results in additional movement of the patient. Therefore, there remains a need in the art for an improved apparatus and method for introducing an intervertebral implant.

SUMMARY OF THE INVENTION

In one embodiment, the implant is advantageously introduced via a minimally invasive procedure, taking a posterolateral approach at least partially through Kambin's triangle in a manner that advantageously provides protection to the exiting and traversing nerves. In one arrangement, to facilitate introduction of instruments and/or devices at least partially through Kambin's triangle a foraminoplasty is formed. In one embodiment, the foraminoplasty is performed using one or more features provided one or more dilation tubes that can be used to dilate tissue.

In accordance with an embodiment, a dilation introducer for orthopedic surgery comprises a first dilator tube having a distal portion and a proximal portion, the outer surface of the first dilator tube having a first outer radius centered around a first longitudinal axis, and a first longitudinal lumen having a first inner radius; a second dilator tube having a distal portion and a proximal portion, the second dilator tube having a second outer radius centered around a second longitudinal axis, a second longitudinal lumen having a second inner radius centered around the first longitudinal axis, the distal portion of the second dilator tube having a generally semi-annular cross-section, the second lumen configured for removably receiving the first dilator tube for slidable movement within the second lumen; wherein the first longitudinal axis is parallel to and laterally offset from the second longitudinal axis.

In some embodiments, the dilation introducer can be configured for removably connecting the first and second dilator tubes together in a locked arrangement, whereby in the locked arrangement slidable movement is restricted. In some embodiments, the second dilator tube can be rotatable with respect to the first dilator tube around the first longitudinal axis. In certain embodiments, the generally semi-annular cross-section of the second dilator tube can be configured such that when the first dilator tube is received within the second dilator tube, the outer radial surface of the first dilator tube is partially exposed at the distal end of the first dilator tube. Further, the opening of the generally semi-annular cross-section of the second dilator tube can be oriented opposite the second longitudinal axis with respect to the first longitudinal axis. In some embodiments, the second dilator tube can contain cutting flutes on one side, located opposite the opening of the generally semi-annular cross-section of the second dilator tube.

In some embodiments, the dilation introducer can further comprise: a third dilator tube having a distal portion and a proximal portion, the third dilator tube having a third outer radius centered around a third longitudinal axis, a third longitudinal lumen having a third inner radius centered around the second longitudinal axis, the distal portion of the third dilator tube having a semi-annular cross-section, the third lumen configured for removably receiving the second dilator tube for slidable movement within the third lumen; wherein the second longitudinal axis is parallel to and laterally offset from the third longitudinal axis. Further, the dilation introducer can comprise: an access cannula having a distal portion and a proximal portion, the access cannula having a fourth outer radius centered around the third longitudinal axis, a fourth longitudinal lumen having a fourth inner radius centered around the third longitudinal axis, the distal portion of the access cannula having a semi-annular cross-section, the fourth lumen configured for removably receiving the third dilator tube for slidable movement within the fourth lumen. In some embodiments, the access cannula can have a smooth outer surface.

In accordance with an embodiment, a method for accessing a patient's intervertebral disc to be treated in orthopedic surgery is provided, comprising the steps of: passing a first dilator tube along a first longitudinal axis through Kambin's triangle until the first dilator tube reaches the intervertebral disc to be treated; passing a second dilator tube along a second longitudinal axis that is parallel to and laterally displaced from the first longitudinal axis, until the distal end of the second dilator contacts the annulus, wherein the second dilator tube has a coarse portion oriented towards the inferior pedicle, and wherein the distal portion of the second dilator tube has a generally semi-annular cross-section, configured such that the second dilator tube does not contact the exiting nerve during insertion.

In some embodiments, the method can further comprise: passing a third dilator tube along a third longitudinal axis that is parallel to and laterally displaced from the second longitudinal axis, until the distal end of the third dilator contacts the annulus, wherein the distal portion of the third dilator tube has cutting flutes oriented towards the inferior pedicle, and wherein the distal portion of the third dilator tube has a generally semi-annular cross-section configured such that the third dilator tube does not contact the exiting nerve during insertion. Further, the method can comprise forming a further recess in the inferior pedicle by rotating the second dilator tube back and forth. Alternatively or in addition, the method can further comprise forming a further recess in the inferior pedicle by longitudinally sliding the second dilator tube back and forth. Further still, the method can also comprise: passing an access cannula over the third dilator tube until the distal end of the third dilator contacts the annulus, wherein the distal portion of the access cannula has a generally semi-annular cross-section configured such that the access cannula does not contact the exiting nerve during insertion; rotating the access cannula such that generally semi-annular cross-section opens opposite the exiting nerve; and removing the first, second, and third dilator tubes. In some embodiments, the method can further comprise operating on an intervertebral disc by inserting surgical instruments through the access cannula.

In accordance with an embodiment, a method for performing orthopedic surgery is provided that can comprise: introducing a first dilator tube through Kambin's triangle; introducing a second dilator tube over the first dilator tube; and removing bone from the inferior pedicle. In some embodiments, the method can further comprise: introducing a third dilator tube over the second dilator tube; and removing additional bone from the inferior pedicle. In some embodiments, the method can further comprise: introducing an access cannula over the third dilator tube; and operating on the spine through the access cannula.

In accordance with an embodiment, a dilation introducer for orthopedic surgery is provided that can comprise a first dilator tube having a distal portion and a proximal portion, the outer surface of the first dilator tube having a first outer radius centered around a first longitudinal axis, and a first longitudinal lumen having a first inner radius; and a second dilator tube having a distal portion and a proximal portion, the second dilator tube having a second outer radius centered around a second longitudinal axis, a second longitudinal lumen having a second inner radius centered around the first longitudinal axis, the second dilator tube configured to be slidably advanced over the first dilator tube. In some embodiments, the distal portions first and second dilator tubes both include cutting surfaces on one outer side of the dilator and a generally smooth surface on an opposite outer side of the dilator tube. In some embodiments, the dilation introducer further includes a neuro-monitoring needle.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 11 shows the access point before and after the foraminoplasty performed by the dilation introducer of FIG. 7A.

FIG. 14B is an enlarged detail view of the distal end of the first dilator tube shown in FIG. 14A.

FIGS. 16C and 16D are enlarged detail views of the proximal end of the third dilator tube shown in FIG. 16A.

DETAILED DESCRIPTION OF THE PREFERRED EMBODIMENTS

In accordance with certain embodiments disclosed herein, an improved apparatus for inserting an intervertebral implant is provided. For example, in one embodiment, the apparatus may be used to insert surgical instruments and/or one or more intervertebral implants through a minimally invasive procedure to reduce trauma to the patient and thereby enhance recovery and improve overall results. By minimally invasive, Applicant means a procedure performed percutaneously through an access device in contrast to a typically more invasive open surgical procedure.

Certain embodiments disclosed herein are discussed in the context of an intervertebral implant and spinal fusion because of the device and methods have applicability and usefulness in such a field. The device can be used for fusion, for example, by inserting an intervertebral implant to properly space adjacent vertebrae in situations where a disc has ruptured or otherwise been damaged. "Adjacent" vertebrae can include those vertebrae originally separated only by a disc or those that are separated by intermediate vertebra and discs. Such embodiments can therefore be used to create proper disc height and spinal curvature as required in order to restore normal anatomical locations and distances. However, it is contemplated that the teachings and embodiments disclosed herein can be beneficially implemented in a variety of other operational settings, for spinal surgery and otherwise.

Figure 1:
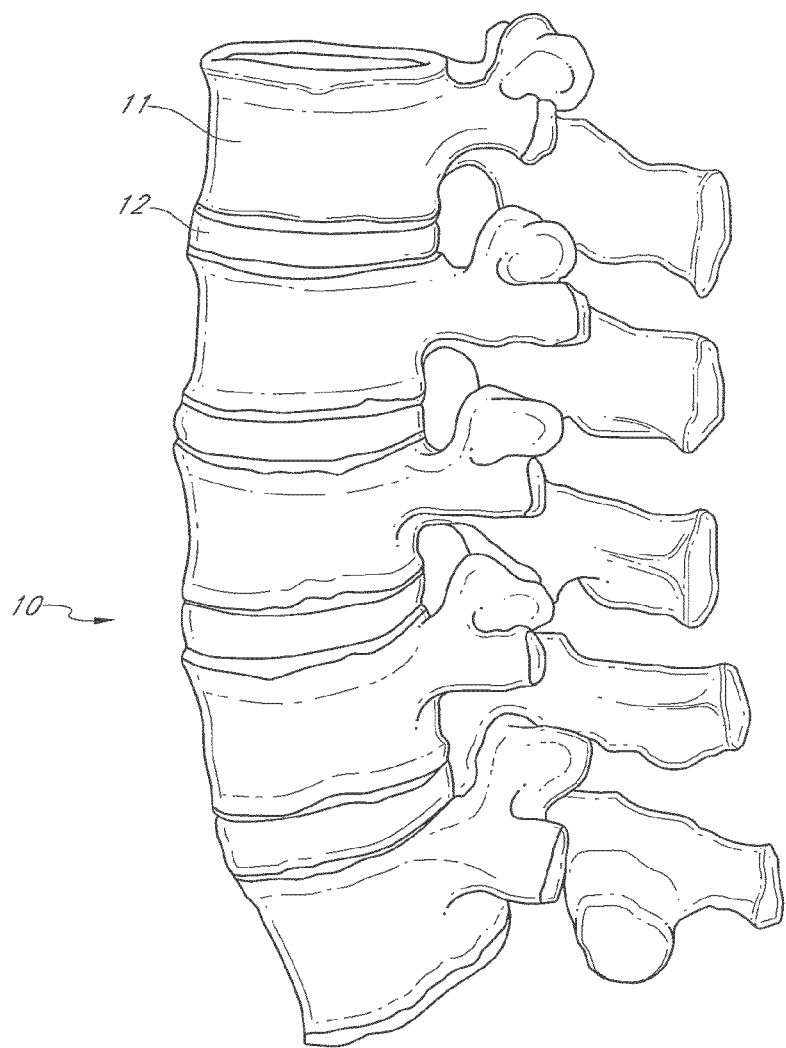
FIG. 1 is a lateral elevational view of a portion of a vertebral column.

As context for the methods and devices described herein, FIG. 1 is a lateral view of a vertebral column 10. As shown in FIG. 1, the vertebral column 10 comprises a series of alternative vertebrae 11 and fibrous intervertebral discs 12 that provide axial support and movement to the upper portions of the body. The vertebral column 10 typically comprises thirty-three vertebrae 11, with seven cervical (C1-C7), twelve thoracic (T1-T12), five lumbar (L1-L5), five fused sacral (S1-S5), and four fused coccygeal vertebrae.

Figure 2:
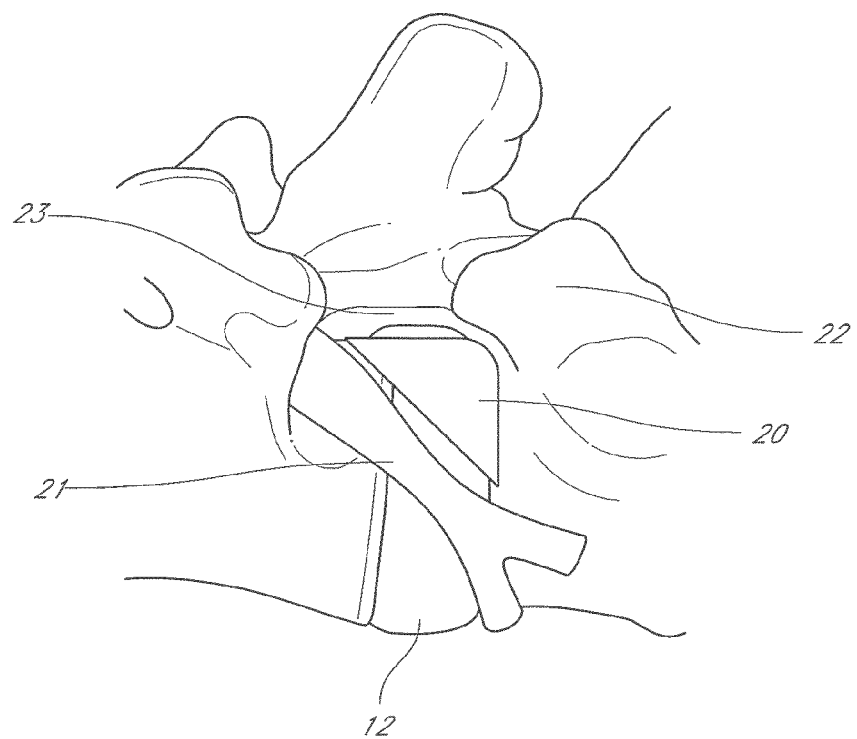
FIG. 2 is a schematic side view of Kambin's triangle.

FIG. 2 is a schematic view of Kambin's triangle. This region 20 is the site of posterolateral access for spinal surgery. It can be defined as a right triangle over the intervertebral disc 12 viewed dorsolaterally. The hypotenuse is the exiting nerve 21, the base is the superior border of the inferior vertebra 22, and the height is the traversing nerve root 23. As will be explained below, in one embodiment, the intervertebral disc 12 is accessed through this region by performing a foraminoplasty in which a portion of the inferior vertebra is removed such that surgical instruments or implants can be introduced at this region of the spine. In such a procedure, it is often desired to protect the exiting nerve and the traversing nerve root. Apparatuses and methods for accessing the intervertebral disc through Kambin's triangle may involve performing endoscopic foraminoplasty while protecting the nerve will be discussed in more detail below. Utilizing foraminoplasty to access the intervertebral disc through Kambin's triangle can have several advantages (e.g., less or reduced trauma to the patient) as compared to accessing the intervertebral disc posteriorly or anteriorly as is typically done in the art. In particular, surgical procedures involving posterior access often require removal of the facet joint. For example, transforaminal interbody lumbar fusion (TLIF) typically involves removal of one facet joint to create an expanded access path to the intervertebral disc. Removal of the facet joint can be very painful for the patient, and is associated with increased recovery time. In contrast, accessing the intervertebral disc through Kambin's triangle may advantageously avoid the need to remove the facet joint. As described in more detail below, endoscopic foraminoplasty may provide for expanded access to the intervertebral disc without removal of a facet joint. Sparing the facet joint may reduce patient pain and blood loss associated with the surgical procedure. In addition, sparing the facet joint can advantageously permit the use of certain posterior fixation devices which utilize the facet joint for support (e.g., transfacet screws, trans-pedicle screws, and/or pedicle screws). In this manner, such posterior fixation devices can be used in combination with interbody devices inserted through the Kambin's triangle.

Dilation Introducer

FIGS. 2-7B illustrate an embodiment of a dilation introducer 100 that can be used to perform percutaneous orthopedic surgery. As will be described in detail below, the dilation introducer in the illustrated embodiments can comprise an access cannula 30, and a first, second and third dilator tubes 40, 45, 60. While the illustrated embodiment includes first, second and third dilator tubes 40, modified embodiments can include more or less dilator tubes and/or dilator tubes with modified features. It is also anticipated that in some embodiments, the access cannula 30 can be eliminated from the introducer or modified.

Figure 3:
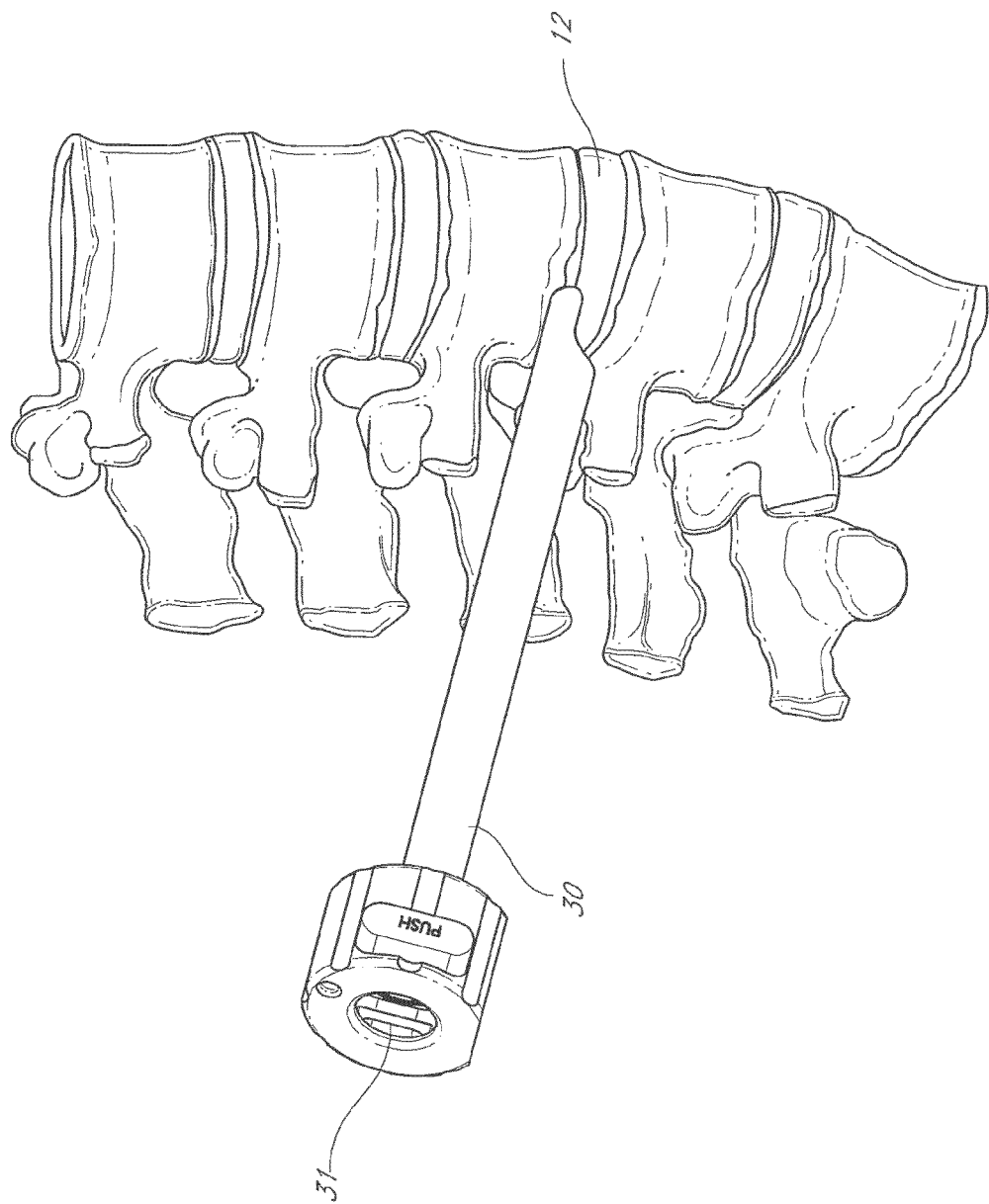
FIG. 3 is a perspective view of an access cannula in positioned against a vertebral column.

FIG. 3 illustrates an embodiment of the access cannula 30, which is shown in a position for performing surgery on an intervertebral disc, for instance transforaminal lumbar interbody fusion. The access cannula 30 in the illustrated embodiment has an inner lumen 31 that allows for surgical instruments and devices to pass through it to access the intervertebral disc 12. The distal tip of the cannula can be oriented such that surgical instruments have access to the intervertebral disc without contacting with the exiting nerve. The position shown in FIG. 3 can be achieved by following the method disclosed herein, discussed in more detail below.

Figure 4A:
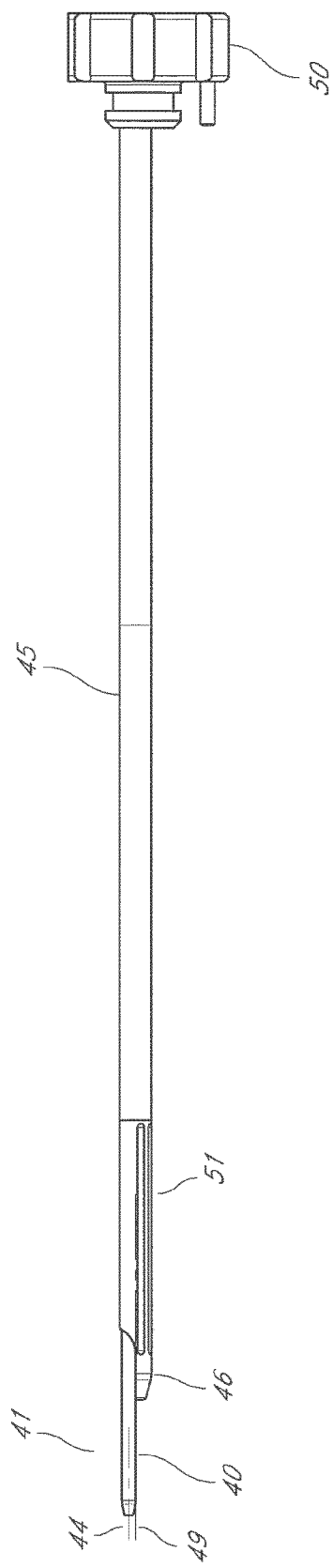
FIG. 4A is a plan view of a first and second dilator tubes in a combined position.
Figure 4B:
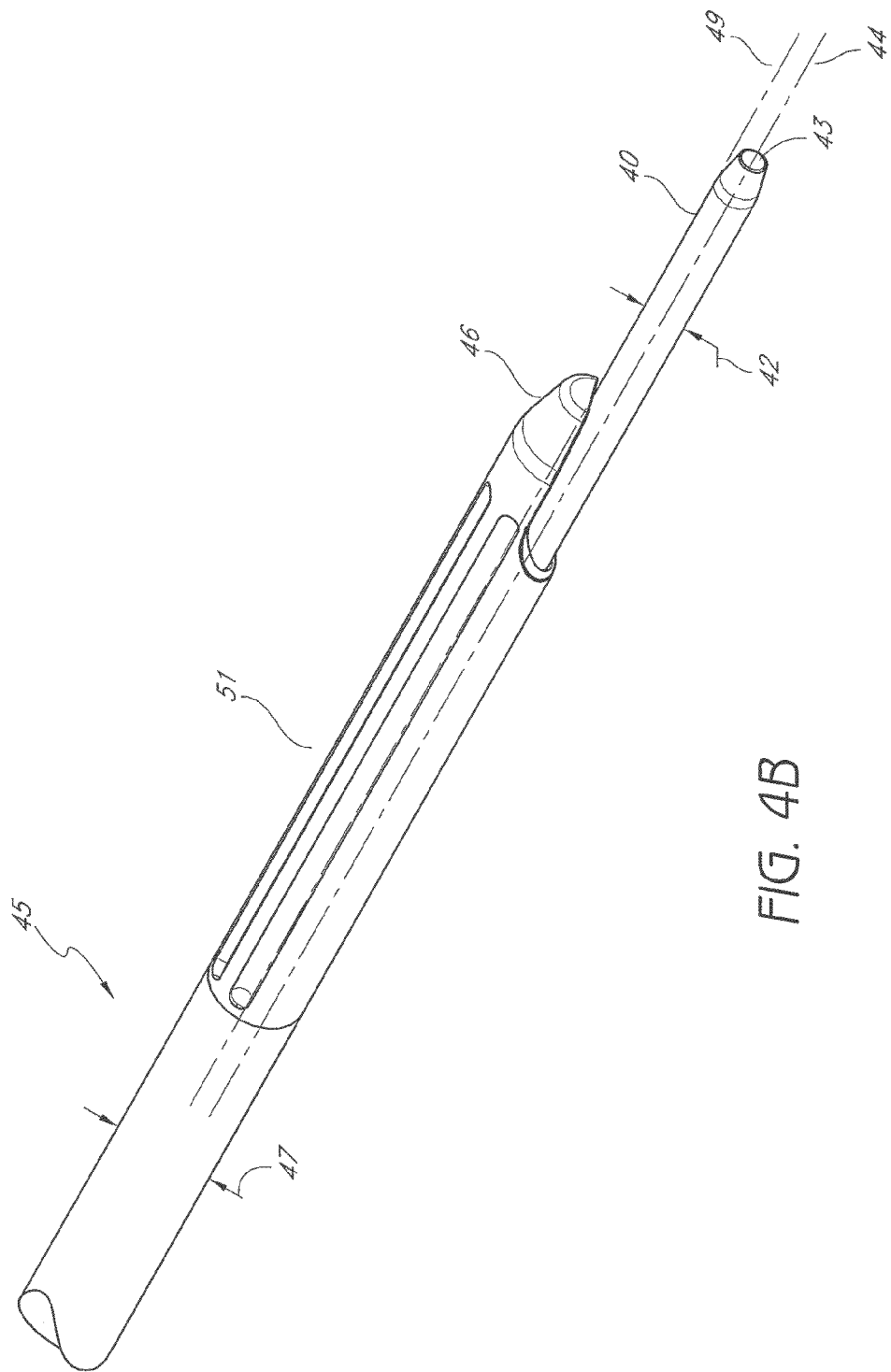
FIG. 4B is an enlarged detail view of the distal tip of the first and second dilator tubes shown in FIG. 4A.

FIGS. 4A and 4B illustrate an embodiment of the first dilator tube 40 and second dilator tube 45 of the dilation introducer 100. As shown, in the illustrated embodiment, the first dilator tube 40 has a distal portion 41, an outer radius 42 and a first longitudinal lumen 43. The illustrated second dilator tube 45 has a distal portion 46, an outer radius 47 and a second longitudinal lumen 48. As shown, the first dilator tube can be received within the lumen of the second dilator tube. The outer radius 42 of the first dilator tube can be centered around a first longitudinal axis 44. The outer radius 47 of the second dilator tube can be centered around a second longitudinal axis 49. In the illustrated embodiment, the second longitudinal axis 49 is laterally offset from the first longitudinal axis 44. In the configuration shown, the outer radius of the first dilator tube is nearly equivalent to the inner radius of the second longitudinal lumen such that the first dilator tube can be slidably received within the second dilator tub. The second dilator tube 45 can include a handle 50 for rotating the tube independently of the first dilator tube 40. In the illustrated embodiment, a collar can be located distal to the handle, with an outer radius larger than the outer radius of the second dilator tube, but smaller than the outer radius of the handle. In a modified embodiment, the first dilator tube 40 can also a separate handle which can be locked together with the handle 50 of the second dilator tube 45. In one embodiment, the first and second dilator tubes 40, 45 can locked longitudinally locked together, such that slidable movement of the first tube with respect to the second is restricted. In one embodiment, the distal portion 46 of the second dilator tube has a flattened edge. This flattened edge advantageously prevents the second dilator tube 45 from penetrating the disc.

FIG. 4B shows an enlarged detail view of the distal portions of the first and second dilator tubes 40, 45 of FIG. 4A. The distal portion 46 of the second dilator tube 45 can have a generally semi-annular cross-section, configured such that when the first dilator tube 40 is received within the second dilator tube 45, the outer radial surface of the first dilator tube 40 is partially exposed at the distal portion 46 of the second dilator tube 45. The opening of the generally semi-annular cross-section of the second dilator tube can be oriented opposite the second longitudinal axis 49 with respect to the first longitudinal axis 44. Additionally, the second dilator tube can include cutting flutes or ridges 51 on one side, located opposite the opening of the generally semi-annular cross-section of the second dilator tube 45. In other embodiments, the cutting flutes may be replaced with a coarse surface (e.g., knurling, sharp edges, abrasive members, etc.) which, when rotated or slid (e.g., back and forth) against bone, will create a recess therein. As noted above, other mechanisms for removing bone can be used, and the cutting flutes are shown here by way of example only. As can be seen in FIG. 4B, the inner lumen of the second dilator tube 45 can be off-center. In this configuration, the cutting flutes 51 are further from the axis of rotation than the side opposite the cutting flutes. This is particularly advantageous for performing foraminoplasty while protecting the exiting nerve, as will be discussed in more detail below.

Although the illustrated embodiment depicts the first and second dilator tubes as separate elements, in alternative embodiments these two tubes can be coupled formed together as one unified dilator tube with a staggered distal portion. In still other embodiments, the first dilator tube and second dilator tube may be coupled together to form a single component. The tubes may be joined by, for instance, welding, adhesive, mechanical joints, or any other appropriate means.

In another alternative embodiment, the first dilator tube may be omitted. Instead, a Jamshidi® needle with a removable handle, or a similar device, may be used to initially define a path to the intervertebral disc. With the handle of the Jamshidi® needle removed, the second dilator tube may be advanced over the Jamshidi® needle, just as with the first dilator tube. In some embodiments, a K-wire or similar device can be inserted through the Jamshidi® needle and/or dilator tubes.

Figure 5A:
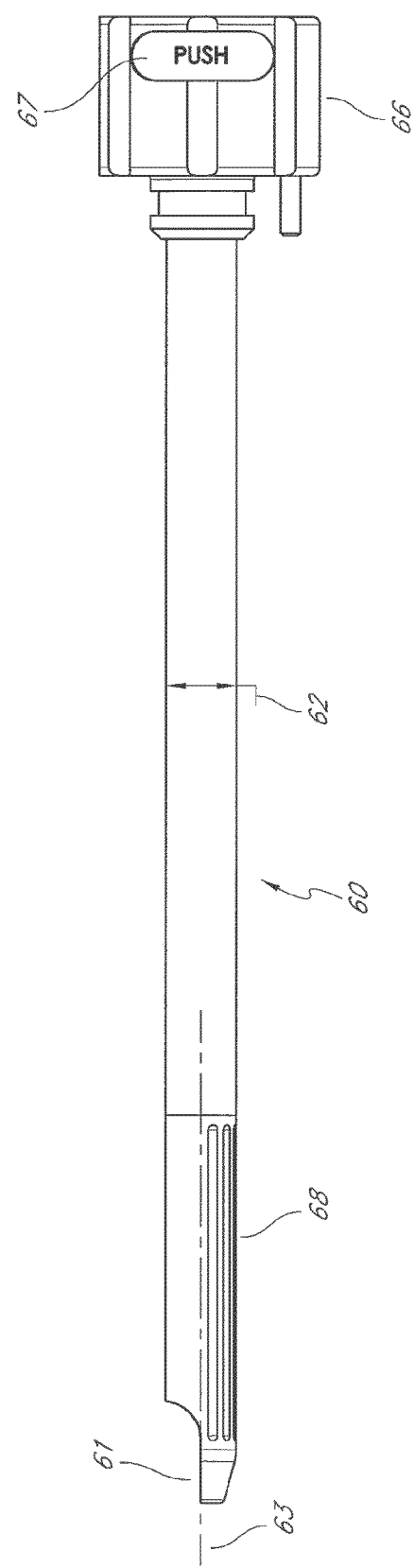
FIG. 5A is a plan view of a third dilator tube.
Figure 5B:
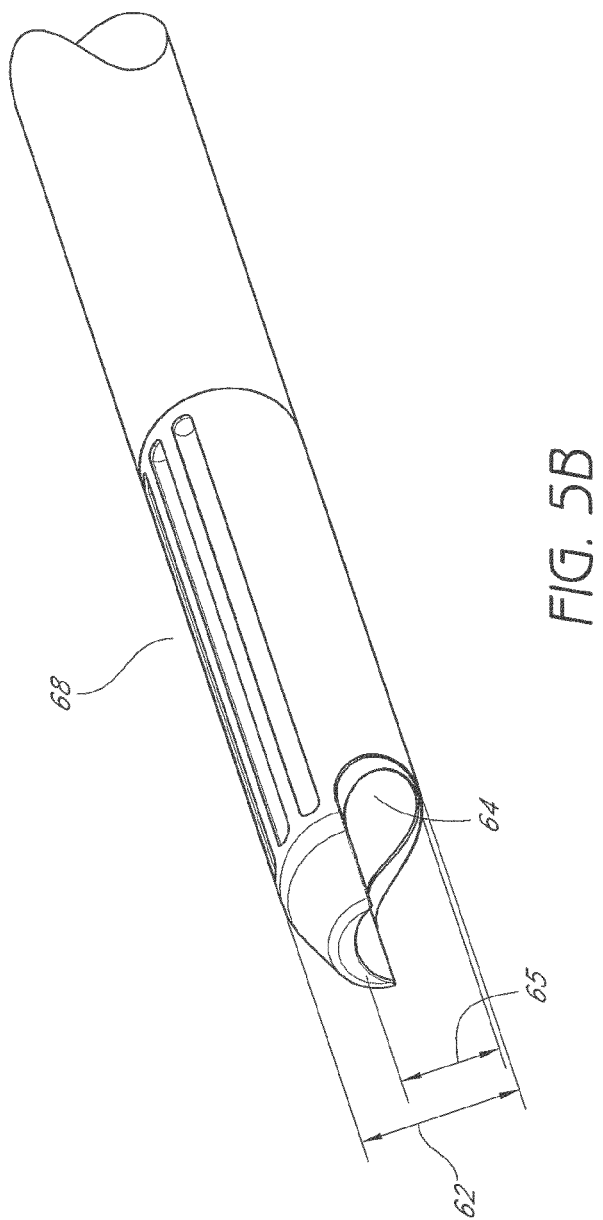
FIG. 5B is an enlarged detail view of the distal tip of the third dilator tube shown in FIG. 5A.

FIGS. 5A and 5B illustrate and embodiment of the third dilator tube 60, which can be configured to be slidably introduced over the second dilator tube 45. The third dilator tube 60 can include a distal portion 61, a third outer radius 62 centered around a third longitudinal axis 63, and a third longitudinal lumen 64 having a third inner radius 65. The third lumen 64 can be configured to removably receive the second dilator tube (not shown) for slidable movement within the third lumen 64. In such a configuration, the third longitudinal axis 63 is parallel to and laterally offset from the second longitudinal axis 49. A handle 66 can allow for rotation of the third dilator tube. In one arrangement, a collar can be located distal to the handle 66, with an outer radius larger than the outer radius of the third dilator tube 45, but smaller than the outer radius of the handle.

In some embodiments, a button 67 on the handle 66 allows for the operator to toggle between a locked and unlocked configuration. In a locked configuration, the second and third dilator tubes are unable to slide relative to one another. In an embodiment, the locked configuration permits the dilator tubes to rotate independently with respect to one another. In another embodiment, the locked configuration restrains rotational movement as well as slidable movement. The button 67 may comprise a generally rectangular shape with a cut-out large enough for the collar of the second dilator tube 45 to pass therethrough. A spring located underneath the button 67 provides upward pressure on the button. When uncompressed, the cut-out portion of the button presses firmly against the collar of the second dilator tube 45, which may be received within the handle 66 of the third dilator tube. When uncompressed, the friction of the button 67 against the collar inhibits movement of the third dilator tube 60 with respect to the second dilator tube. In some embodiments, the cut-out portion of the button may form a notch configured to fit within the ridge on the collar of the third dilator tube. Upon compressing the button 67, the cut-out portion of the button may be moved away from the collar, permitting free movement of the third dilator tube 60 relative to the second dilator tube 45.

FIG. 5B shows an enlarged detail view of the distal portion of the third dilator tube of FIG. 5A. The distal portion 61 has a generally semi-annular cross-section, and cutting flutes 167 for reaming bone located opposite the opening of the semi-annular cross-section. As with the second dilator tube, in other embodiments the cutting flutes may be replaced or used in combination with a coarse or other cutting or abrading surface which, when rotated or slid against bone, will create a recess therein. As can be seen in FIG. 5B, the inner lumen of the third dilator tube 60 may be off-center. In this configuration, the cutting flutes 68 are further from the axis of rotation than the side opposite the cutting flutes. This is particularly beneficial for performing foraminoplasty while protecting the exiting nerve, as will be discussed in more detail below.

Figure 6A:
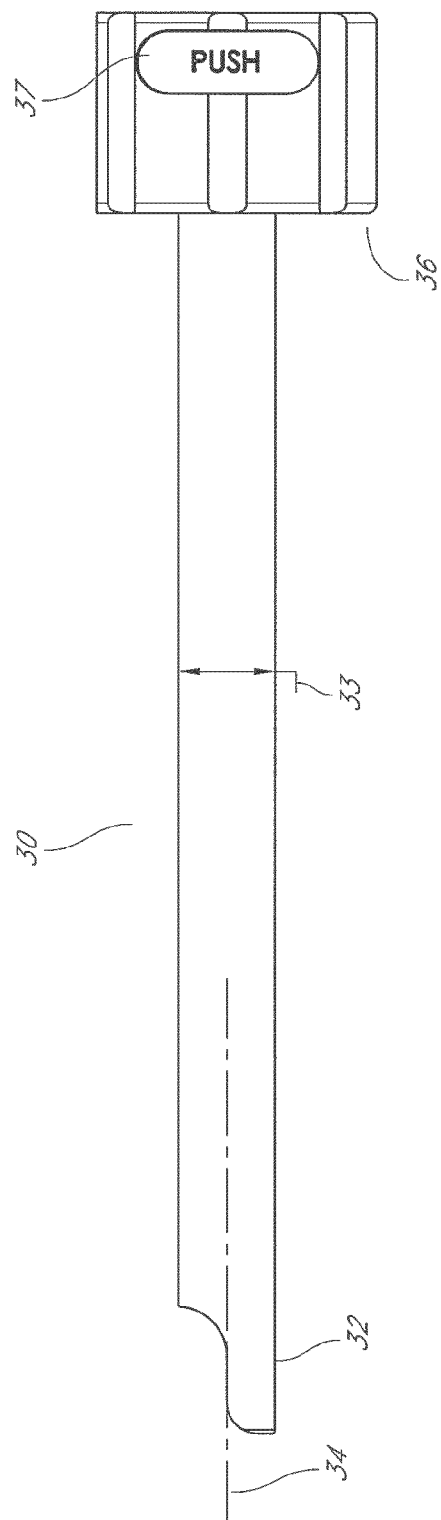
FIG. 6A is a side view of the access cannula shown in FIG. 3.
Figure 6B:
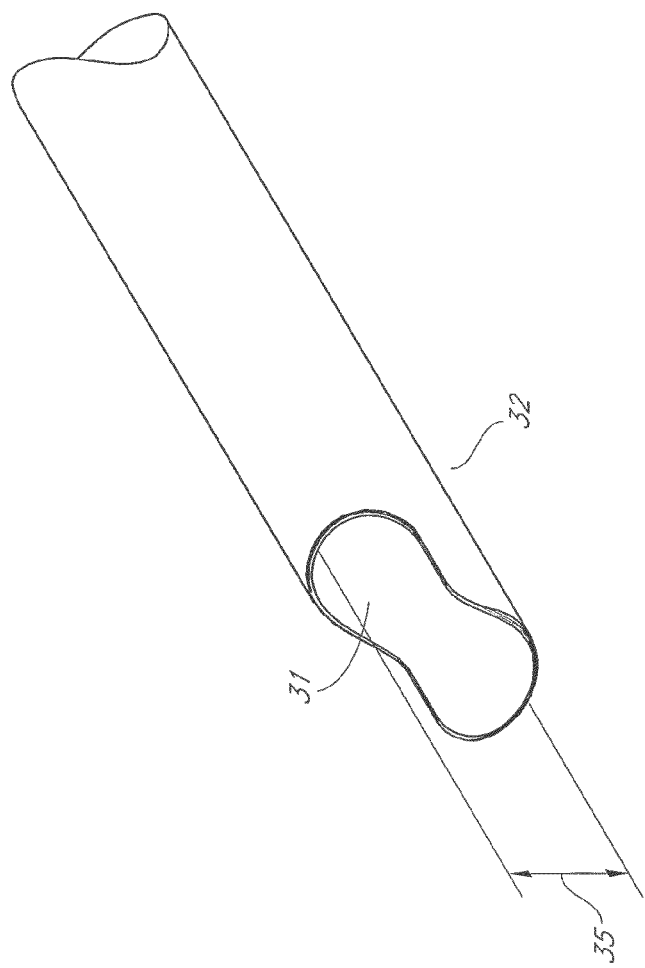
FIG. 6B is an enlarged detail view of the distal tip of the access cannula shown in FIG. 6A.

FIGS. 6A and 6B illustrate an embodiment of the access cannula, which can be configured to be introduced over the third dilator tube (not shown). The access cannula 30 has a distal portion 32, a fourth outer radius 33 centered around a fourth longitudinal axis 34, and a fourth longitudinal lumen 31 having a fourth inner radius 35. The access cannula 30 may be configured to removably receive the third dilator tube (not shown) for slidable movement within the third lumen. A handle allows for rotation of the access cannula 30.

In some embodiments, a button 37 on the handle 36 allows for the operator to toggle between a locked and unlocked configuration. In a locked configuration, third dilator tube and the access cannula are unable to slide relative to one another. In an embodiment, the locked configuration permits the dilator tubes to rotate independently with respect to one another. In another embodiment, the locked configuration restrains rotational movement as well as slidable movement. The button 37 may comprise a generally rectangular shape with a cut-out large enough for the collar of the third dilator tube 60 to pass therethrough. A spring located beneath the button 37 can provide upward pressure on the button. When uncompressed, the cut-out portion of the button can press firmly against the collar of the third dilator tube 45, which may be received within the handle of the access cannula 30. When uncompressed, the friction of the button 37 against the collar can inhibit movement of the access cannula 30 with respect to the third dilator tube 60. Upon compressing the button 37, the cut-out portion of the button can be moved away from the collar, permitting free movement of the access cannula 30 relative to the third dilator tube 60.

FIG. 6B shows an enlarged detail view of the distal portion of the access cannula of FIG. 6A. The distal portion 32 can have a generally semi-annular cross-section. In the embodiment shown, the fourth longitudinal lumen may be centered with respect to the outer radius of the access cannula, in contrast to the second and third dilator tubes. In other embodiments, however, the access cannula may also have a longitudinal lumen that may be off-center with respect to the outer radius. In yet another embodiment, the access cannula need not be limited to a cylindrical outer surface. The outer surface could, for instance, have an elliptical, polygonal, or other cross-sectional shape.

Figure 7A:
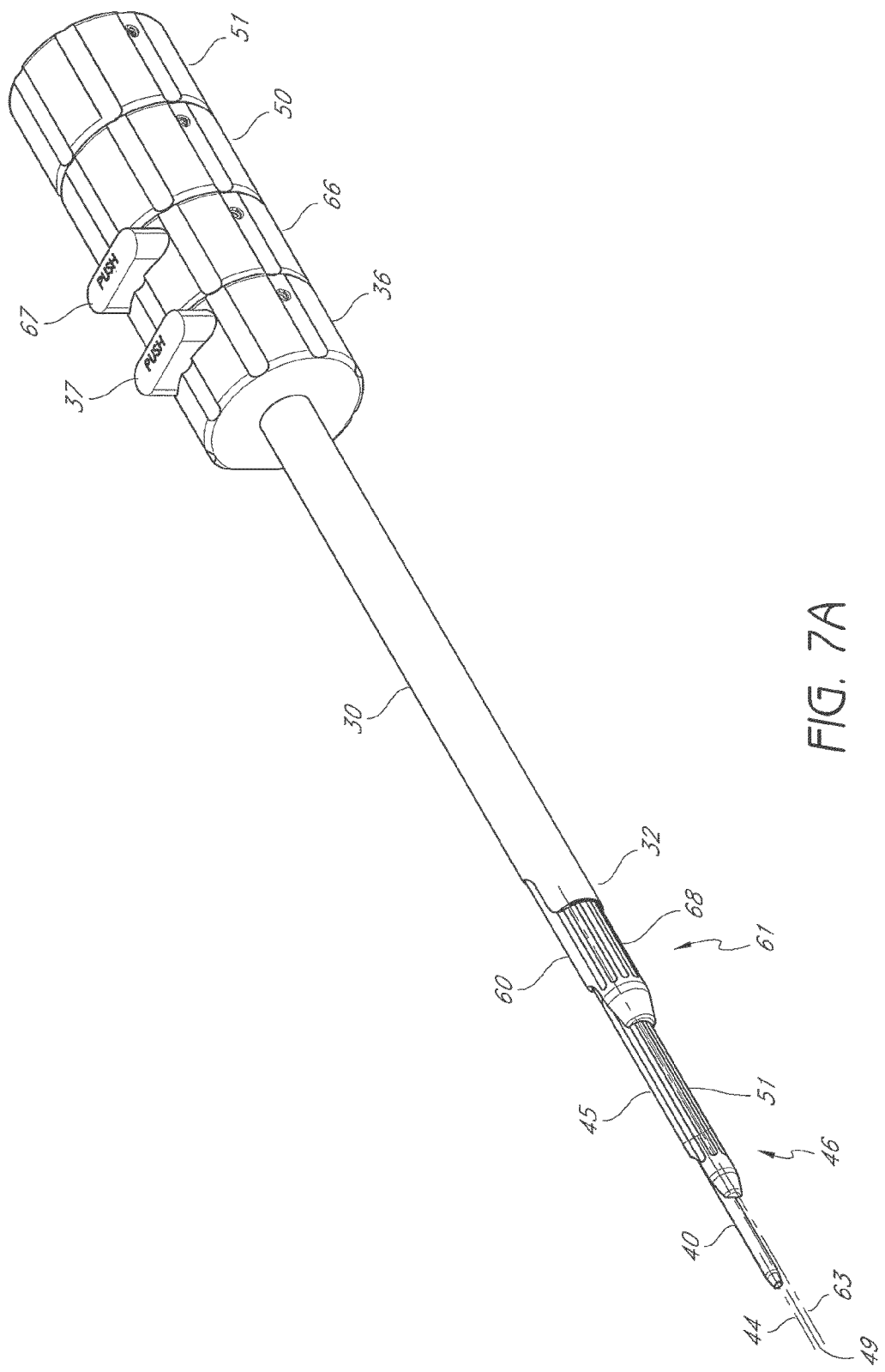
FIG. 7A is a perspective view of a dilation introducer comprising the first and second dilator tubes of FIG. 4A, the third dilator tube of FIG. 5A and the access cannula of FIG. 6A.
Figure 7B:
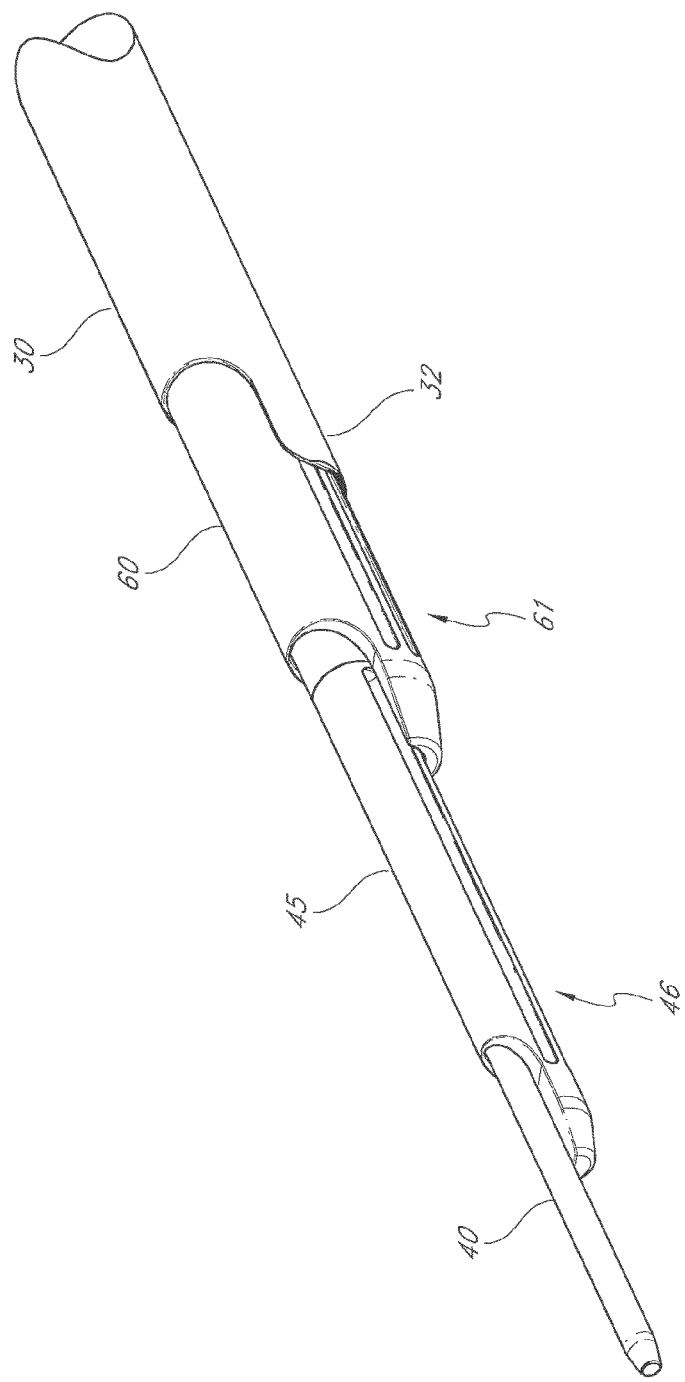
FIG. 7B is an enlarged detail view of the distal tip of dilation introducer shown in FIG. 7A.

FIGS. 7A and 7B illustrate one embodiment of the dilation introducer 100 in an assembled configuration. As shown, the access cannula 30 can be positioned over the third dilator tube 60, which can be positioned over the second dilator tube 45, which in turn can be positioned over the first dilator tube 40. The handles 50, 151 of the first and second dilator tubes can be locked together to constrain slidable movement, but allow for the second dilator tube 45 to rotate with respect to the first dilator tube 40. The third dilator tube 60 can be advanced distally until the distal portion 61 of the third dilator tube aligns with the distal portion 46 of the second dilator tube. Further, the access cannula may also be advanced so that the distal portion 32 aligns with the distal portions 46, 61 of the second and third dilator tubes. The second and third dilator tubes 45, 60 each have cutting flutes 51, 68 on their respective distal portions 46, 61. As can be seen, the first, second, and third longitudinal axes 44, 49, 63 are each laterally offset from one another.

In certain embodiments, the first, second and third dilator tubes along with the access cannula can be provided with additional stops that engage the buttons described above. For example, in one embodiment, notches or detents can be provided that engage the button when one tube is advanced distally and reaches a specific location (e.g., end point). In this manner, forward movement of a tube or cannula can be limited once the tube or cannula may be advanced to a desired location.

FIG. 7B shows an enlarged detail view of the dilation introducer of FIG. 7A. The distal portions 46, 61, 32 of each of the second and third dilator tubes 45, 60, and of the access cannula 30 have generally semi-annular cross-sections. The distal portions 46, 61 of the second and third dilator tubes in the illustrated embodiment can have flattened edges, to prevent penetration into the intervertebral disc as each dilator tube is advanced.

Method of Use

FIGS. 8A-13 illustrate one embodiment of a method of performing percutaneous orthopedic surgery using the dilation introducer. With initial reference to FIG. 8A, the first dilator tube 40 can be placed through Kambin's triangle 20 until the distal portion 41 abuts or even penetrates the intervertebral disc 12. In one arrangement, the second dilator tube 45 can then be advanced over the first dilator tube 40 until the distal portion 46 of the second dilator tube abuts but does not enter the intervertebral disc 12.

As discussed above, although the illustrated embodiment shows the first and second dilator tubes as separate elements, in alternative embodiments these two tubes may be formed together as one unified dilator tube with a staggered distal portion. In still other embodiments, the first dilator tube and second dilator tube may be coupled together to form a single component. In these alternative embodiments, the unified or coupled dilator tube may be advanced until the more distal portion abuts or penetrates the intervertebral disc.

In another alternative embodiment, the first dilator tube may be omitted. Instead, a Jamshidi® needle with a removable handle or similar device may be used. In such an embodiment, the Jamshidi® needle may be first introduced to abut or enter the intervertebral disc, after which the handle may be removed. Optionally, a K-wire may be inserted into the Jamshidi® needle after it is in position either abutting or partially penetrating the intervertebral disc. The second dilator tube may then be advanced over the Jamshidi needle.

Figure 8A:
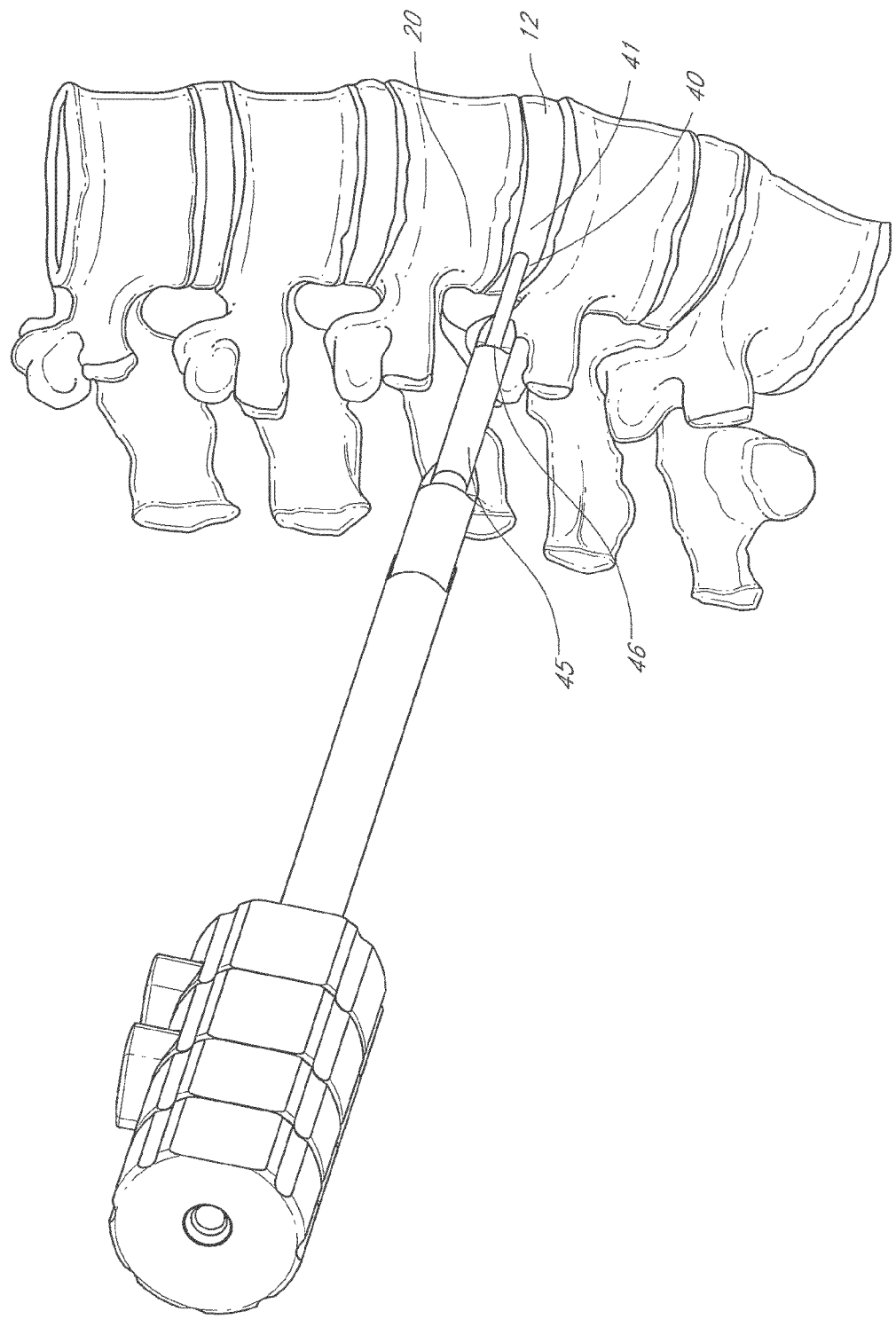
FIG. 8A is a perspective view of the dilation introducer of FIG. 7A positioned against the spine.
Figure 8B:
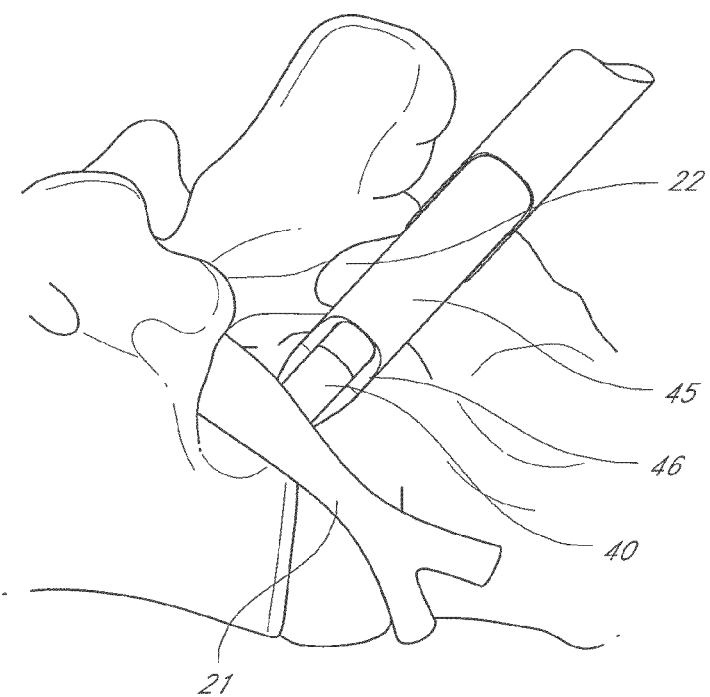
FIG. 8B is an enlarged detail view of the second dilator tube of FIG. 7A introduced over the first dilator tube of FIG. 7A.

FIG. 8B shows an enlarged detail of the second dilator tube 45 introduced over the first dilator tube 40. The distal portion 46 of the second dilator tube 45 can have a semi-annular cross-section with an opening that forms a recess with respect to the leading edge of the tube 45. The second dilator tube 45 can be oriented for advancement over the first dilator tube 40 such that the opening of the semi-annular cross-section faces the exiting nerve 21. This technique advantageously limits and/or eliminates contact with the exiting nerve. The distal portion 46 of the second dilator tube opposite the opening of the semi-annular cross-section abuts the inferior vertebrae 22. The cutting flutes (not shown) are positioned against the inferior vertebrae 22. The second dilator tube 45 may be rotated slightly back and forth, such that the cutting flutes create a recess in the inferior vertebrae 22, making room for introduction of the third dilator tube. When rotating the second dilator tube, care is taken to minimize any trauma inflicted upon the exiting nerve. Accordingly, in the illustrated embodiment, the tube 45 can be used to remove bone on a side of the tube 45 generally opposite of the nerve 21.

Figure 9:
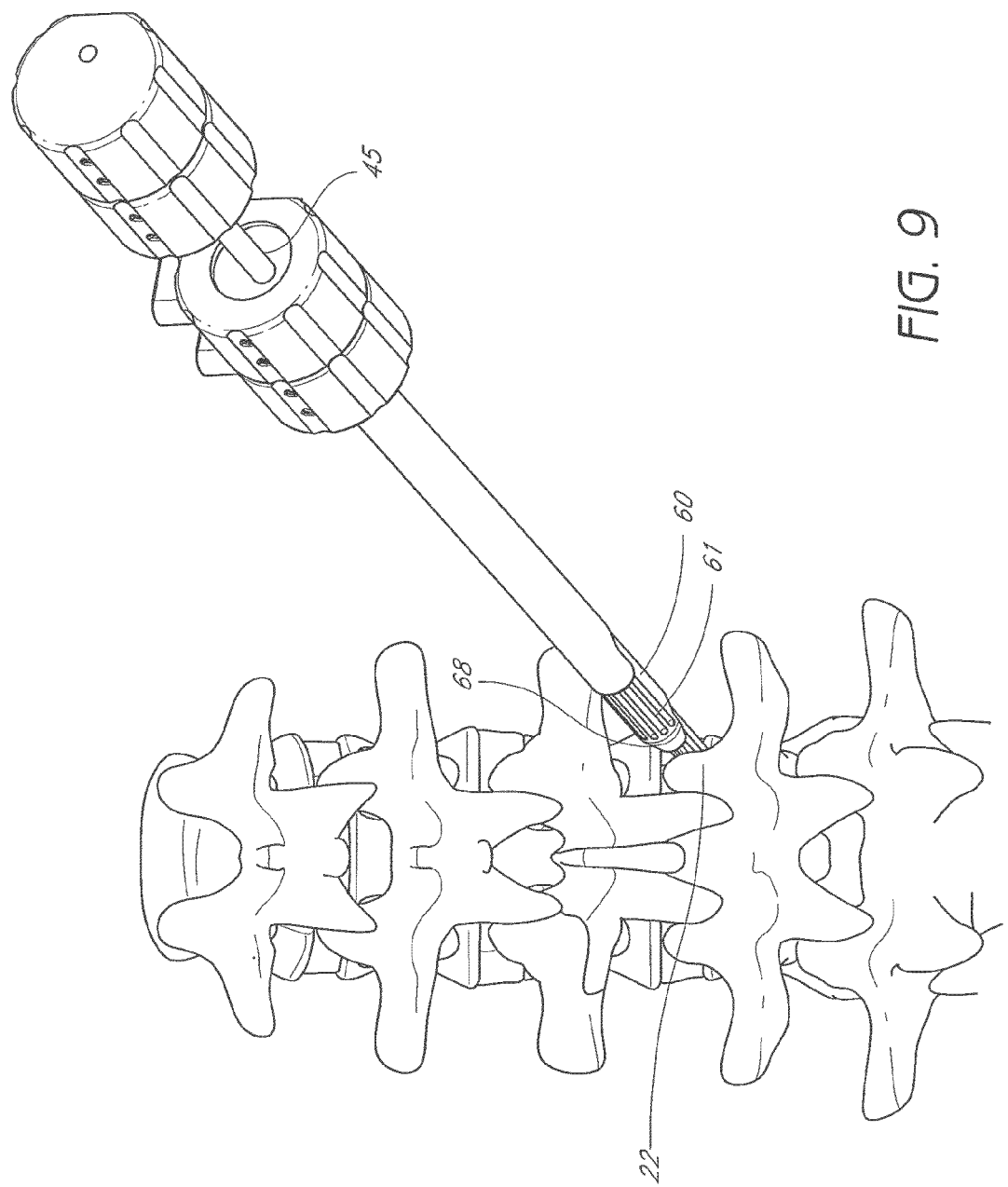
FIG. 9 is a perspective view of the dilation introducer of FIG. 7A, with the third dilator tube introduced over the second dilator tube.

With reference now to FIG. 9, the third dilator tube 60 can be introduced over the second dilator tube 45. In one arrangement, the distal portion 61 of the third dilator tube 60 abuts but does not enter the intervertebral disc. In the illustrated embodiment, a flattened edge of the distal portion can help ensure that the third dilator tube 60 does not penetrate the intervertebral disc or limit such penetration. As with the second dilator tube, the opening of the semi-annular cross-section of the distal portion of the third dilator tube can be positioned to face the exiting nerve (not shown). Contact between the third dilator tube 60 and the nerve can thereby be minimized or eliminated. The cutting flutes 68 of the third dilator tube can be positioned opposite the opening of the semi-annular cross-section, and abut the inferior vertebrae 22. The third dilator tube 60 may be rotated slightly back and forth, such that the cutting flutes create a further recess in the inferior vertebrae 22, making room for introduction of the access cannula. Again, care should be taken during the rotation of the third dilator tube to ensure that the exiting nerve is not injured thereby. Accordingly, the third dilator tube can be can be used to remove bone on a side of the tube 60 generally opposite of the nerve 21.

FIGS. 10A-D show an alternative method in which a trocar can be used in place of the first dilator tube. In some embodiments, the insertion point and access trajectory can first be determined. For example, a patient may lie face down on a surgical frame to facilitate a lordotic position of the lumbar spine. With aid of a lateral x-ray or other imaging system, a K-wire (or equivalent) can be laid beside the patient and placed to the depth of optimal insertion for the intervertebral implant. Intersection with the skin can be marked on the K-wire (or equivalent). With the aid of an anteroposterior x-ray or other imaging system, the K-wire (or equivalent) can be laid on top of the patient, aligned with the disc in a view that allows for the end plates to be parallel (e.g., Ferguson View or Reverse Ferguson, as applicable). The distance between the midline and the previously marked point on the K-wire can define the insertion point.

Figure 10A:
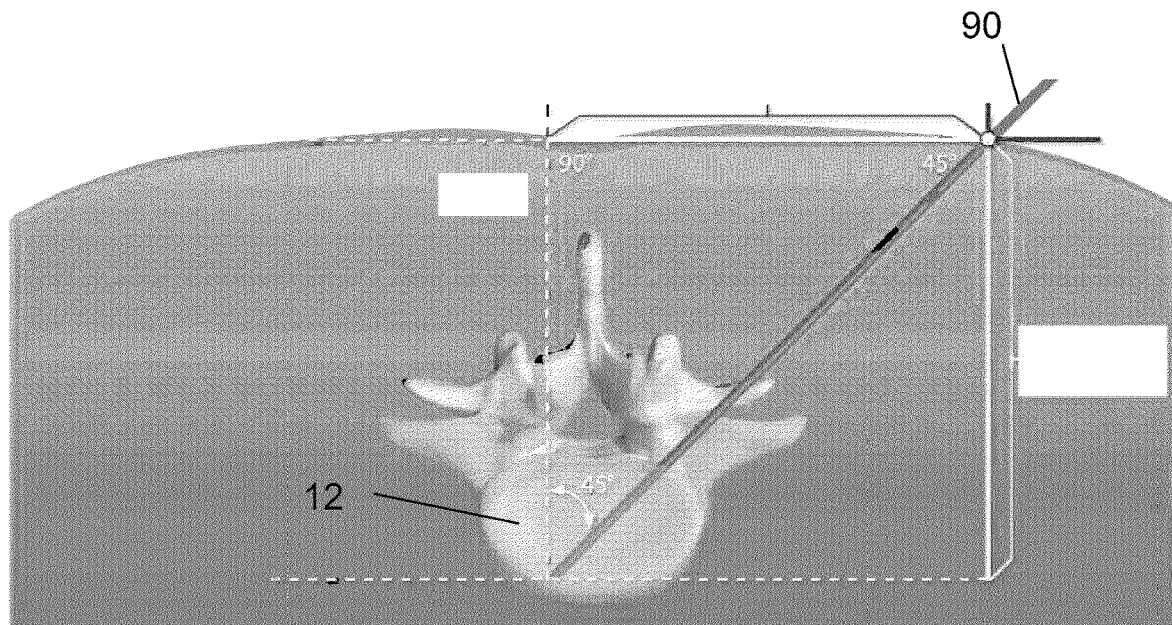
FIGS. 10A-10D show another embodiment in which a trocar is used in place of the first dilator tube.
Figure 10B:
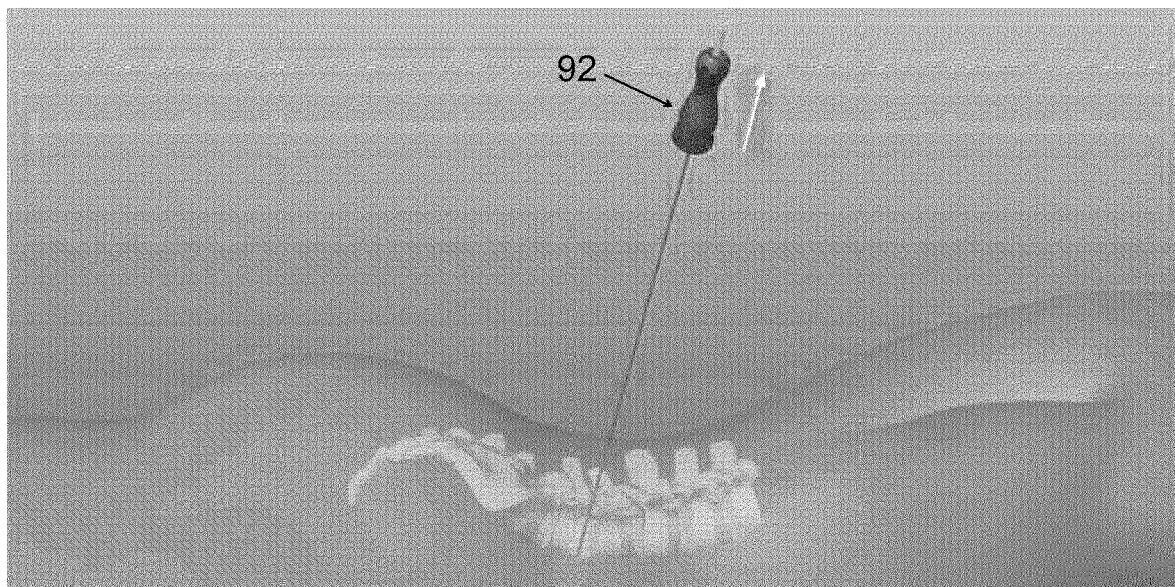
Figure 10C:
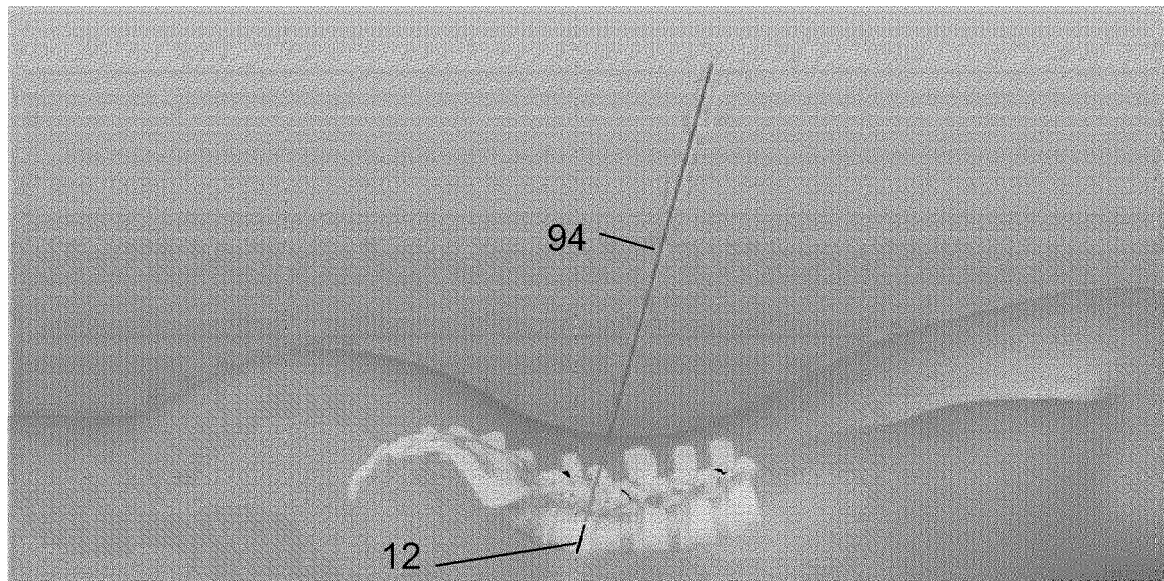
Figure 10D:
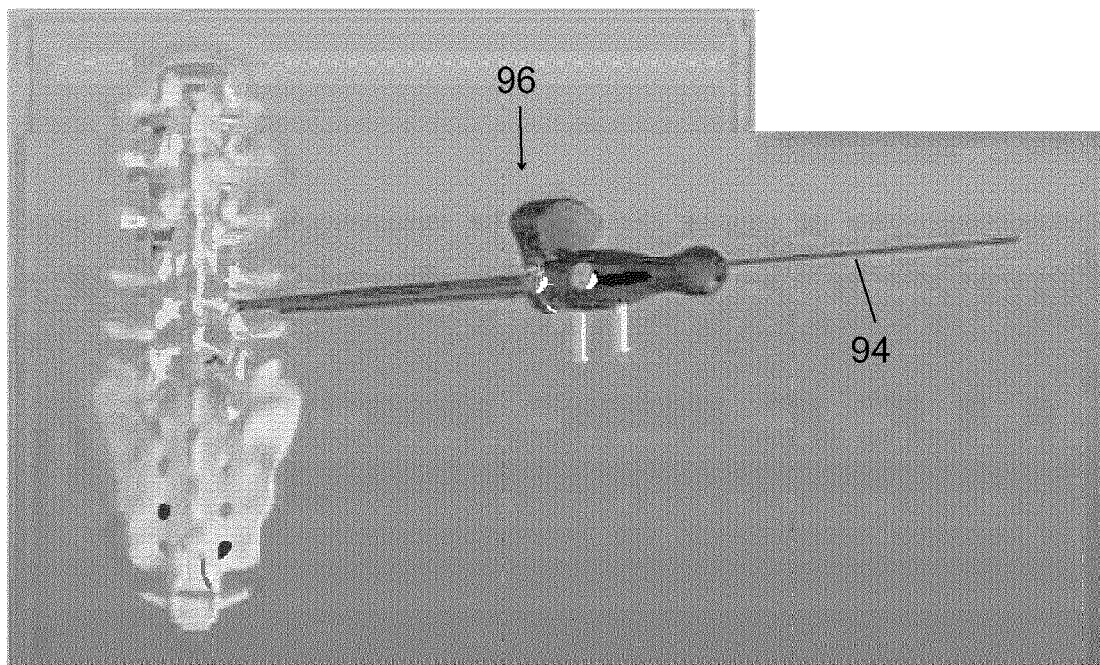

As illustrated in FIG. 10A, a small skin incision can be made defining a trajectory into the disc can be between 45 and 55 degrees. Next, a trocar 90 can be placed into the center of the disc 12 of the level to be treated, up to but not through the distal annulus. Alternatively, an 11 gauge to 18 gauge access needle can be used. As shown in FIGS. 10B-C, the inner stylet 92 of the trocar (if present) can be removed while maintaining the outer sheath 94 in place within the disc 12. Alternatively, a K-wire can be inserted into the disc and the outer sheath may be removed. Next, a dilation introducer 96 can be placed over the outer sheath 94 of the trocar (or over the K-wire, if applicable). The dilation introducer 96 can be aligned so that the smooth edges are oriented towards the exiting nerve root and the foramen. In some embodiments, the dilation introducer 96 can include at least second and third dilator tubes, each having cutting flutes adapted to perform foraminoplasty for improved access to the disc space. In some embodiments, the dilation introducer 96 can function substantially as described elsewhere herein, except that the trocar 90 has replaced the first dilator tube. In some embodiments, the second dilator tubes may be rotated within +/−45 degrees around the longitudinal axis so that the cutting flutes do not contact the exiting nerve.

FIG. 11 shows the access area before and after the second and third dilator tubes 45, 60 are rotated to create a recess in the inferior vertebrae 22. The area 70 in the left image demarcated by a dashed line is the portion of bone that can be removed by the second and third dilation tubes 45, 60. This foraminoplasty permits the access cannula to be introduced without disturbing the exiting nerve 21. The method described is not limited by the precise location of the recess shown in FIG. 11. In general, a recess may be formed anywhere along the superior border of the inferior vertebrae 22, in order to provide improved access for a dilation introducer.

Figure 12A:
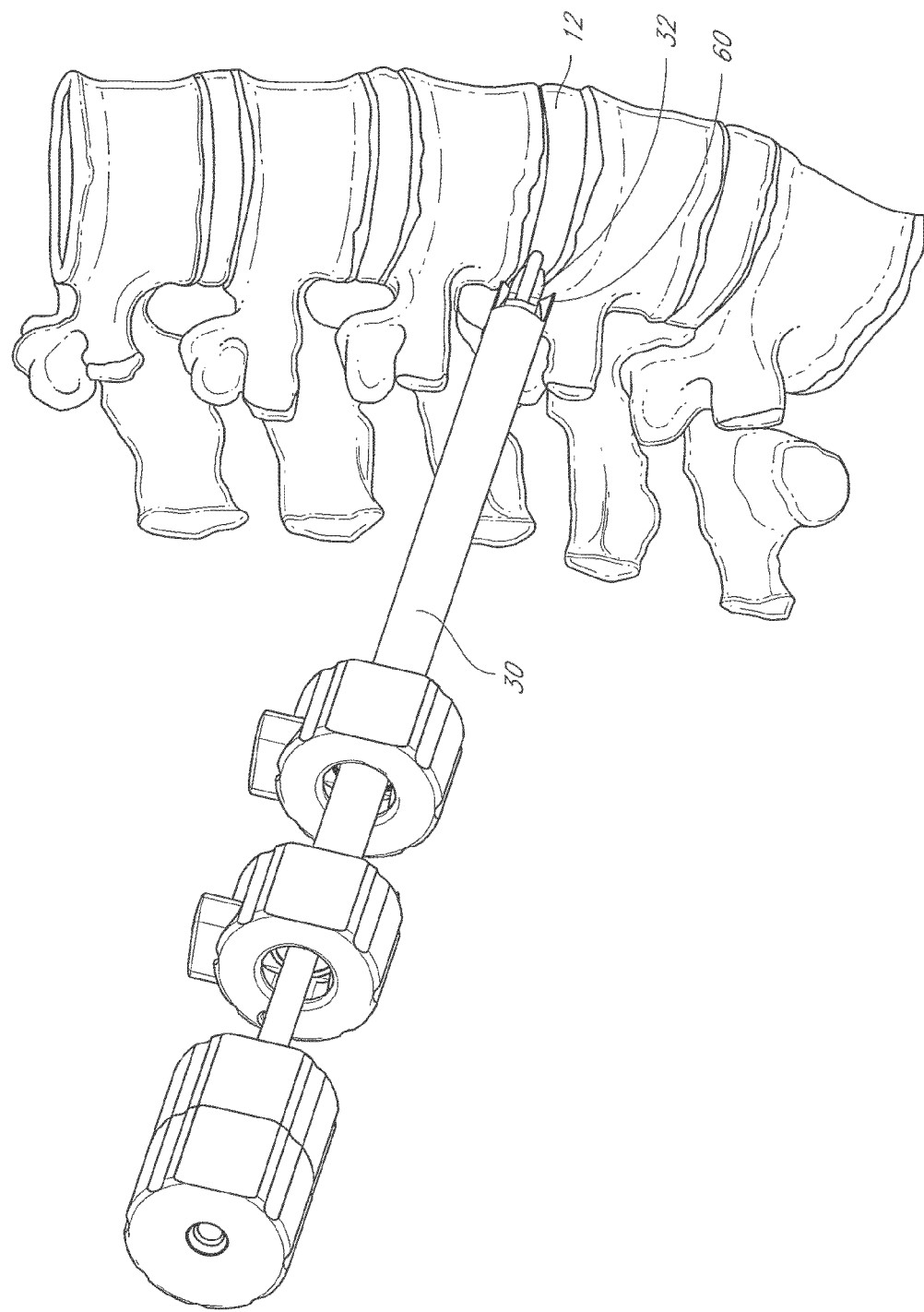
FIG. 12A is a perspective view of the dilation introducer of FIG. 7A, with the access cannula introduced over the third dilator tube.

FIG. 12A shows the access cannula 30 introduced over the third dilator tube 60. The distal portion 32 of the access cannula 30 abuts but does not enter the intervertebral disc 12. In one embodiment, the distal portion 32 can be equipped with flattened edges to guard against insertion into the intervertebral disc. As with the second and third dilator tubes 45, 60, the opening of the semi-annular cross-section of the distal portion 32 of the access cannula 30 can be positioned initially to face the exiting nerve (not shown). Contact between the access cannula 30 and the exiting nerve can thereby be minimized during insertion.

Figure 12B:
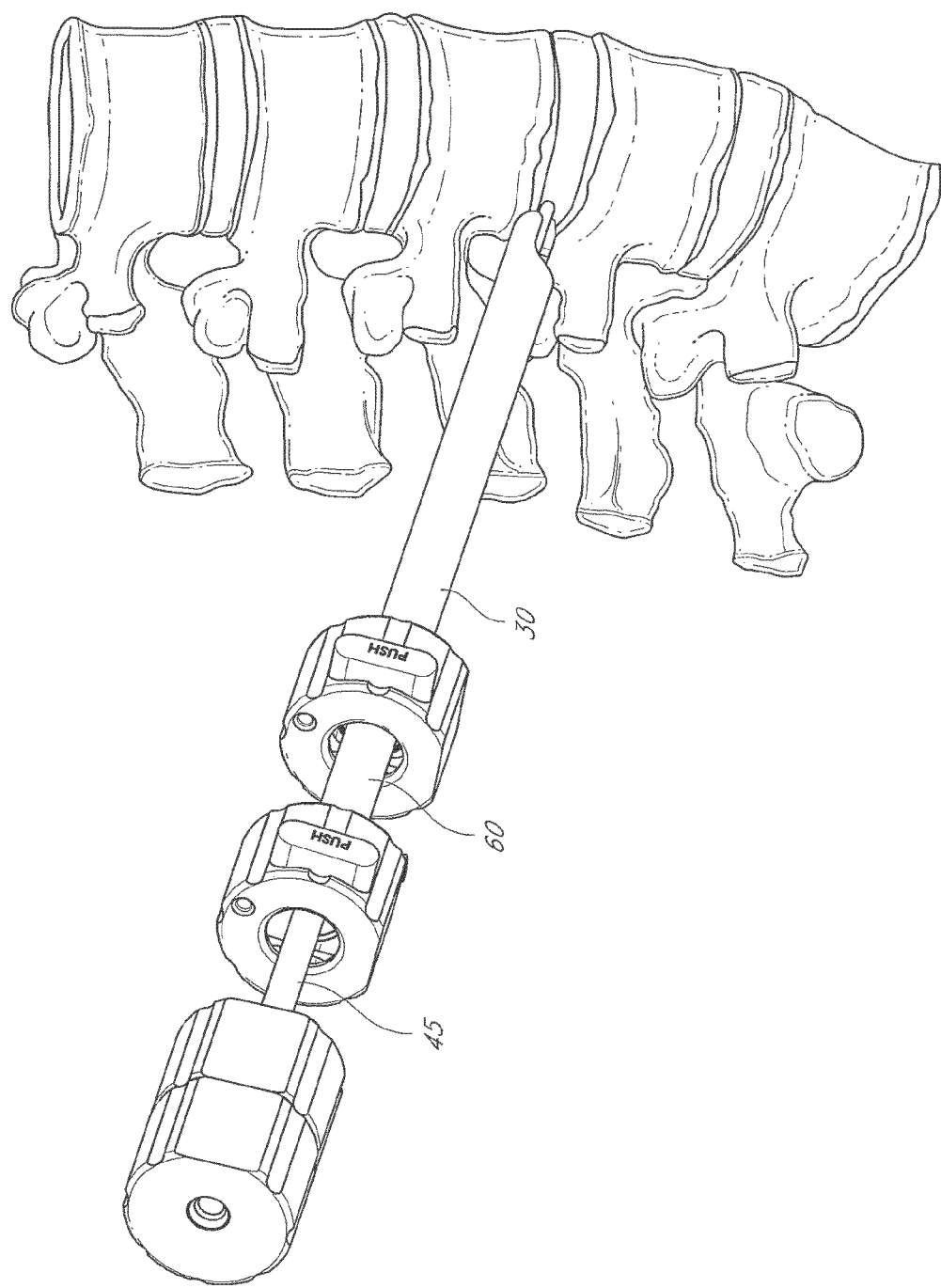
FIG. 12B is a perspective view of the dilation introducer of FIG. 7A, with the access cannula rotated to protect the exiting nerve.

As can be seen in FIG. 12B the access cannula 30 can then be rotated such that the opening of the semi-annular cross-section faces opposite the exiting nerve (not shown). Since, unlike the second and third dilator tubes 45, 60, the outer surface of the access cannula is smooth, trauma to the exiting nerve may be minimized during this rotation.

Figure 12C:
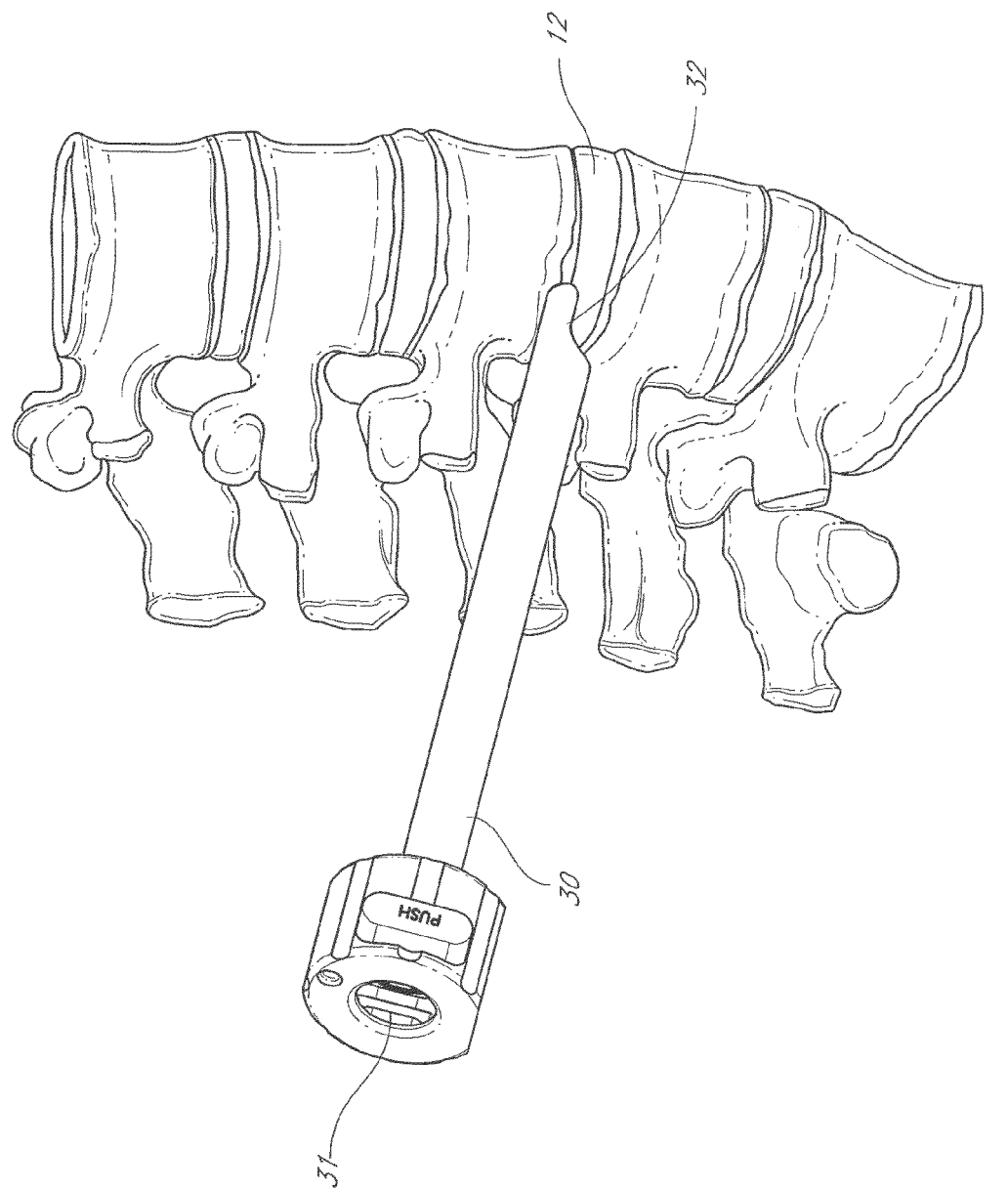
FIG. 12C is a perspective view of the dilation introducer of FIG. 7A, with the first, second, and third dilator tubes removed, while the access cannula remains in place.

Referring now to FIG. 12C, once the access cannula 30 is in position, which in one embodiment comprising until the distal portion 32 abuts the intervertebral disc 12, the cannula 30 can be rotated so that the opening of the semi-annular cross-section faces opposite the exiting nerve (not shown), the first, second, and third dilator tubes 40, 45, 60 may be removed. In one embodiment, rotation of the cannula 30 can gently move the nerve away from the access site while also protecting the nerve as tools and devices may be inserted through the cannula 30. The access cannula 30 can then provide an open lumen 31 through which surgical tools can be introduced to the site of the intervertebral disc 12. As noted above, the positioning of the access cannula 30 protects the exiting nerve (not shown) from coming into contact with any of the surgical tools.

Figure 13:
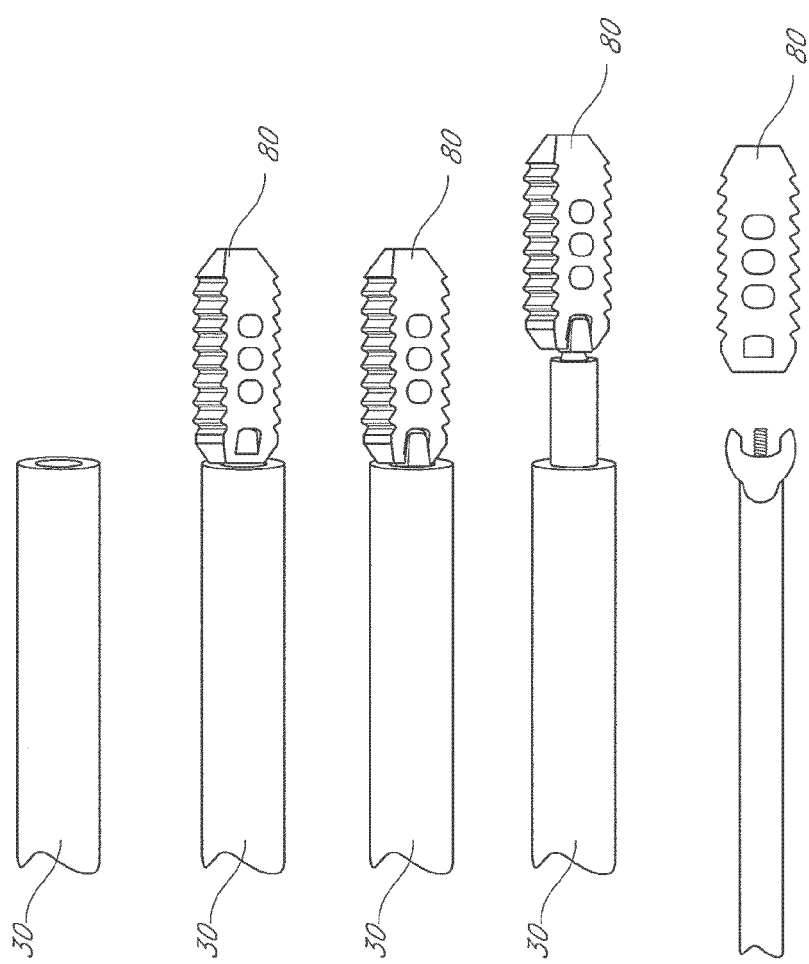
FIG. 13 is a plan view of an intervertebral implant for delivery through the access cannula.

A example of a surgical tool for use through the access cannula is depicted in FIG. 13. The intervertebral implant 80 may be introduced through the access cannula 30, and released once in position. Although a particular intervertebral implant is shown here, one of skill in the art will readily understand that any number of surgical tools may be introduced through the access cannula. For example, surgical tools to be inserted through the access cannula may include, without limitation, discectomy tools, tissue extractors, bone graft insertion tools, rasps, forceps, drills (e.g,. trephine), rongeurs, curettes, paddle distractors, mechanical distractors, lasers, automated probes, manual probes, and plasma wands. In one embodiment of use, an opening in the disc annulus can be formed and a portion of the disc can be removed using tools advanced through the access cannula 30. The disc space can be distracted (e.g,. using paddle distractors) before and/or after the implant 80 and/or different or additional interbody devices are inserted through the access cannula 30 and placed between the vertebral bodies to maintain spacing. In some embodiments the disc nucleus or portions thereof is removed while leaving the disc annulus. Bone graft and/or other materials such as, for example, bone morphogenetic proteins (BMPs) can be placed between the vertebrae before, while or after positioning the implant. Fusion can then occur between the vertebrae. In some procedures, fusion can be augmented with other fixation devices such as, for example, pedicle screws and rod constructions, transfacet and transpedicle screws, interbody spacers, rods, plates and cages, which can be used to stabilize a pair of vertebral bodies together. For example, in one arrangement, the fusion is augmented by one or more posterior fixation devices (e.g transfacet and transpedicle screws and/or pedicle screws and rods and/or spinous process spacers). In such a manner, the entire fusion procedure can be done from a posterior position and preferably in a minimally invasive (e.g., percutaneous manner). For example, in one embodiment, the above described procedure is used in combination with the transfacet-pedicular implant system sold by Intervention Spine, Inc. under the trade name PERPOS®, such a system is also described in U.S. Pat. Nos. 7,998,176 and 7,824,429, the entirety of which are hereby incorporated by reference herein.

FIGS. 14-20D illustrate another aspect of a dilation introducer 1100 that can be used to perform percutaneous orthopedic surgery. The dilation introducer in this embodiment is similar in some respects to that described above. As will be described in detail below, the proximal portion of the dilation introducer 1100 differs significantly from that of the dilation introducer 100 described above. The dilation introducer 1100 in the illustrated embodiments can comprise an access cannula 130, and a first, second and third dilator tubes 140, 145, 160. While the illustrated embodiment includes first, second and third dilator tubes 140, modified embodiments can include more or less dilator tubes and/or dilator tubes with modified features. It is also anticipated that in some embodiments, the access cannula 130 can be eliminated from the introducer or modified.

Figure 14A:
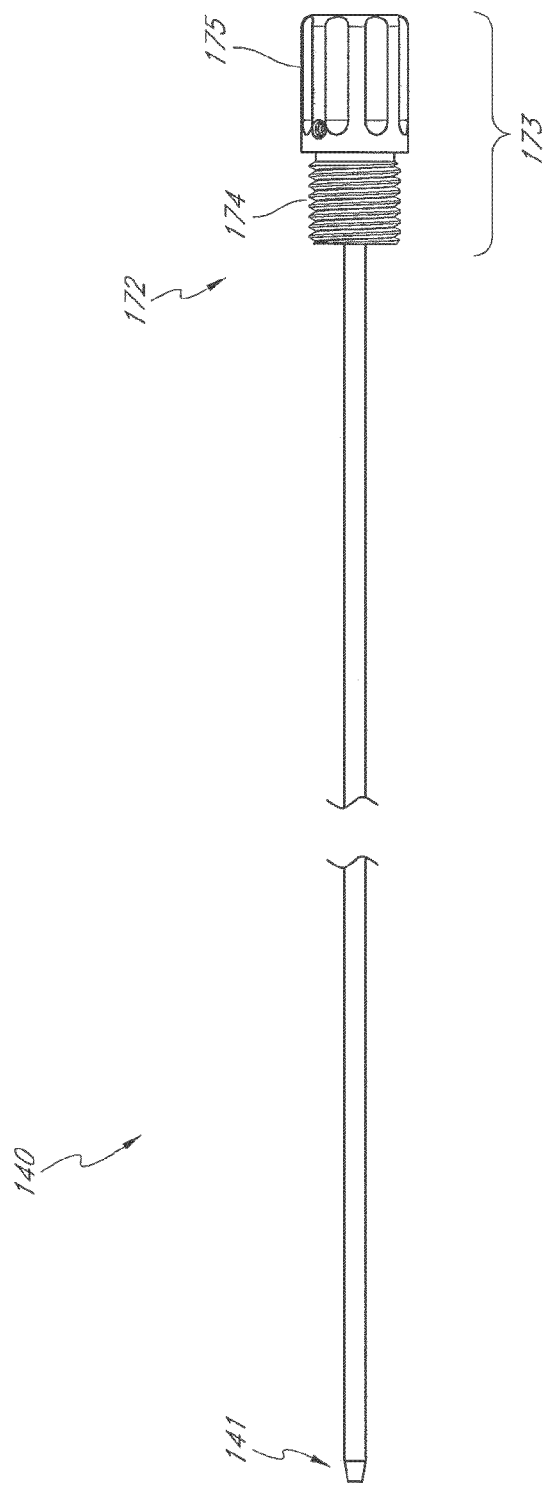
FIG. 14A is a plan view of another embodiment of a first dilator tube.
Figure 14C:
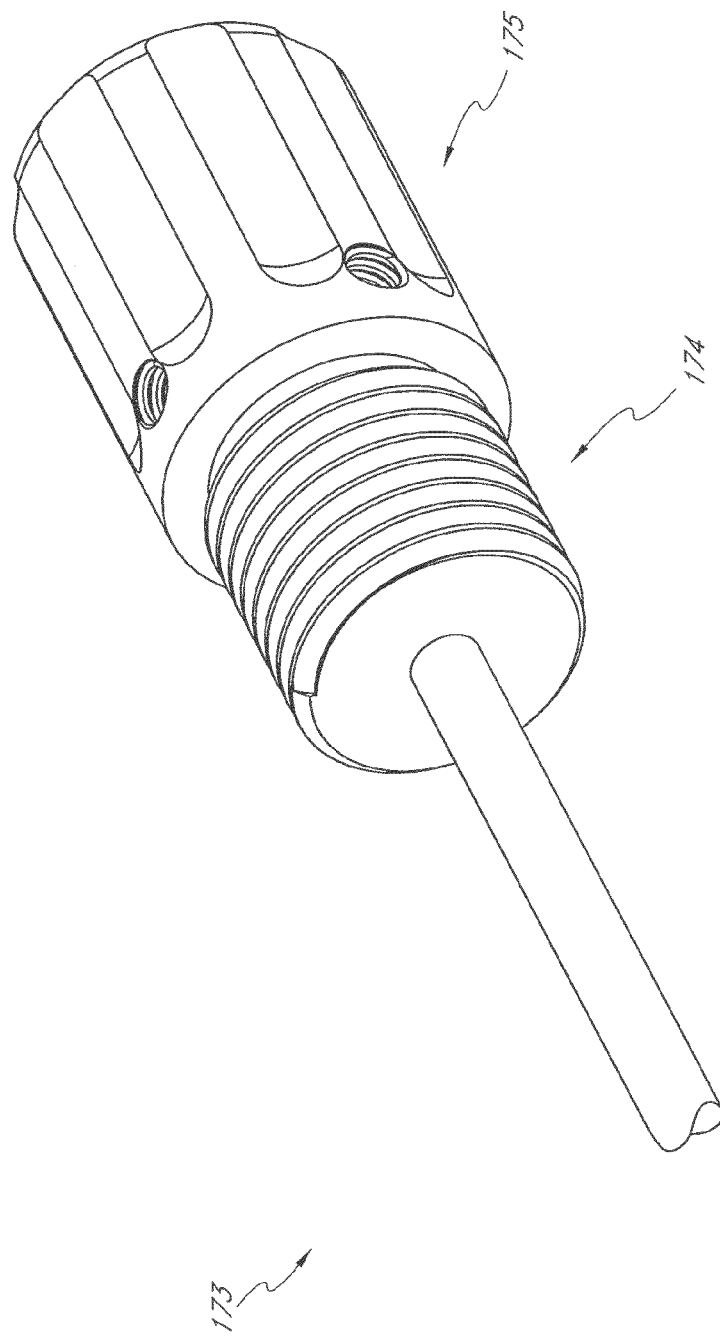
FIG. 14C is an enlarged detail view of the proximal end of the first dilator tube shown in FIG. 14A.

FIGS. 14A to 14C illustrate an embodiment of the first dilator tube 140 of the dilation introducer 1100. As shown, in the illustrated embodiment, the first dilator tube 140 may have distal portion 141, an outer radius 142 and a first longitudinal lumen 143. The outer radius 142 can be centered around first longitudinal axis 144. The distal portion 141 may include a tapered tip 171 of the dilator tube. The proximal portion 172 of the first dilator tube may include a first proximal head 173, with a threaded portion 174 distal to the gripping portion 175. In some embodiments, the longitudinal lumen 143 extends through the proximal head 173, such that a guidewire or K-wire may be introduced through the proximal head 173 and the dilator tube 140.

Figure 15A:
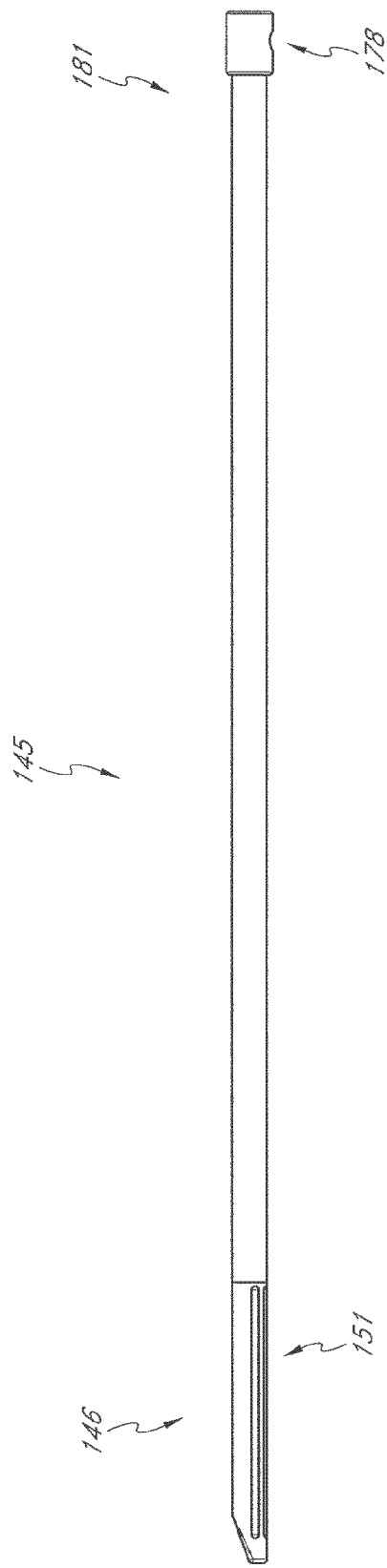
FIG. 15A is a plan view of another embodiment of a second dilator tube.
Figure 15B:
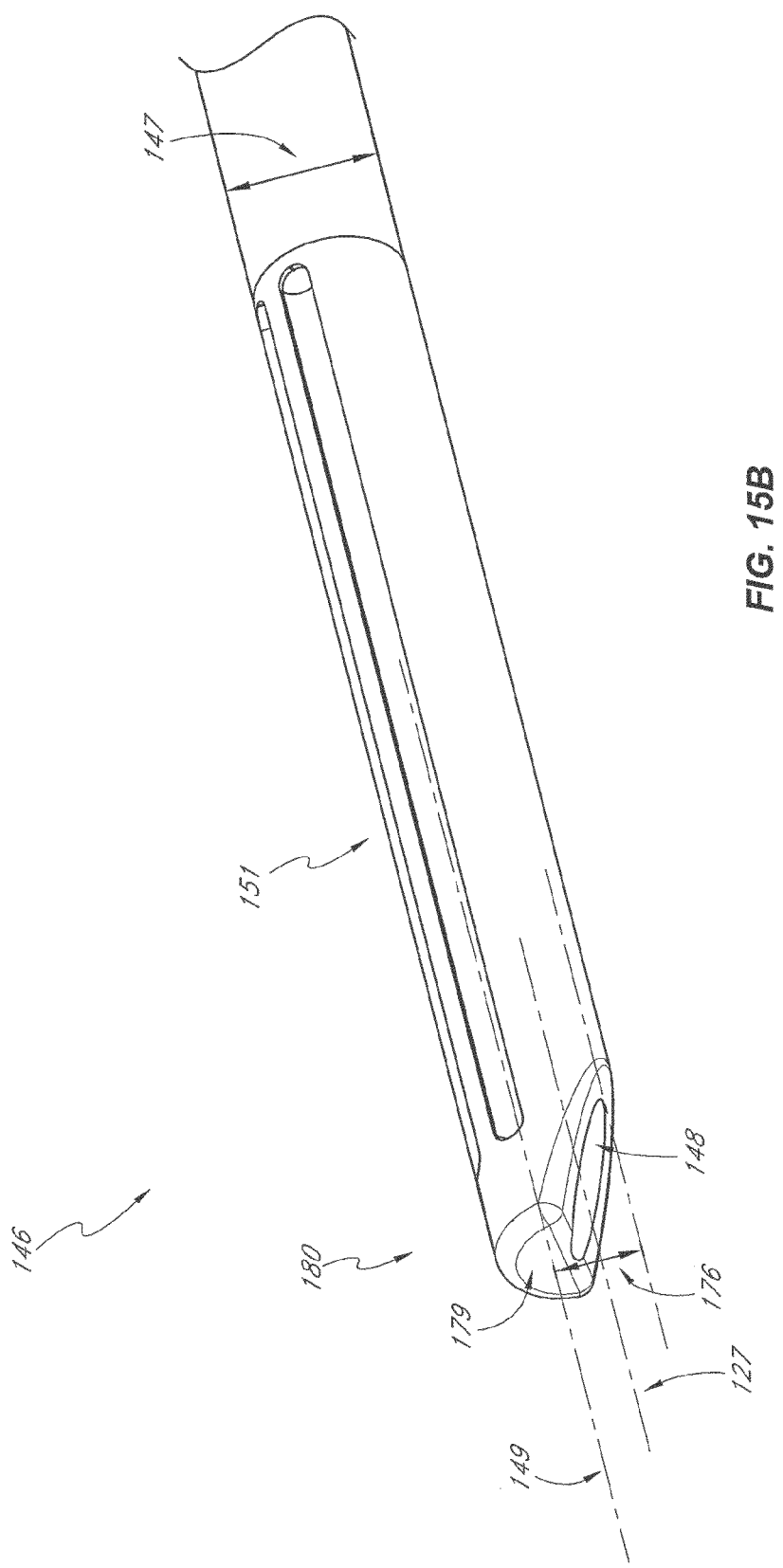
FIG. 15B is an enlarged detail view of the distal end of the second dilator tube shown in FIG. 15A.
Figure 15C:
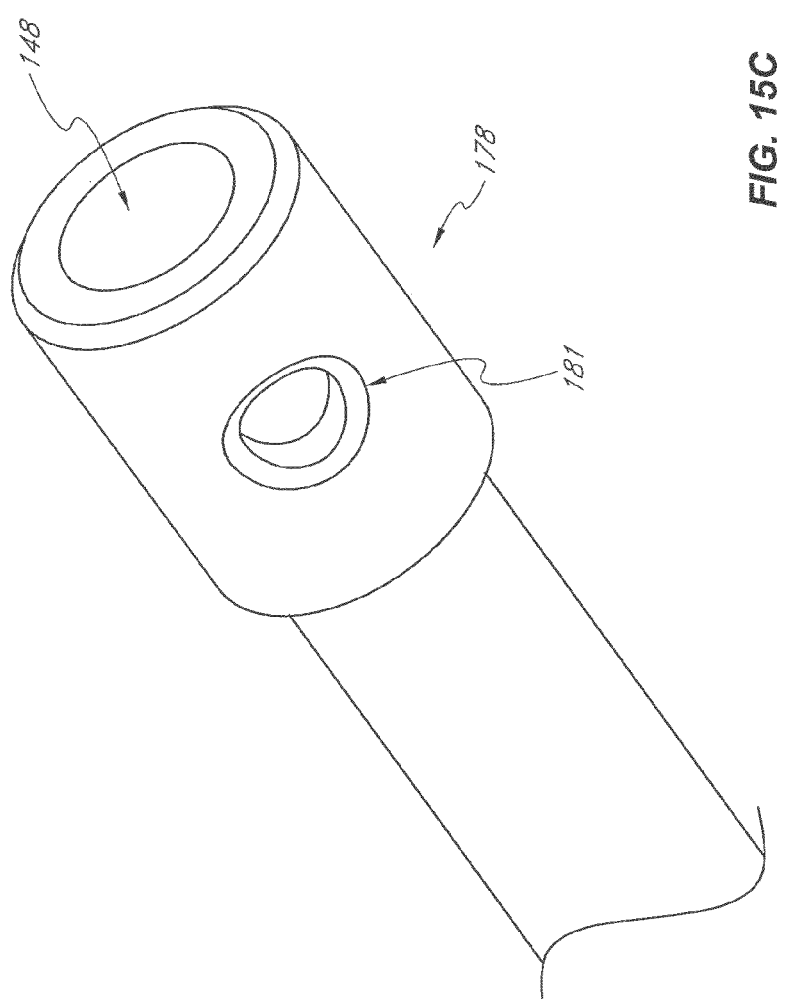
FIG. 15C is an enlarged detail view of the proximal end of the second dilator tube shown in FIG. 15A.

FIGS. 15A to 15C illustrate an embodiment of the second dilator tube 145. In the embodiment shown the second dilator tube has a distal portion 146, and an outer radius 147. The outer radius may be centered around a second longitudinal axis 149. The second dilator tube includes a second longitudinal lumen 48 with an inner radius 176. The outer radius 142 of the first dilator tube may be nearly equivalent to the inner radius 176 of the second dilator tube, such that the first dilator tube 140 can be slidably received within the second longitudinal lumen 148. The proximal portion 177 of the second dilator tube includes a collar 178.

FIG. 15B shows an enlarged detail view of the distal portion of the second dilator tube 145. The distal portion 146 of the second dilator tube may include a flattened edge 179. This flattened edge 179 advantageously prevents the second dilator tube 145 from penetrating the intervertebral disc 112. The tip 180 of distal portion 146 can have a generally semi-annular cross-section, configured such that when the first dilator tube 140 is received within the second dilator tube 145, the outer radial surface of the first dilator tube 140 is partially exposed at the distal tip 180 of the second dilator tube 145. The opening of the generally semi-annular cross-section of the second dilator tube can be oriented opposite the second longitudinal axis 149 with respect to the longitudinal axis 127 of the second longitudinal lumen.

When the first dilator tube 140 is received within the second dilator tube 145, the longitudinal axis 127 of the second longitudinal lumen is essentially aligned with the first longitudinal axis 144. Additionally, the second dilator tube 145 can include cutting flutes or ridges 151 on one side, located opposite the opening of the generally semi-annular cross-section of the second dilator tube 145. In other embodiments, the cutting flutes 151 may be replaced with a coarse surface (e.g., knurling, sharp edges, abrasive members, etc.) which, when rotated or slid (e.g., back and forth) against bone, will create a recess therein. As noted above, other mechanisms for removing bone can be used, and the cutting flutes are shown here by way of example only. As can be seen in FIG. 15B, the inner lumen 148 of the second dilator tube 145 can be off-center. In this configuration, the cutting flutes 151 are further from the axis of rotation than the side opposite the cutting flutes. This is particularly advantageous for performing foraminoplasty while protecting the exiting nerve, as will be discussed in more detail below.

FIG. 15C shows an enlarged detail view of the proximal portion 177 of the second dilator tube 145. The collar 178 includes an aperture 181 which may be used in conjunction with the third dilator tube, as described in detail below. In alternative embodiments, the aperture 181 may be instead replaced with a circumferentially oriented groove.

FIGS. 16A to 16D illustrate and embodiment of the third dilator tube 160, which can be configured to be slidably introduced over the second dilator tube 145. The third dilator tube 160 can include a distal portion 161, a third outer radius 162 centered around a third longitudinal axis 163, and a third longitudinal lumen 164 having a third inner radius 165 centered around longitudinal axis 169 that runs parallel to and laterally offset from the third longitudinal axis 163. The third lumen 164 can be configured to removably receive the second dilator tube 145 for slidable movement within the third lumen 164. In such a configuration, the second longitudinal axis 149 essentially aligns with the longitudinal axis 169 of the inner lumen 164 of the third dilator tube 160. The proximal portion 182 includes a handle assembly 183.

Figure 16A:
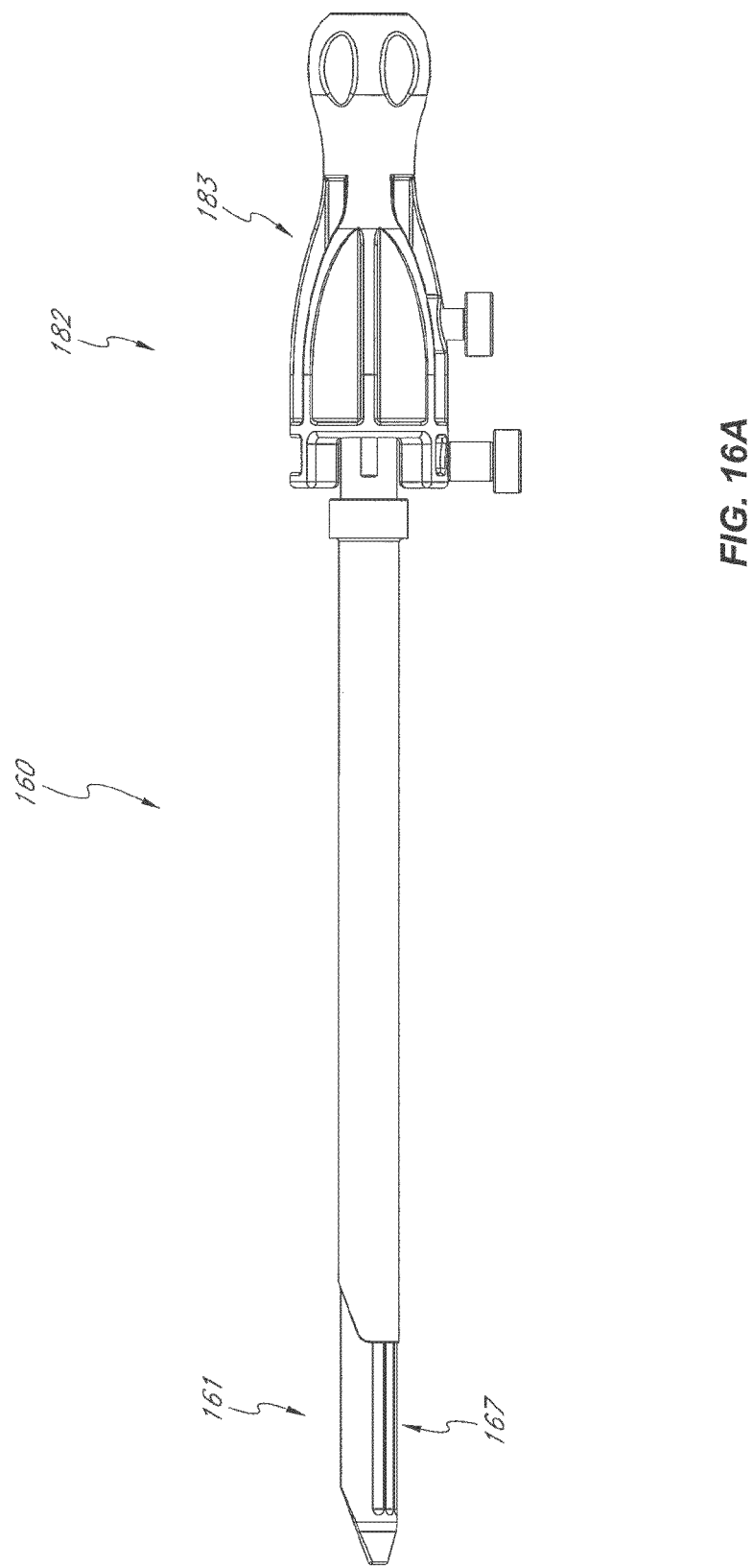
FIG. 16A is a plan view of another embodiment of a third dilator tube.
Figure 16B:
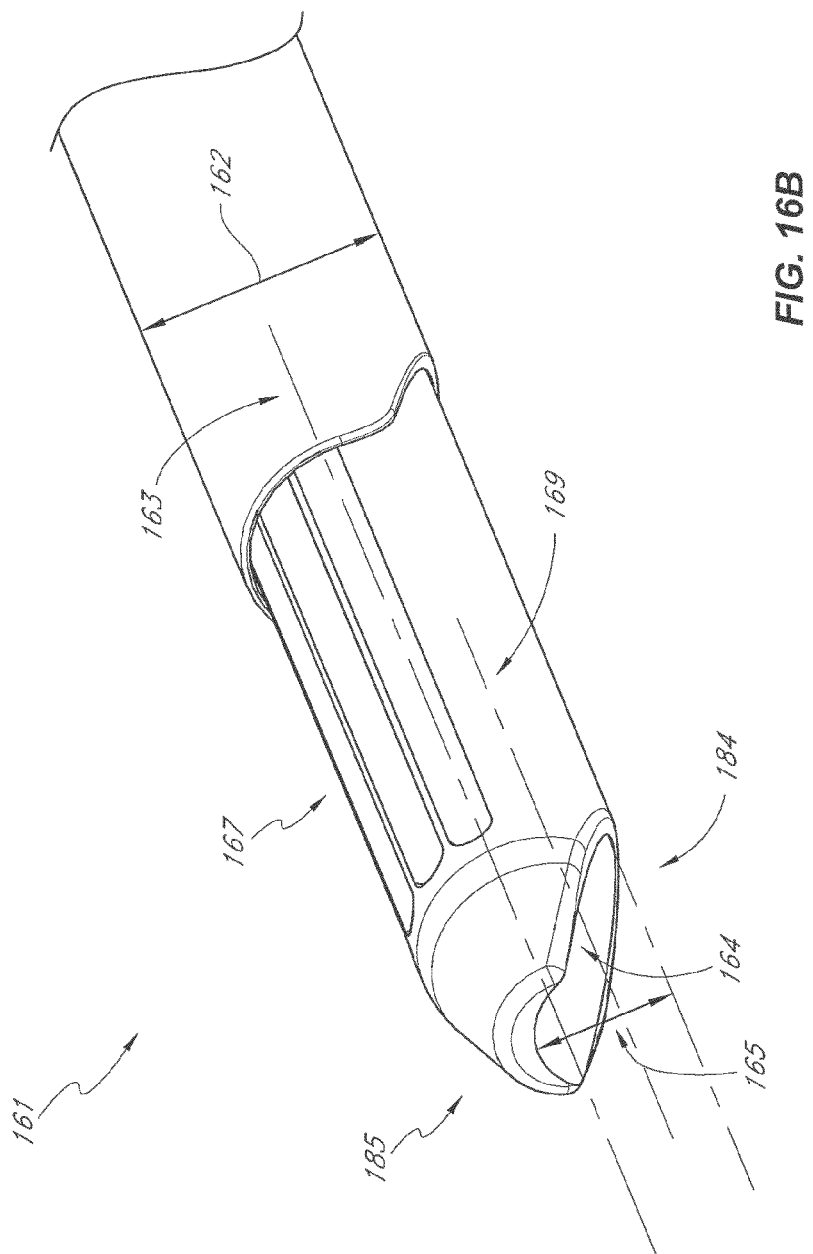
FIG. 16B is an enlarged detail view of the distal end of the third dilator tube shown in FIG. 16A.

FIG. 16B shows an enlarged detail view of the distal portion of the third dilator tube of FIG. 16A. The distal portion 161 of the third dilator tube may include a flattened edge 185. This flattened edge 185 advantageously prevents the third dilator tube 160 from penetrating the intervertebral disc 112. The tip 184 of the distal portion 161 has a generally semi-annular cross-section, and cutting flutes 167 for reaming bone located opposite the opening of the semi-annular cross-section. As with the second dilator tube, in other embodiments the cutting flutes may be replaced or used in combination with a coarse or other cutting or abrading surface which, when rotated or slid against bone, will create a recess therein. As can be seen in FIG. 16B, the longitudinal lumen 164 of the third dilator tube 160 may be off-center. In this configuration, the cutting flutes 167 are further from the axis of rotation than the side opposite the cutting flutes. This is particularly beneficial for performing foraminoplasty while protecting the exiting nerve, as will be discussed in more detail below.

Figure 16D:
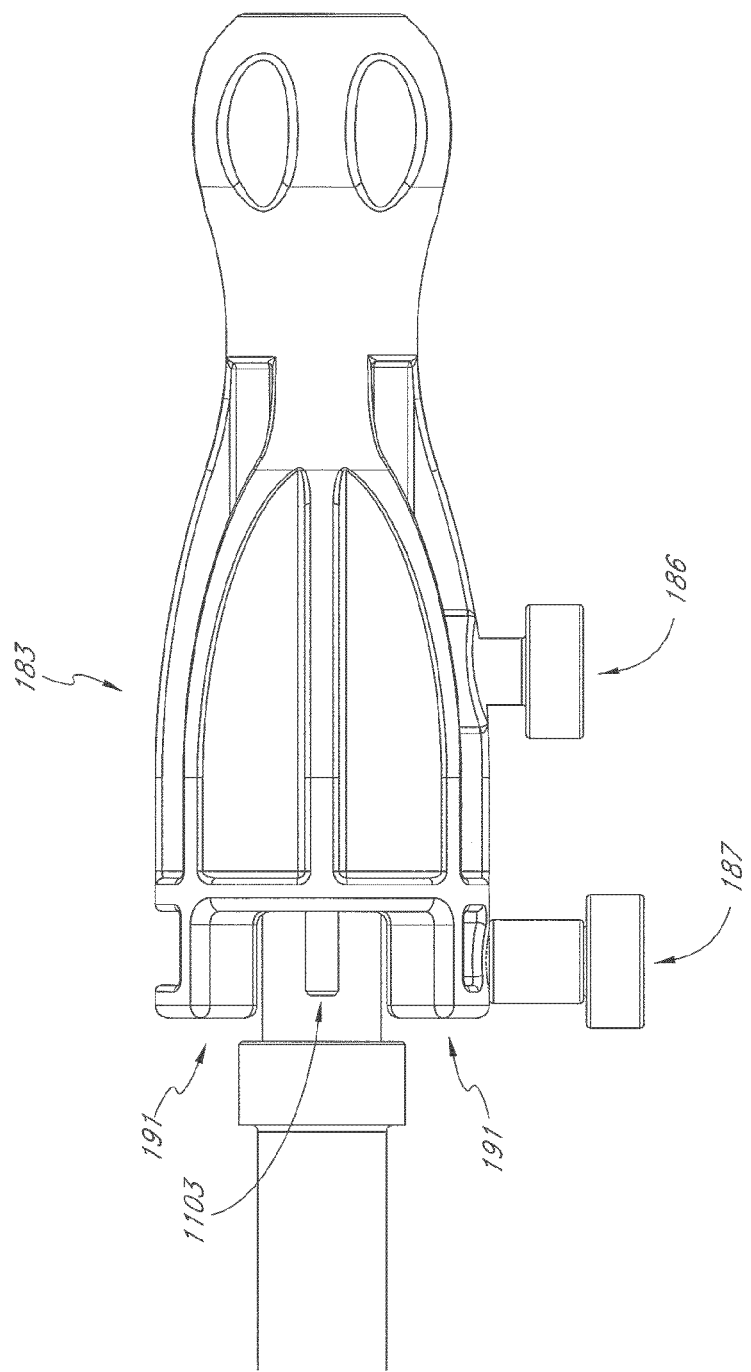

FIGS. 16C and 16D show enlarged detail views of the proximal portion 182 of the third dilator tube 160. The proximal portion 182 includes a handle assembly 183. A first latching button 186 may be configured for constraining the movement of the third dilator tube relative to the second dilator tube, as described in more detail below. In various embodiments, the latching button 186 may constrain slidable movement, rotational movement, or both. A second latching button 187 may be located distal the first latching button 186, and may be configured to constrain the movement of the access cannula relative to the third dilator tube, as described in more detail below. The distal end of the handle assembly 183 includes an overhanging lip 191 into which the proximal grip 136 of the access cannula can be removably received. When the proximal grip 136 of the access cannula is received within the overhanging lip 191, the locking pin 1103 slides within the locking pinhole 1104 on the proximal grip 136 of the access cannula, thereby restricting rotational movement of the access cannula relative to the third dilator tube. In various embodiments, the locking pinhole may be omitted, permitting rotation of the access cannula 130 relative to the third dilator tube 60.

Figure 17A:
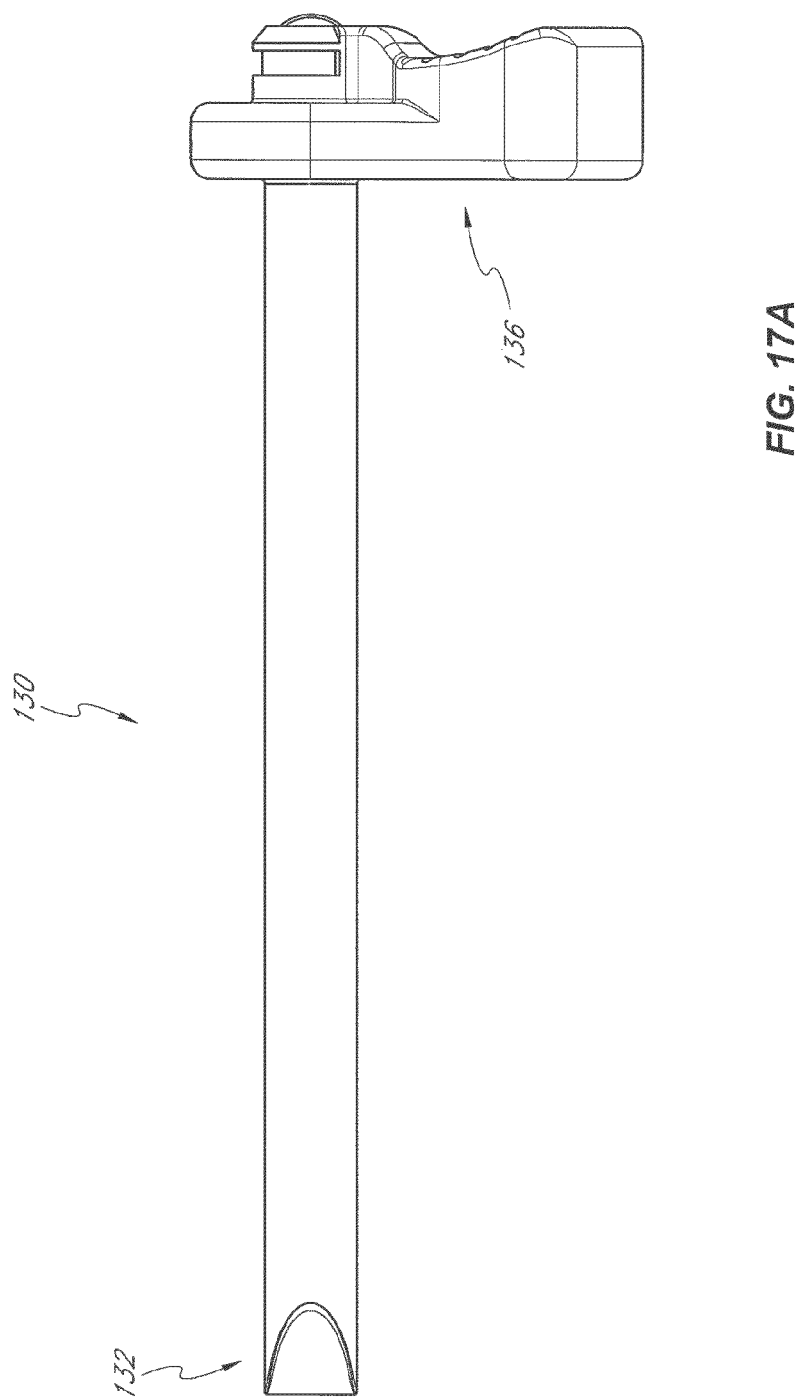
FIG. 17A is a plan view of another embodiment of an access cannula.
Figure 17B:
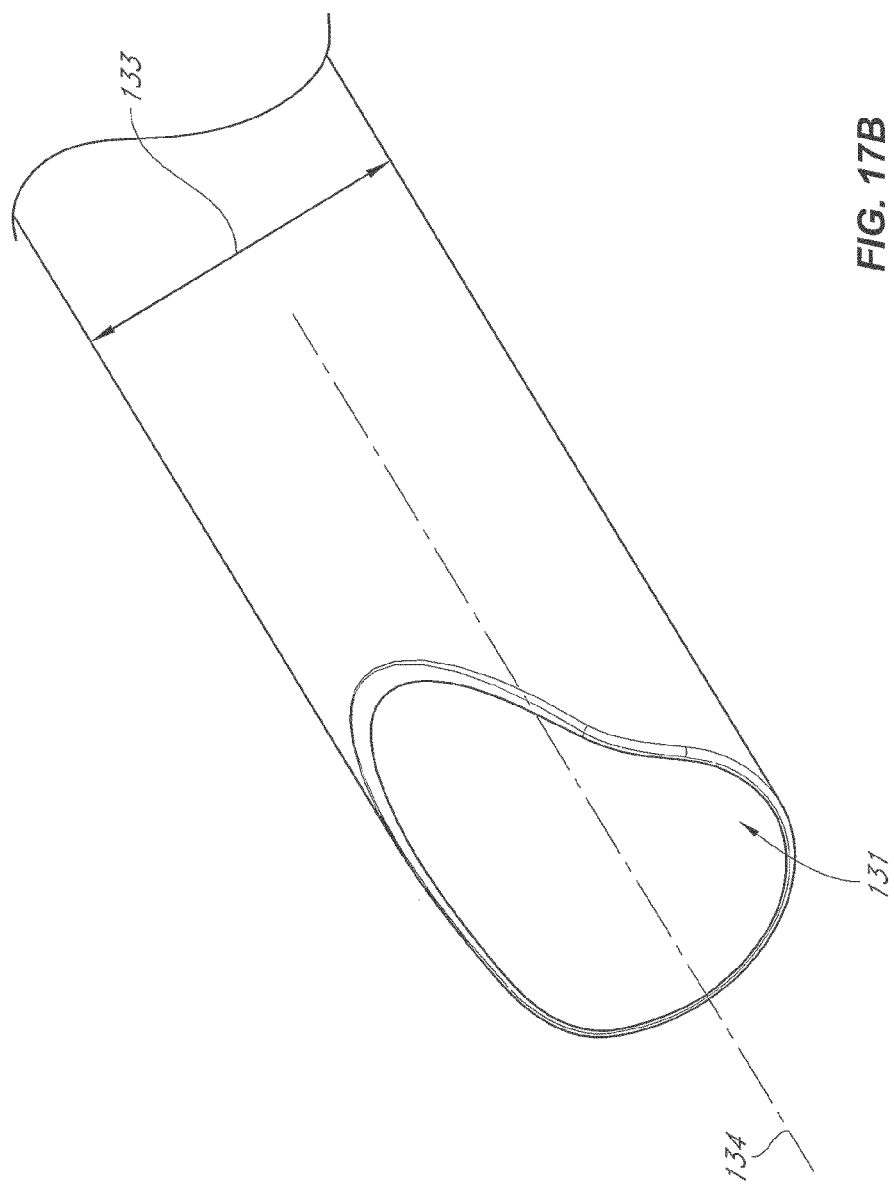
FIG. 17B is an enlarged detail view of the distal end of the access cannula shown in FIG. 17A.
Figure 17C:
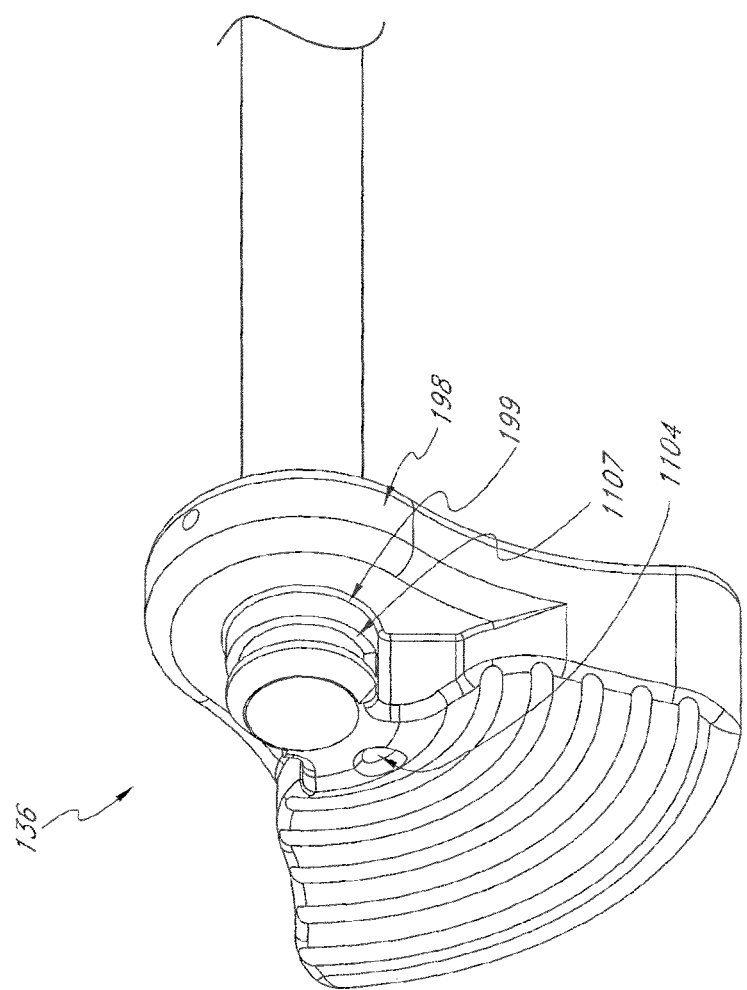
FIG. 17C is an enlarged detail view of the proximal end of the access cannula shown in FIG. 17A.

FIGS. 17A to 17C illustrate an embodiment of the access cannula 130, which can be configured to be introduced over the third dilator tube 145. The access cannula 130 has a distal portion 132, a fourth longitudinal axis 134, and a fourth longitudinal lumen 131 having a fourth inner radius 135. The access cannula 130 may be configured to removably receive the third dilator tube (not shown) for slidable movement within the third lumen. A handle 136 allows for rotation of the access cannula 130.

FIG. 17B shows an enlarged detail view of the distal portion of the access cannula of FIG. 17A. The distal portion 132 can have a generally semi-annular cross-section. In the embodiment shown, the fourth longitudinal lumen may be centered with respect to the outer radius of the access cannula, in contrast to the second and third dilator tubes. In other embodiments, however, the access cannula may also have a longitudinal lumen that is off-center with respect to the outer radius. In yet another embodiment, the access cannula need not be limited to a cylindrical outer surface. The outer surface could, for instance, have an elliptical, polygonal, or other cross-sectional shape.

FIG. 17C shows an enlarged detail view of the proximal portion 193 of the access cannula of FIG. 17A. The proximal grip 136 may provide additional leverage while advancing the access cannula over the third dilator tube. The proximal grip 136 includes a larger diameter portion 198 and a smaller diameter portion 199. The smaller diameter portion 199 includes a circumferential channel 1107 for use in interlocking with the third dilator tube, as discussed in detail below. A locking pinhole 1104 can receive the locking pin 1103 on the third dilator tube, thereby restraining rotational movement of the access cannula 160 relative to the third dilator tube 145.

Figure 18A:
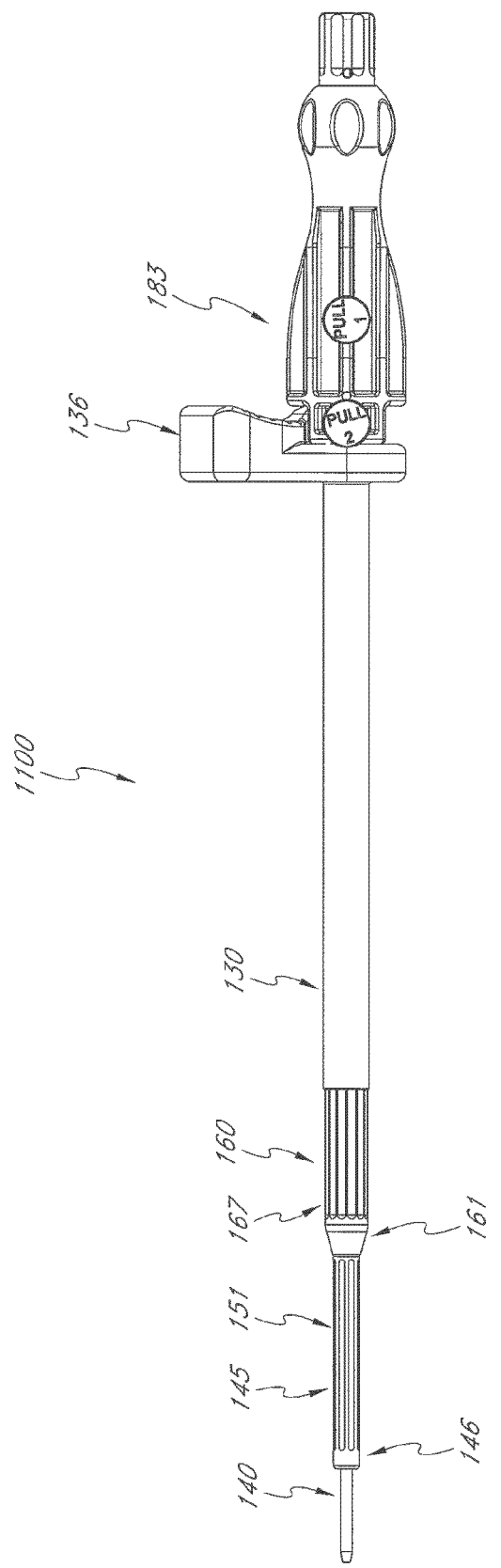
FIG. 18A is a plan view of another embodiment of a dilation introducer comprising the first dilator tube of FIG. 14A, the second dilator tube of FIG. 15A, the third dilator tube of FIG. 16A, and the access cannula of FIG. 17A.
Figure 18B:
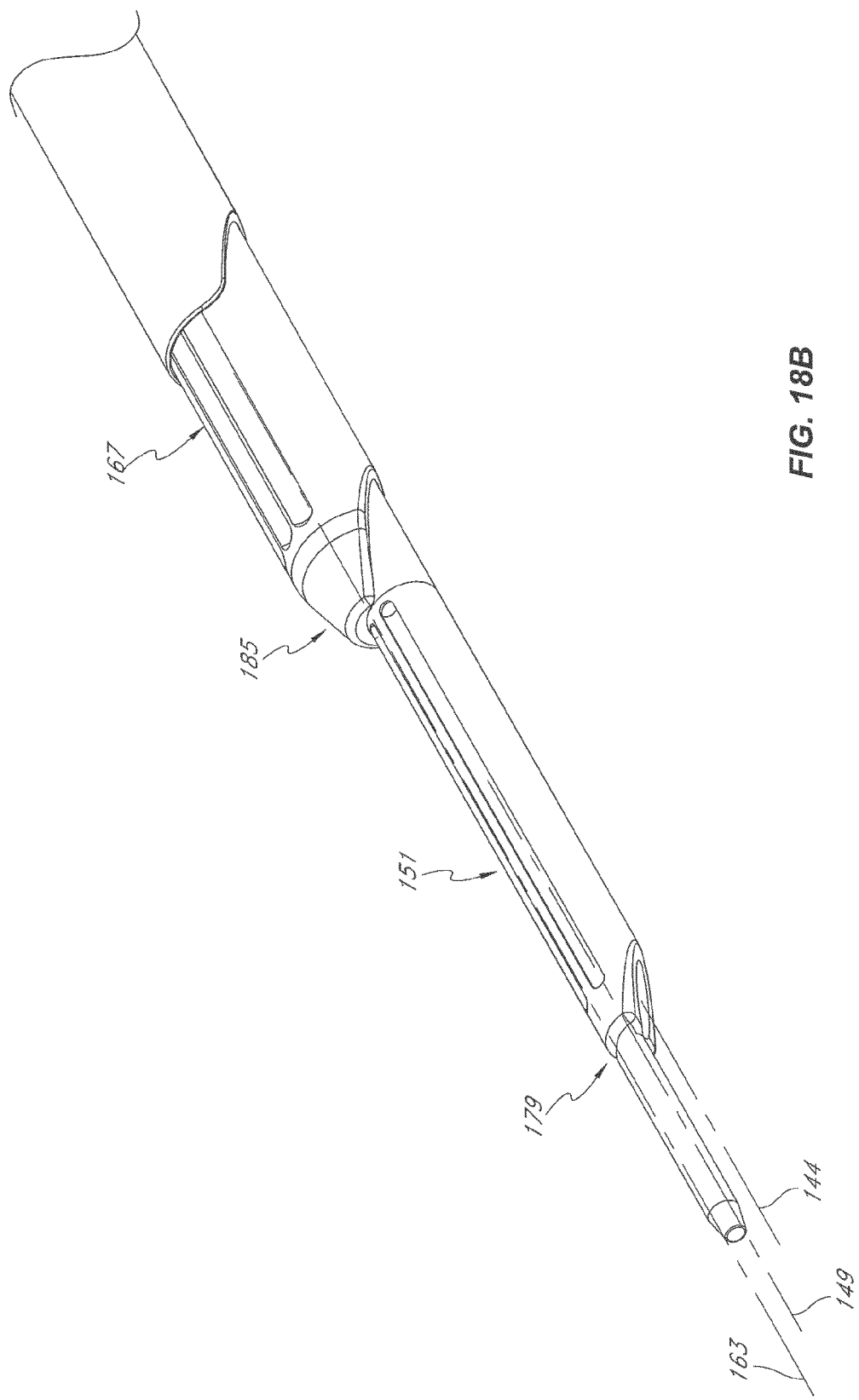
FIG. 18B is an enlarged detail view of the distal end of the dilation introducer shown in FIG. 18A.
Figure 18C:
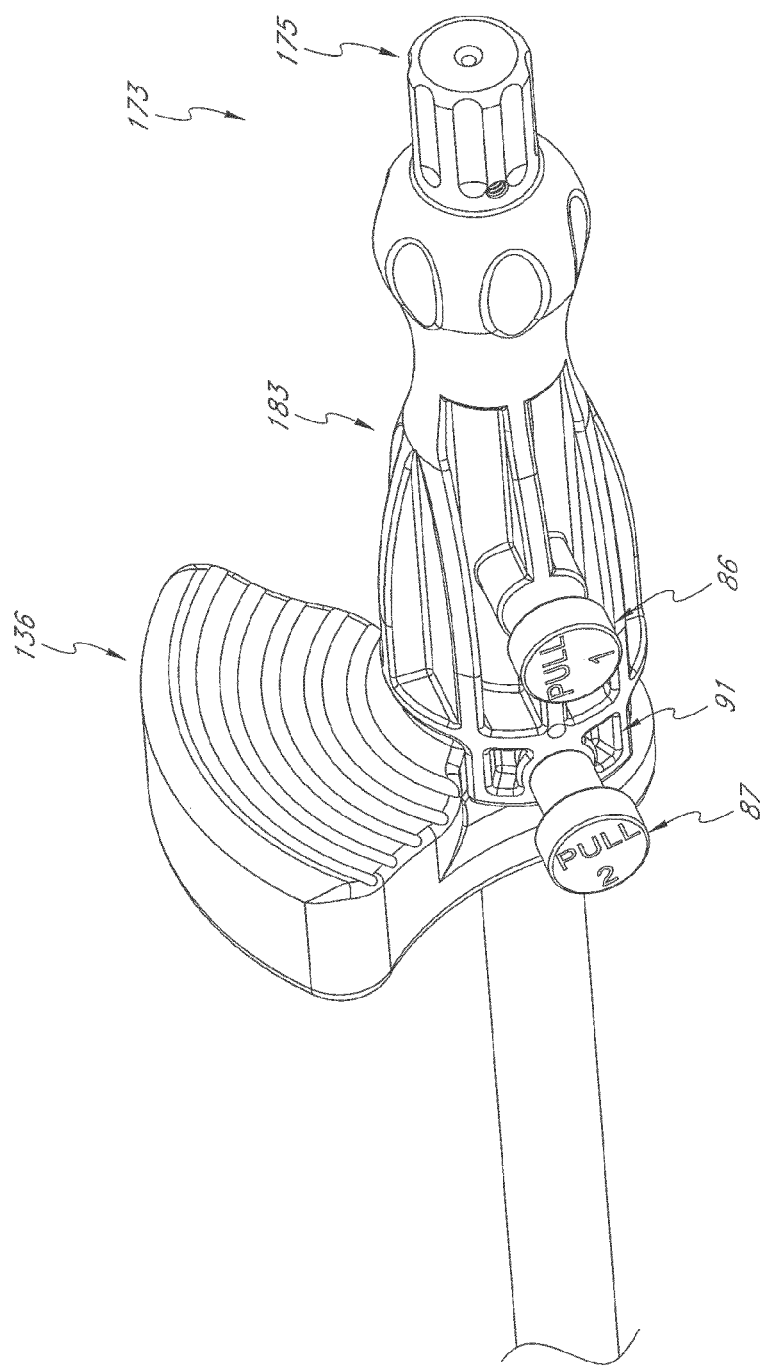
FIG. 18C is an enlarged detail view of the proximal end of the dilation introducer shown in FIG. 18A.

FIGS. 18A to 18C illustrate one embodiment of the dilation introducer 1100 in an assembled configuration. As shown, the access cannula 130 can be positioned over the third dilator tube 160, which can be positioned over the second dilator tube 145, which in turn can be positioned over the first dilator tube 140. The handle assembly 183 of the third dilator tube may be in a locked configuration with the proximal grip 136 of the access cannula can be locked together to constrain slidable movement, but allow for the access cannula 130 to rotate with respect to the third dilator tube 160. Additionally, the second dilator tube 145 may be locked together with the third dilator tube to constrain slidable movement, while still allowing the second dilator tube 145 to rotate with respect to the third dilator tube. Alternatively, the second dilator tube may be in a locked configuration preventing both slidable and rotational movement with respect to the third dilator tube 145. The third dilator tube 60 can be advanced distally until the distal portion 161 of the third dilator tube aligns with the distal portion 46 of the second dilator tube. Further, the access cannula 130 may also be advanced so that the distal portion 32 aligns with the distal portions 146, 161 of the second and third dilator tubes. The second and third dilator tubes 145, 160 each have cutting flutes 151, 167 on their respective distal portions 146, 161. As can be seen, the first, second, and third longitudinal axes 144, 149, 163 are each laterally offset from one another.

In certain embodiments, the first, second and third dilator tubes 140, 145, 160 along with the access cannula 130 can be provided with additional stops that engage the proximal grip 136 of the access cannula and the handle assembly 183 of the third dilator tube described above. For example, in one embodiment, notches or detents can be provided that engage the proximal grip 136 or handle assembly 183 when one tube is advanced distally and reaches a specific location (e.g., end point). In this manner, forward movement of a tube or cannula can be limited once the tube or cannula is advanced to a desired location FIG. 18B shows an enlarged detail view of the distal portion of the dilation introducer of FIG. 18A. The distal portions 146, 161, 132 of each of the second and third dilator tubes 145, 160, and of the access cannula 130 may have generally semi-annular cross-sections. The distal portions 146, 161 of the second and third dilator tubes 145, 160 in the illustrated embodiment can have flattened edges 179, 185 to prevent penetration into the intervertebral disc as each dilator tube is advanced.

FIG. 18C shows an enlarged detail view of the proximal portion of the dilation introducer of FIG. 18A. The proximal grip 136 of the access cannula 130 is shown in a locked configuration with the handle assembly 183 of the third dilator tube 160. The smaller diameter portion (not shown) may be received within the overhanging lip 191 on the distal end of the handle assembly 183. Latching buttons 186, 187 constrain movement of the third dilator tube relative to the second dilator tube, and of the access cannula relative to the third dilator tube, respectively. The gripping portion 175 of proximal head 173 of the first dilator tube 140 is visible at the proximal end of the dilation introducer. As shown, the first dilator tube may be fastened to the handle assembly 183 by means of the threaded portion 174 (not shown) on the proximal head 173 and the threaded receiving portion 190 (not shown) of the handle assembly 183. As shown, this fastening constrains both rotational and slidable movement of the first dilator tube relative to the third dilator tube. In various embodiments, the first dilator tube may be affixed to the handle assembly 183 by other means that allow for free rotational movement, free slidable movement, or both.

Figure 19A:
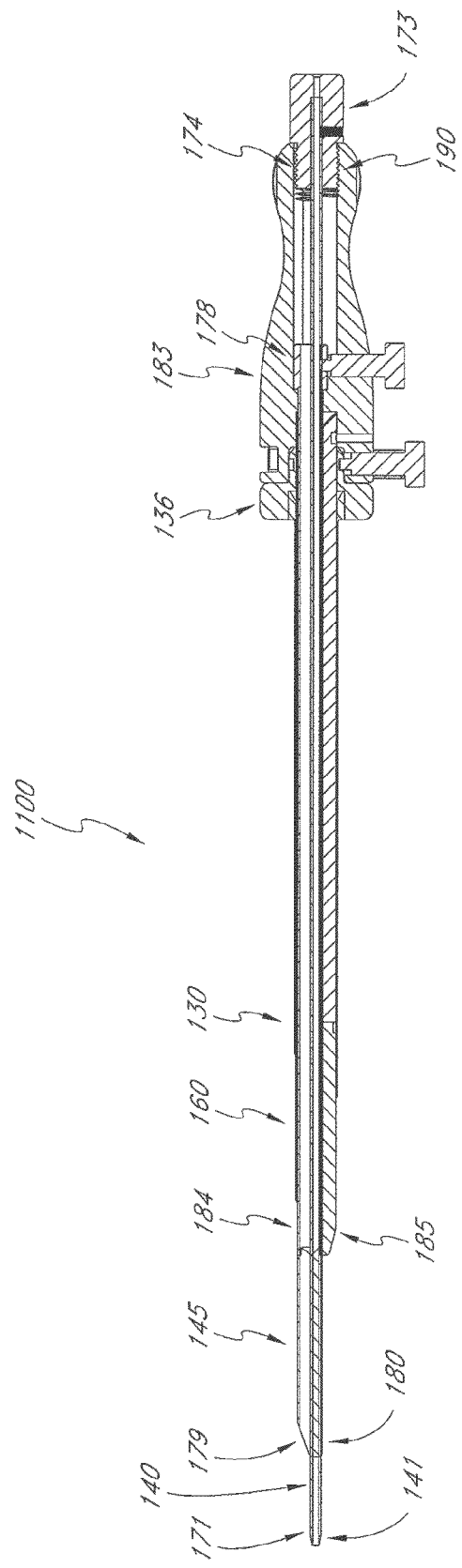
FIG. 19A is a longitudinal cross-sectional view of the dilation introducer of FIG. 18A.
Figure 19B:
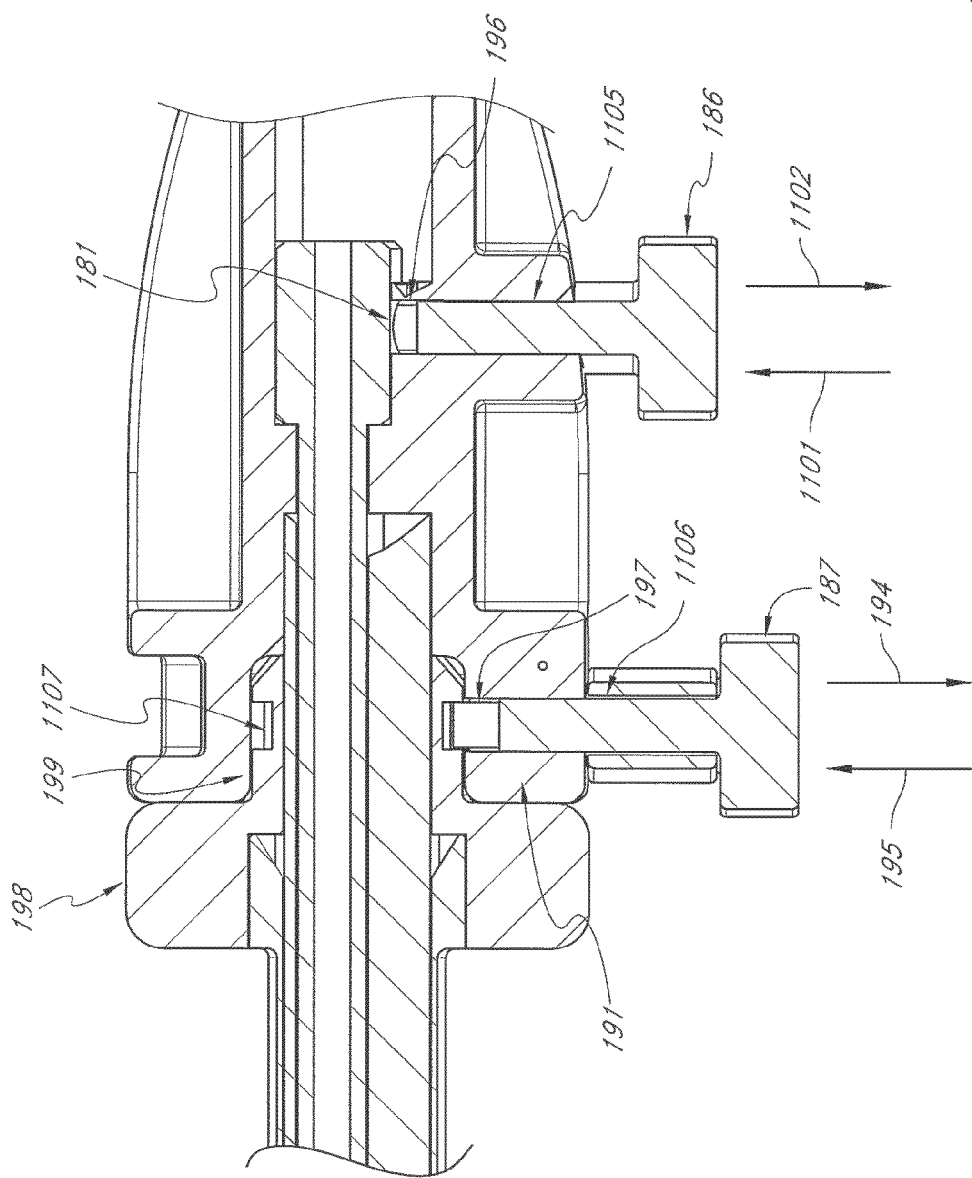
FIG. 19B is an enlarged detail of the longitudinal cross-sectional view shown in FIG. 19A.
Figure 20A:
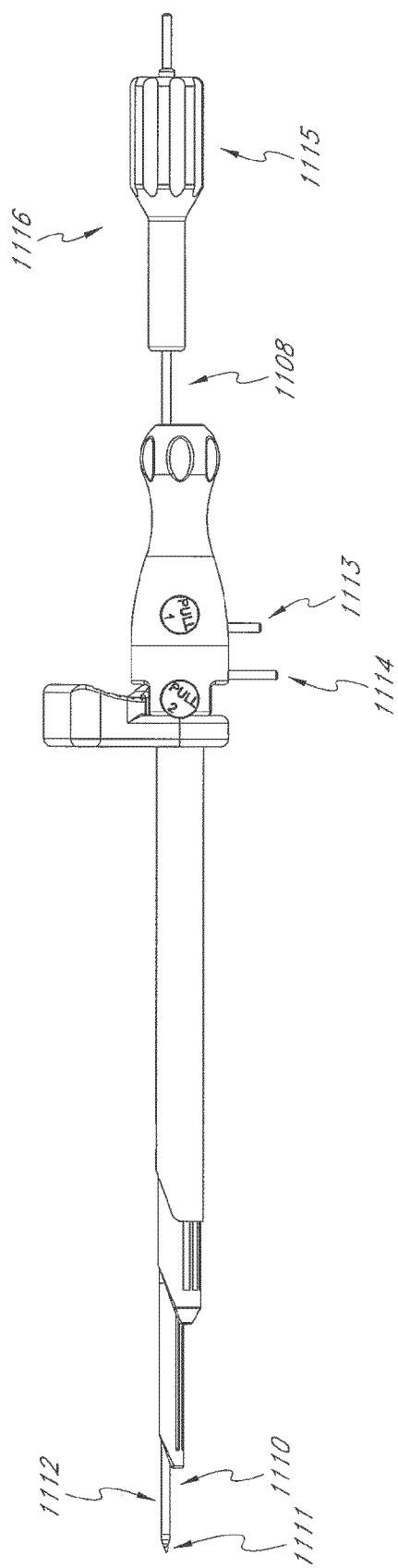
FIG. 20A is a plan view of a dilation introducer equipped with neuro-monitoring leads and a neuro-monitoring needle.
Figure 20B:
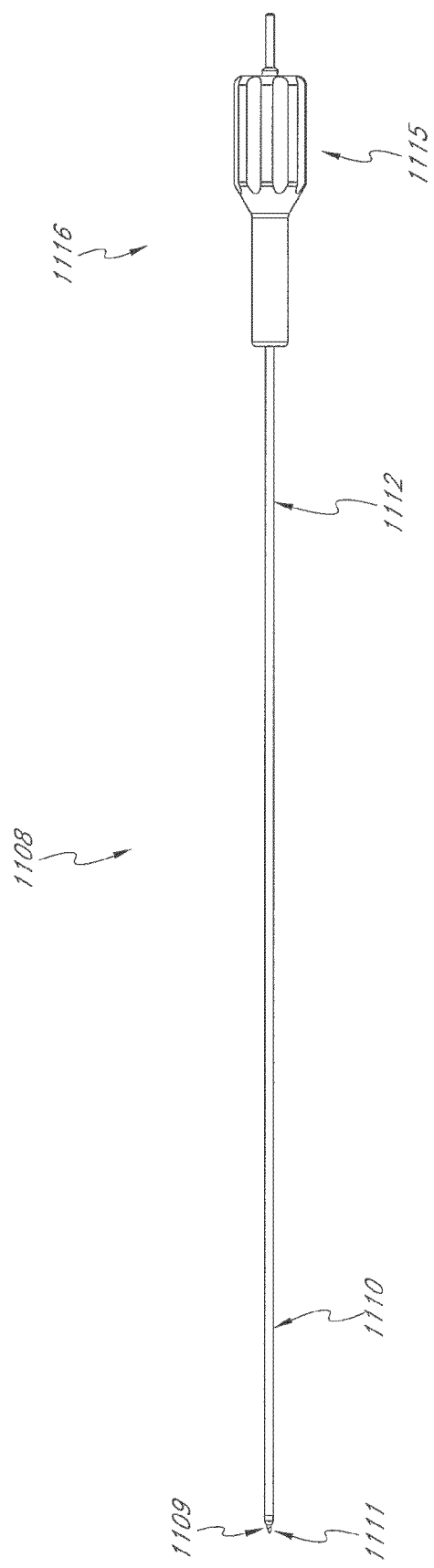
FIG. 20B is plan view of the neuro-monitoring needle shown in FIG. 20A.
Figure 20C:
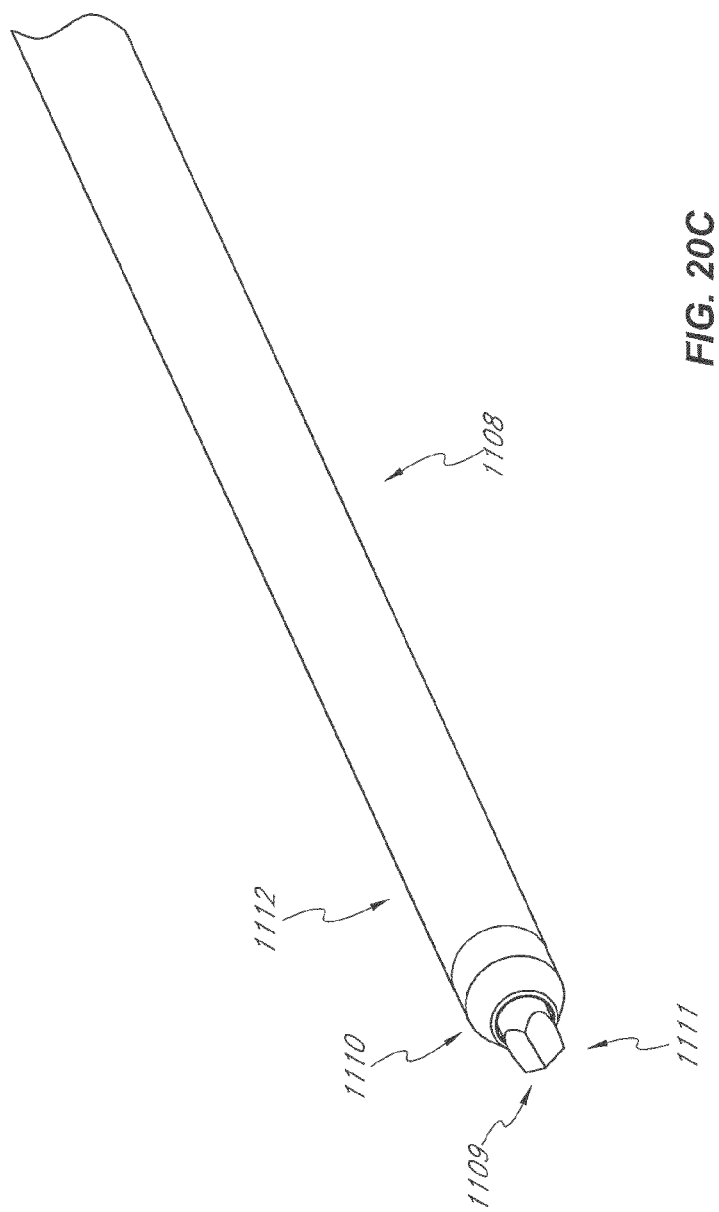
FIG. 20C is an enlarged detail view of a distal tip of a neuro-monitoring needle of FIG. 20A.
Figure 20D:
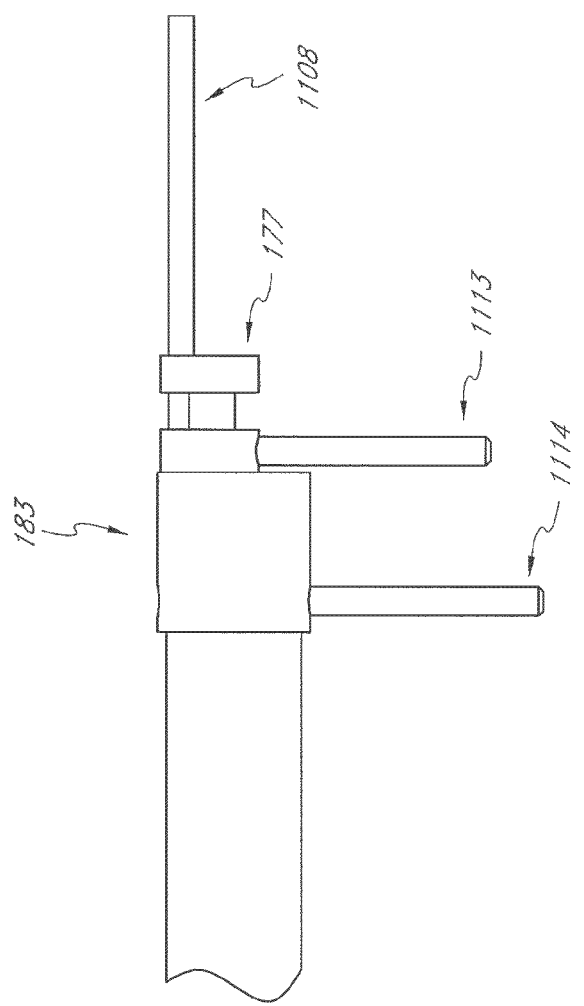
FIG. 20D is an enlarged detail view of the neuro-monitoring leads shown in FIG. 20A.

Referring to FIGS. 19A and 19B, a dilation introducer 1100 is shown in a locked assembled configuration. The dilation introducer 1100 includes a first dilator tube 140, a second dilator tube 145, a third dilator tube 160, and an access cannula 130. The first dilator tube has a distal portion 141 with a tapered tip 171, and a proximal portion 172 having a proximal head 173. In various embodiments, the first dilator tube 140 may be cannulated, for example to allow passage of a guide wire down the longitudinal axis 143 of the first dilator tube 140, or the first dilator tube may be without a lumen and uncannulated. The second dilator tube 145 has a distal tip 180 with a flattened edge 179, a proximal portion 177 with a collar 178, and a longitudinal lumen 148. The first dilator tube 140 may be removably received within the second dilator tube 145.

The third dilator tube 160 has a distal tip 184 with a flattened edge 185, a proximal portion 182 with a handle assembly 183, and a longitudinal lumen 164. The second dilator tube 145 may be removably received in the longitudinal lumen 164 of the third dilator tube 160 for slidable movement within the third dilator tube 160. The threaded portion 174 of the proximal head 173 of the first dilator tube engages with the interior threaded receiving portion 190 of the handle assembly 183 of the third dilator tube 160. With the proximal head of the first dilator tube affixed to the handle assembly 183, the first and third dilator tubes 140, 160 may be locked together for length and rotation. The second and third dilator tubes may be connected together in a locked configuration with a first latching button 186 disposed on the handle assembly 183 of the third dilator tube 160 and extending through a first aperture 1105 in the handle assembly 183 of the third dilator tube 160, so that the first latching button 186 may be moveable between a radially inward locking position (arrow 1101) and a radially outward unlocking position (arrow 1102).

The distal end 196 of the first latching button may be removably received in aperture 181 of the second dilator tube 145 so as to engage and lock the second and third dilators together in the locking position. Alternatively, the latching button may be received in a circumferentially oriented groove of the second dilator tube, which may or may not extend completely around the second dilator tube. The first latching button 186 may be pulled radially outwardly to release the second dilator tube 145, to allow the third dilator tube 160 to slide with respect to the second dilator tube 145.

The access cannula 130 has a distal portion 161, a proximal portion 193, a proximal grip 136, and longitudinal lumen 164. The third dilator tube 145 may be removably received within the access cannula 130 for slidable movement within the longitudinal lumen 131 of the access cannula 130. The third dilator tube 145 and the access cannula 130 also have a locked configuration in which the access cannula 130 may be not permitted to slidably telescope over the third dilator tube 145.

The proximal portion 193 of the access cannula 130 includes a proximal grip 136 with a larger diameter portion 198 and a smaller diameter portion 199. The smaller diameter portion 199 may be sized to fit under an overhanging lip 191 of the third dilator tube, when the longitudinal axes of the third dilator tube and access cannula may be aligned. There may be a circumferentially oriented channel 1107 in the exterior of the smaller diameter portion 919 for receiving a distal end 197 of a second latching button 187. The circumferentially oriented channel 1107 does not need to extend completely around the exterior of the smaller diameter portion 199.

The third dilator tube 145 and the access cannula 130 may be connected together in a locked configuration with the second latching button 187 disposed on the overhanging lip 191 of the handle assembly 183 of the third dilator tube 145. The second latching button extends through an aperture 1106 in the overhanging lip 191 of the handle assembly 183 and may be movable between a radially inward locking position (arrow 194) and a radially outward unlocking position (arrow 195). The distal end 197 of the second latching button 187 may be removably received in the channel 107 located in the smaller diameter portion 199 of the access cannula 130, in the locking position, to lock the third dilator tube 45 and the access cannula 130 in the locked assembled configuration. The second latching button 187 may be pulled radially outward to release the access cannula 130 to slide to the unlocked configuration. Furthermore, the second and third dilator tubes 140, 145 may be removed together as a unit from the access cannula 130. In other words, the first dilator tube 140 and second dilator tube 145 can be kept locked together and can be removed from the access cannula 130 by unlocking the second latching button 187 alone. An advantage of this embodiment is that the latching buttons 186, 187 may be both removable from the surgical field with the release of the third dilator tube from the access cannula 130.

The access cannula being free of protuberances, such as the latching buttons, is less likely to catch surgical sponges and sutures, for example, on the dilation introducer.

Dilation Introducer with Neuro-Monitoring

FIGS. 20A to 20D show another aspect of a dilation introducer, in which the first dilator tube may be replaced with a neuro-monitoring needle 1108. The neuro-monitoring needle 1108 includes a wire 1109 which may be enclosed by a needle cannula 1110, with the wire 1109 exposed at the distal tip 1111. The needle cannula 1110 may be surrounded by dielectric coating 1112 along its length for insulation. For example, the wire 1109 can comprise stainless steel and the dielectric coating 1112 can comprise parylene. As noted above, a knob 1115 may be located on the proximal portion 1116 of the neuro-monitoring needle 1108. A first neuro-monitoring lead 1113 may be attached to the proximal portion 177 of the second dilator tube 145. A second neuro-monitoring lead 1114 may be attached to the proximal portion 183 of the third dilator tube 160.

The neuro-monitoring needle 1108 can be made from several components. The wire 1108 portion can be stainless steel coated with dielectric coating 1112 of parylene. The distal tip 1111 of the wire 1109 can be exposed so that it can transmit current. The needle cannula 1110 which covers the wire 1109 can also comprise stainless steel coated with parylene. In some embodiments, this needle cannula could also be described as an exchange tube where once the wire is removed a K-wire could be placed down it and into the disc space. The wire 1109 can be attached to a handle at the proximal end ultimately protrude from the handle, serving as the electrode to attach a neuromonitoring system. In some embodiments, the proximal diameter can be parylene coated, while the rest of the wire 1109 can be uncoated to transmit the current.

The wire 1109 may comprise a conductive material, such as silver, copper, gold, aluminum, platinum, stainless steel, etc. A constant current may be applied to the wire 1109. The needle cannula 1110 may be insulated by dielectric coating 1112. Although the coating shown here is dielectric, any sufficiently insulative coating may be used. Alternatively, an insulative sleeve may encase the wire. This arrangement protects the conductive wire 1109 at all points except the most distal tip 1111. As the exposed tip of the wire 1109 is advanced through the tissue, it continues to be supplied with current. When the tip 1111 approaches a nerve, the nerve may be stimulated. The degree of stimulation to the nerve is related to the distance between the distal tip 1111 and the nerve. Stimulation of the nerve may be measured by, e.g., visually observing the patient's leg for movement, or by measuring muscle activity through electromyography (EMG) or various other known techniques.

Utilizing this configuration may provide the operator with added guidance as to the positioning of the first dilator tube to the surgical access point and through Kambin's triangle. With each movement, the operator may be alerted when the tip of the first dilator tube approaches or comes into contact with a nerve. The operator may use this technique alone or in conjunction with other positioning assistance techniques such as fluoroscopy and tactile feedback. The amount of current applied to the wire 1109 may be varied depending on the preferred sensitivity. Naturally, the greater the current supplied, the greater nerve stimulation will result at a given distance from the nerve. In various embodiments the current applied to the conductive wire 1109 may not be constant, but rather periodic or irregular. Alternatively, pulses of current may be provided only on demand from the operator.

Although not shown here, a similar configuration may be applied to the second and third dilator tubes, and to the access cannula. Each may include a conductive wire embedded within the tube, or it may be separately attached. In either configuration, a distal tip of conductive wire may be exposed and the wire may be provided with current. As the dilator tube or access cannula is advanced through the tissue and towards the access site, nerve stimulation may be monitored as described above. The current supplied to each of the first, second, and third dilator tubes and to the access cannula may be controlled independently, so that when nerve stimulation is observed, the operator may supply current separately to each wire to determine which wire or wires are nearest to the nerve. Alternatively, current may be supplied only to one wire at any given point in the procedure. For example, the current may be supplied to the wire associated with the dilator tube or access cannula that is being moved at that point in the operation.

In some embodiments, the second and third dilator tubes can comprise aluminum that has been anodized and then coated with parylene. Certain areas of the second and third dilator tubes can be masked from the anodization and parylene coating so that they can transmit the current. For example, the distal tips of the second and third dilator tubes can be exposed so as to conduct current therethrough. The exposed portions can be passivated to resist rusting, pitting, or corrosion. The exposed portions can be made by using a stainless steel pin pressed into the second and third dilator tubes. The pin can aid in locating the second and third dilator tubes on x-ray or fluoroscopy, and additionally can facilitate the transmission of current through the second and third dilator tubes to the area of contact. Electrode attachments for the second and third dilator tubes can be coated with parylene on the proximal larger diameter to prevent current from flowing into the user. The rest of the electrode can be uncoated, but passivated to resist rusting, pitting, or corrosion. The electrodes can attach such that the current is transmitted to the internal area of the second and third dilator tubes so that it can be transmitted distally through the exposed areas on the tips of the tubes. These tubes are attached to Radel handles, which being a polymer are also insulators. The third dilator tube can be made from stainless steel, coated with nylon or other polymer, such as Teflon, followed by a parylene coating. In embodiments in which the dilator tube comprises stainless steel, no additional x-ray marker is required.

Although the method as described above utilizes an embodiment of the dilation introducer as shown in FIGS. 3-7B, it will be understood that the procedure may be adapted for use with various other embodiments of the dilation introducer. For instance, the dilation introducer with alternative handle assembly, as shown in FIGS. 14A-19C, may be used with appropriate modifications to the method described above. For instance, as the proximal head 173 of the first dilator tube 140 may be screwed into the handle assembly 183 of the third dilator tube 160, the first dilator tube 140 must be unscrewed and removed prior to advancing the third dilator tube over the second dilator tube. Additionally, the latching buttons 186, 187 of the handle assembly 183 may be used to control the locking and unlocking of the dilator tubes relative to one another.

Alternatively, the dilation introducer equipped with neuro-monitoring, as shown in FIGS. 20A-D, may be substituted. The method performed may be then similar to that described above, except that in addition the method involves monitoring nerve stimulation to assist with placement and guidance of the dilator tubes and access cannula. As described above, the current supplied to the conductive wires may be varied and controlled in order to determine the optimal location for the dilation introducer and/or access cannula.

Implant

With respect to the implant 80 described above, the implant 80 can comprise any of a variety of types of interbody devices configured to be placed between vertebral bodies. The implant 80 can be formed from a metal (e.g., titanium) or a non-metal material such as plastics, PEEK™, polymers, and rubbers. Further, the implant components can be made of combinations of non metal materials (e.g., PEEK™, polymers) and metals. The implant 80 can be configured with a fixed or substantially fixed height, length and width as shown, for example, in the embodiment of FIG. 13. In other embodiments, the implant can be configured to be expandable along one or more directions. For example, in certain embodiments the height of the implant can be expanded once the device advanced through the access cannula and positioned between vertebral bodies (e.g., within the disc space within the annulus).

Figure 21A:
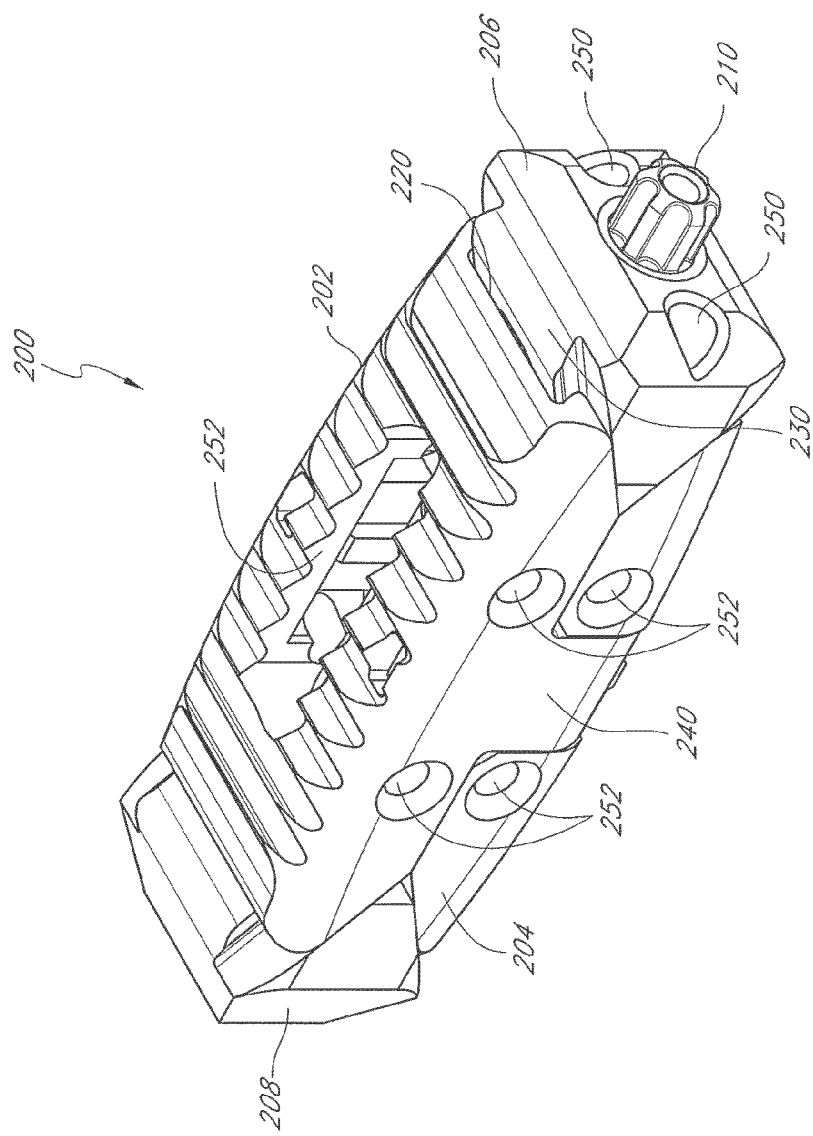
FIG. 21A is a perspective view of another embodiment of an intervertebral implant in an unexpanded state.
Figure 21B:
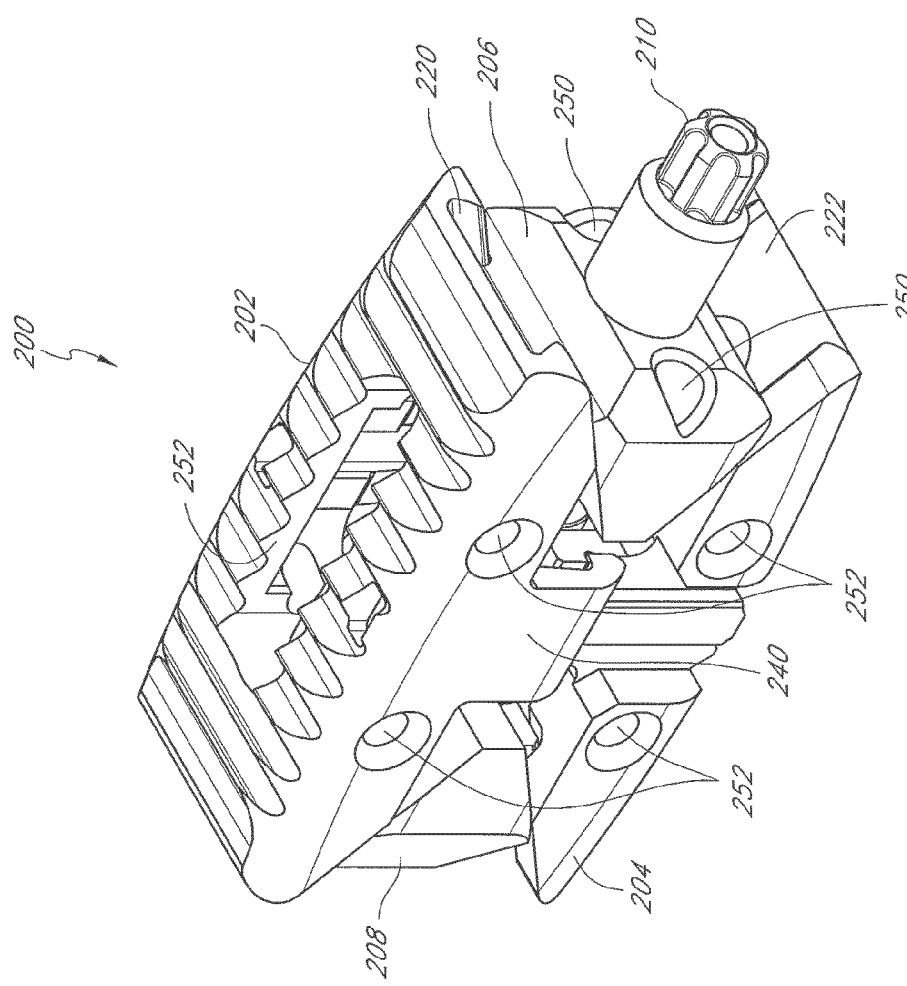
FIG. 21B is a perspective view of the intervertebral implant shown in FIG. 20A wherein the implant is in an expanded state.
Figure 22:
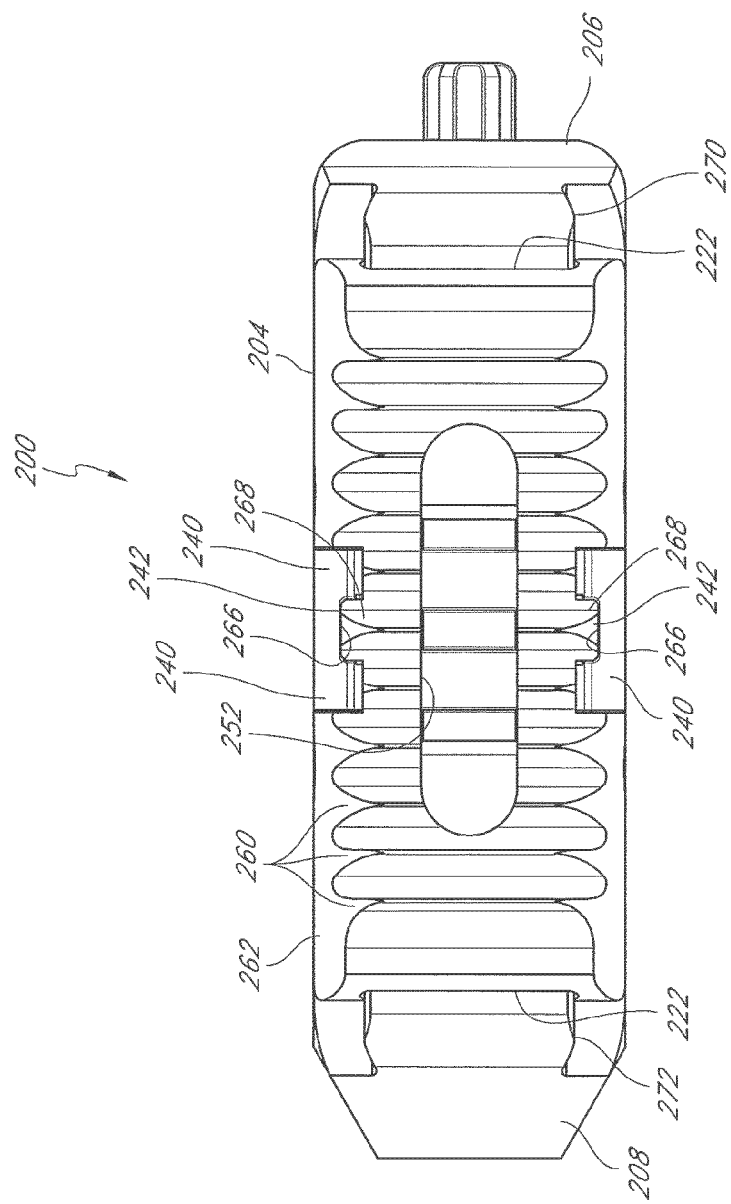
FIG. 22 is a bottom view of the intervertebral implant shown in FIG. 21A.
Figure 24:
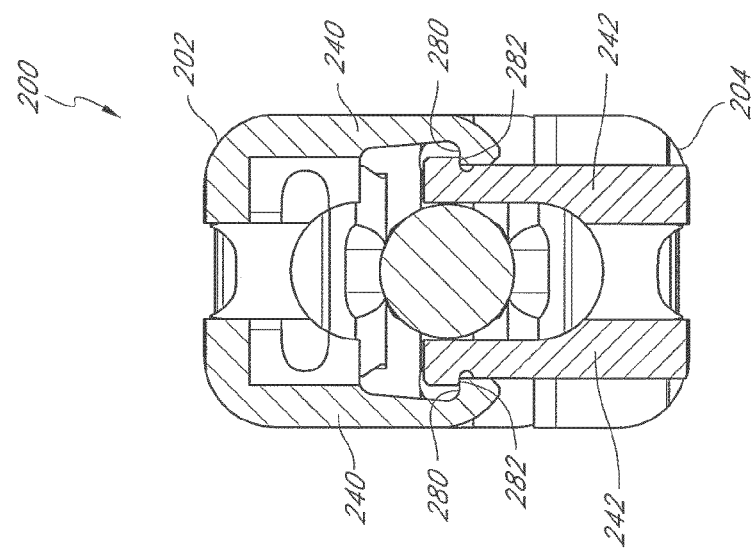
FIG. 24 is a front cross-sectional view of the intervertebral implant shown in FIG. 21B taken along lines 19-19.
Figure 23:
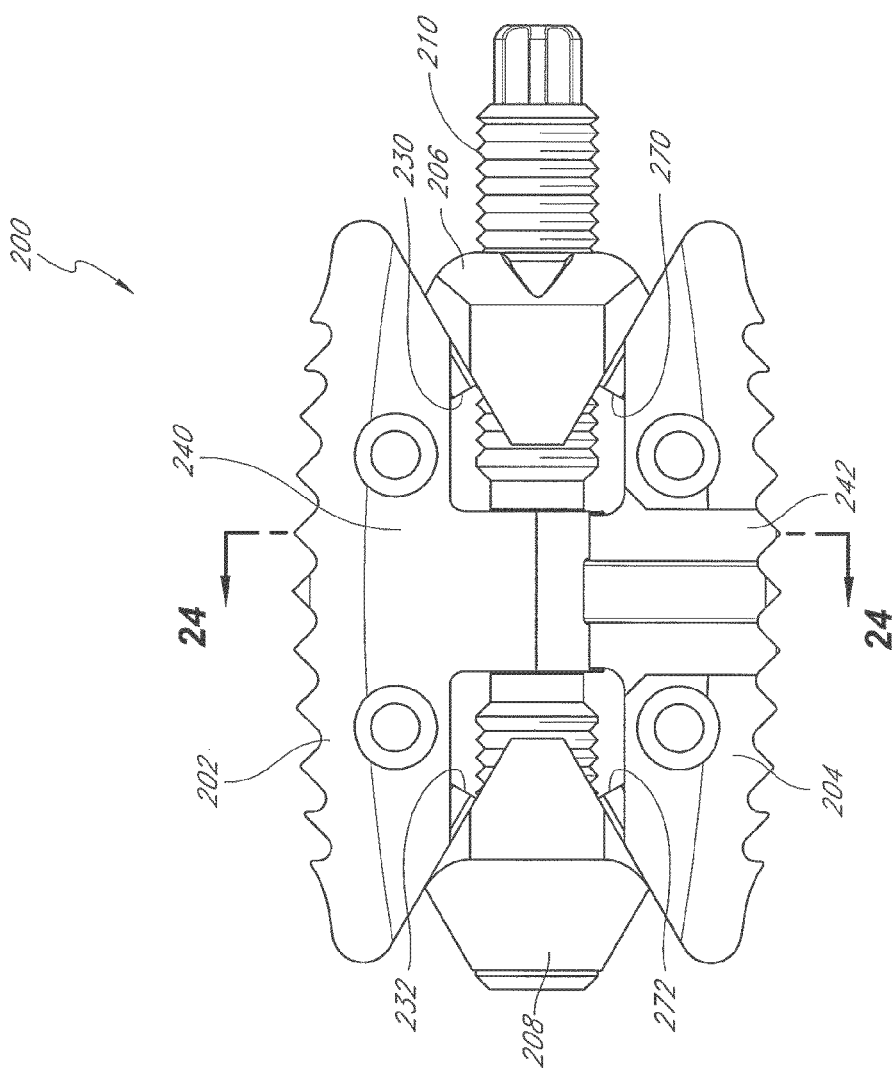
FIG. 23 is a side view of the intervertebral implant shown in FIG. 21B.

Additional detail of one embodiment of such an expandable implant can be found in FIGS. 21A-31. As shown, in FIGS. 21A-B, in the illustrated embodiments, the implant 200 can be configured such that proximal and distal wedge members 206, 208 are interlinked with upper and lower body portions 202, 204. The upper and lower body portions 202, 204 can include slots (slot 220 is shown in FIG. 21A, and slots 220, 222 are shown in FIG. 21B; the configuration of such an embodiment of the upper and lower body portions 202, 204 is also shown in FIGS. 21A-22B, discussed below). In such an embodiment, the proximal and distal wedge members 206, 208 can include at least one guide member (an upper guide member 230 of the proximal wedge member 206 is shown in FIG. 21A and an upper guide member 232 of the distal wedge member 208 is shown in FIG. 23) that at least partially extends into a respective slot of the upper and lower body portions. The arrangement of the slots and the guide members can enhance the structural stability and alignment of the implant 200.

In addition, it is contemplated that some embodiments of the implant 200 can be configured such that the upper and lower body portions 202, 204 each include side portions (shown as upper side portion 240 of the upper body portion 202 and lower side portion 242 of the lower body portion 204) that project therefrom and facilitate the alignment, interconnection, and stability of the components of the implant 200. FIG. 21B is a perspective view of the implant 200 wherein the implant 200 is in the expanded state. The upper and lower side portions 240, 242 can be configured to have complementary structures that enable the upper and lower body portions 202, 204 to move in a vertical direction. Further, the complementary structures can ensure that the proximal ends of the upper and lower body portions 202, 204 generally maintain spacing equal to that of the distal ends of the upper and lower body portions 202, 204. The complementary structures are discussed further below with regard to FIGS. 22-26B.

Furthermore, as described further below, the complementary structures can also include motion limiting portions that prevent expansion of the implant beyond a certain height. This feature can also tend to ensure that the implant is stable and does not disassemble during use.

In some embodiments, the actuator shaft 210 can facilitate expansion of the implant 200 through rotation, longitudinal contract of the pin, or other mechanisms. The actuator shaft 210 can include threads that threadably engage at least one of the proximal and distal wedge members 206, 208. The actuator shaft 210 can also facilitate expansion through longitudinal contraction of the actuator shaft as proximal and distal collars disposed on inner and outer sleeves move closer to each other to in turn move the proximal and distal wedge members closer together. It is contemplated that in other embodiments, at least a portion of the actuator shaft can be axially fixed relative to one of the proximal and distal wedge members 206, 208 with the actuator shaft being operative to move the other one of the proximal and distal wedge members 206, 208 via rotational movement or longitudinal contraction of the pin.

Further, in embodiments wherein the actuator shaft 210 is threaded, it is contemplated that the actuator shaft 210 can be configured to bring the proximal and distal wedge members closer together at different rates. In such embodiments, the implant 200 could be expanded to a V-configuration or wedged shape. For example, the actuator shaft 210 can comprise a variable pitch thread that causes longitudinal advancement of the distal and proximal wedge members at different rates. The advancement of one of the wedge members at a faster rate than the other could cause one end of the implant to expand more rapidly and therefore have a different height that the other end. Such a configuration can be advantageous depending on the intervertebral geometry and circumstantial needs.

In other embodiments, the implant 200 can be configured to include anti-torque structures 250. The anti-torque structures 250 can interact with at least a portion of a deployment tool during deployment of the implant to ensure that the implant maintains its desired orientation (see FIGS. 30-31 and related discussion). For example, when the implant 200 is being deployed and a rotational force is exerted on the actuator shaft 210, the anti-torque structures 250 can be engaged by a non-rotating structure of the deployment tool to maintain the rotational orientation of the implant 200 while the actuator shaft 210 is rotated. The anti-torque structures 250 can comprise one or more inwardly extending holes or indentations on the proximal wedge member 206, which are shown as a pair of holes in FIGS. 21A-B. However, the anti-torque structures 250 can also comprise one or more outwardly extending structures.

According to yet other embodiments, the implant 200 can be configured to include one or more apertures 252 to facilitate osseointegration of the implant 200 within the intervertebral space. As mentioned above, the implant 200 may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Indeed, various biologics can be used with the implant 200 and can be inserted into the disc space or inserted along with the implant 200. The apertures 252 can facilitate circulation and bone growth throughout the intervertebral space and through the implant 200. In such implementations, the apertures 252 can thereby allow bone growth through the implant 200 and integration of the implant 200 with the surrounding materials.

FIG. 22 is a bottom view of the implant 200 shown in FIG. 21A. As shown therein, the implant 200 can comprise one or more protrusions 260 on a bottom surface 262 of the lower body portion 204. Although not shown in this Figure, the upper body portion 204 can also define a top surface having one or more protrusions thereon. The protrusions 260 can allow the implant 200 to engage the adjacent vertebrae when the implant 200 is expanded to ensure that the implant 200 maintains a desired position in the intervertebral space.

The protrusions 260 can be configured in various patterns. As shown, the protrusions 260 can be formed from grooves extending widthwise along the bottom surface 262 of the implant 200 (also shown extending from a top surface 264 of the upper body portion 202 of the implant 200). The protrusions 260 can become increasingly narrow and pointed toward their apex. However, it is contemplated that the protrusions 260 can be one or more raised points, cross-wise ridges, or the like.

FIG. 22 also illustrates a bottom view of the profile of an embodiment of the upper side portion 240 and the profile of the lower side portion 242. As mentioned above, the upper and lower side portions 240, 242 can each include complementary structures to facilitate the alignment, interconnection, and stability of the components of the implant 200. FIG. 22 also shows that in some embodiments, having a pair of each of upper and lower side portions 240, 242 can ensure that the upper and lower body portions 202, 204 do not translate relative to each other, thus further ensuring the stability of the implant 200.

As illustrated in FIG. 22, the upper side portion 240 can comprise a groove 266 and the lower side portion can comprise a rib 268 configured to generally mate with the groove 266. The groove 266 and rib 268 can ensure that the axial position of the upper body portion 202 is maintained generally constant relative to the lower body portion 204. Further, in this embodiment, the grooves 266 and rib 268 can also ensure that the proximal ends of the upper and lower body portions 202, 204 generally maintain spacing equal to that of the distal ends of the upper and lower body portions 202, 204. This configuration is also illustratively shown in FIG. 23.

Referring again to FIG. 22, the implant 200 is illustrated in the unexpanded state with each of the respective slots 222 of the lower body portion 204 and lower guide members 270, 272 of the respective ones of the proximal and distal wedge members 206, 208. In some embodiments, as shown in FIGS. 21A-22 and 24-26B, the slots and guide members can be configured to incorporate a generally dovetail shape. Thus, once a given guide member is slid into engagement with a slot, the guide member can only slide longitudinally within the slot and not vertically from the slot. This arrangement can ensure that the proximal and distal wedge members 206, 208 are securely engaged with the upper and lower body portions 202, 204.

Furthermore, in FIG. 23, a side view of the embodiment of the implant 200 in the expanded state illustrates the angular relationship of the proximal and distal wedge members 206, 208 and the upper and lower body portions 202, 204. As mentioned above, the dovetail shape of the slots and guide members ensures that for each given slot and guide member, a given wedge member is generally interlocked with the give slot to only provide one degree of freedom of movement of the guide member, and thus the wedge member, in the longitudinal direction of the given slot.

Accordingly, in such an embodiment, the wedge members 206, 208 may not be separable from the implant when the implant 200 is in the unexpanded state (as shown in FIG. 21A) due to the geometric constraints of the angular orientation of the slots and guide members with the actuator shaft inhibiting longitudinal relative movement of the wedge members 206, 208 relative to the upper and lower body portions 202, 204. Such a configuration ensures that the implant 200 is stable and structurally sound when in the unexpanded state or during expansion thereof, thus facilitating insertion and deployment of the implant 200.

Such an embodiment of the implant 200 can therefore be assembled by placing or engaging the wedge members 206, 208 with the actuator shaft 210, moving the wedge members 206, 208 axially together, and inserting the upper guide members 230, 232 into the slots 220 of the upper body portion 202 and the lower guide members 270, 272 into the slots 222 of the lower body portion 204. The wedge members 206, 208 can then be moved apart, which movement can cause the guide members and slots to engage and bring the upper and lower body portions toward each other. The implant 200 can then be prepared for insertion and deployment by reducing the implant 200 to the unexpanded state.

During assembly of the implant 200, the upper and lower body portions 202, 204 can be configured to snap together to limit expansion of the implant 200. For example, the upper and lower side portions 240, 242 can comprise upper and lower motion-limiting structures 280, 282, as shown in the cross-sectional view of FIG. 24. After the wedge members 206, 208 are engaged with the upper and lower body portions 202, 204 and axially separated to bring the upper and lower body portions 202, 204 together, the upper motion-limiting structure 280 can engage the lower motion-limiting structure 282. This engagement can occur due to deflection of at least one of the upper and lower side portions 240, 242. However, the motion-limiting structures 280, 282 preferably comprise interlocking lips or shoulders to engage one another when the implant 200 has reached maximum expansion. Accordingly, after the wedge members 206, 208 are assembled with the upper and lower body portions 202, 204, these components can be securely interconnected to thereby form a stable implant 200.

Referring again to FIG. 23, the implant 200 can define generally convex top and bottom surfaces 264, 262. In modified embodiments, the shape can be modified.

Figure 25B:
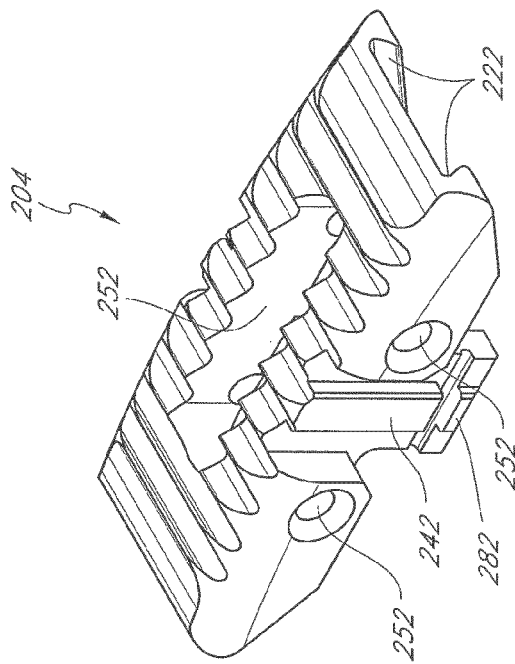
FIG. 25B is a top perspective view of the lower body portion of the intervertebral implant shown in FIG. 24A.
Figure 25A:
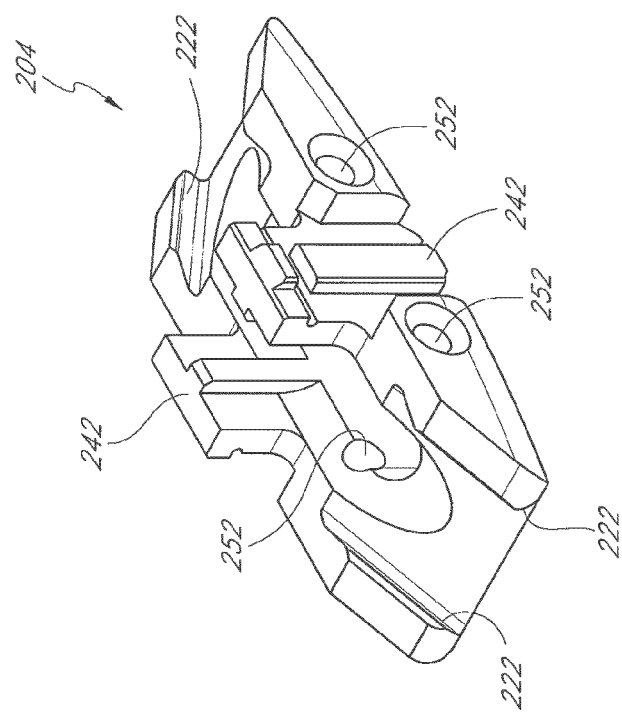
FIG. 25A is a bottom perspective view of a lower body portion of the intervertebral implant shown in FIG. 24A.
Figure 26B:
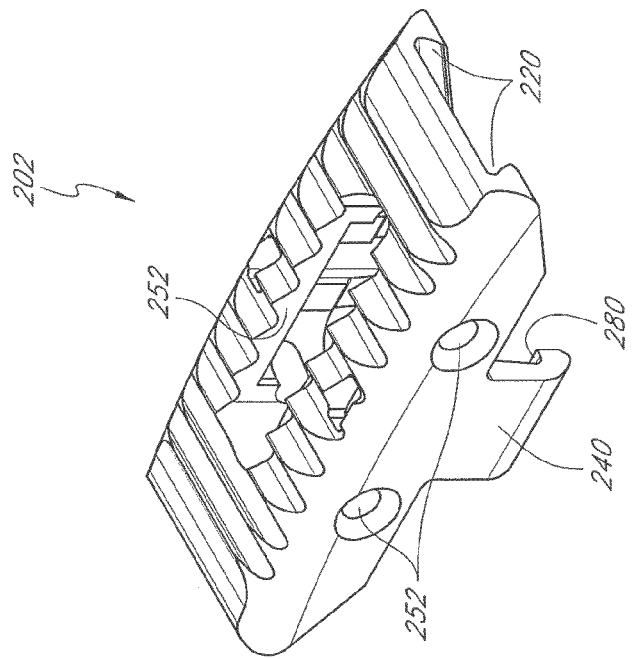
FIG. 26B is a top perspective view of the upper body portion of the intervertebral implant shown in FIG. 24A.
Figure 26A:
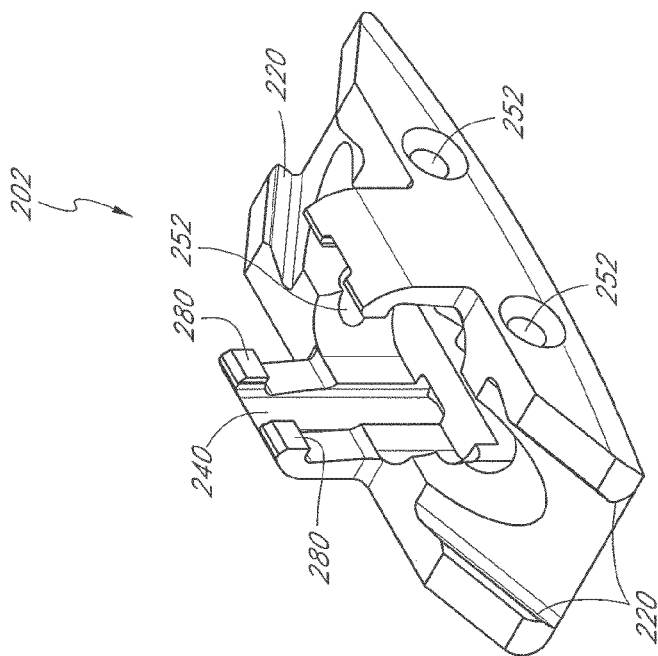
FIG. 26A is a bottom perspective view of an upper body portion of the intervertebral implant shown in FIG. 24A.

FIGS. 25A-B illustrate perspective views of the lower body portion 204 of the implant 200, according to an embodiment. These Figures provide additional clarity as to the configuration of the slots 222, the lower side portions 242, and the lower motion-limiting members 282 of the lower body portion 204. Similarly, FIGS. 26A-B illustrate perspective views of the upper body portion 202 of the implant 200, according to an embodiment. These Figures provide additional clarity as to the configuration of the slots 220, the upper side portions 240, and the upper motion-limiting members 280 of the upper body portion 202. Additionally, the upper and lower body portions 202, 204 can also define a central receptacle 290 wherein the actuator shaft can be received. Further, as mentioned above, the upper and lower body portions 202, 204 can define one or more apertures 252 to facilitate osseointegration.

Figure 27:
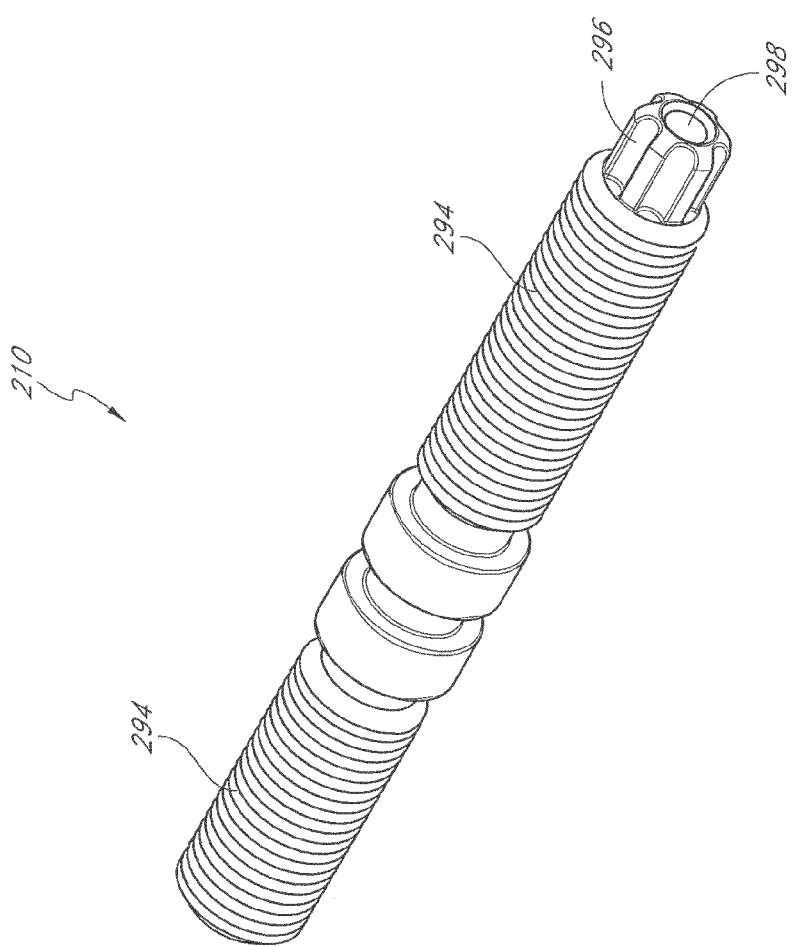
FIG. 27 is a perspective view of an actuator shaft of the intervertebral implant shown in FIG. 21A.

FIG. 27 is a perspective view of an actuator shaft 210 of the implant 200 shown in FIG. 21. In this embodiment, the actuator shaft 210 can be a single, continuous component having threads 294 disposed thereon for engaging the proximal and distal wedge members 206, 208. The threads can be configured to be left hand threads at a distal end of the actuator shaft 210 and right hand threads at a proximal other end of the actuator shaft for engaging the respective ones of the distal and proximal wedge members 208, 206. Accordingly, upon rotation of the actuator shaft 210, the wedge members 206, 208 can be caused to move toward or away from each other to facilitate expansion or contraction of the implant 200. Further, as noted above, although this embodiment is described and illustrated as having the actuator shaft 210 with threads 294.

In accordance with an embodiment, the actuator shaft 210 can also comprise a tool engagement section 296 and a proximal engagement section 298. The tool engagement section 296 can be configured as a to be engaged by a tool, as described further below. The tool engagement section 296 can be shaped as a polygon, such as a hex shape. As shown, the tool engagement section 296 is star shaped and includes six points, which configuration tends to facilitate the transfer of torque to the actuator shaft 210 from the tool. Other shapes and configurations can also be used.

Furthermore, the proximal engagement section 298 of the actuator shaft 210 can comprise a threaded aperture. The threaded aperture can be used to engage a portion of the tool for temporarily connecting the tool to the implant 200. It is also contemplated that the proximal engagement section 298 can also engage with the tool via a snap or press fit.

Figure 28B:
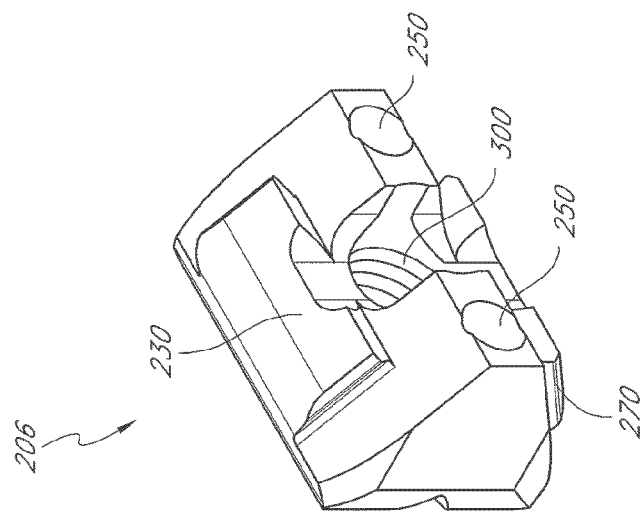
FIG. 28B is a rear perspective view of the proximal wedge member of the intervertebral implant shown in FIG. 21A.
Figure 28A:
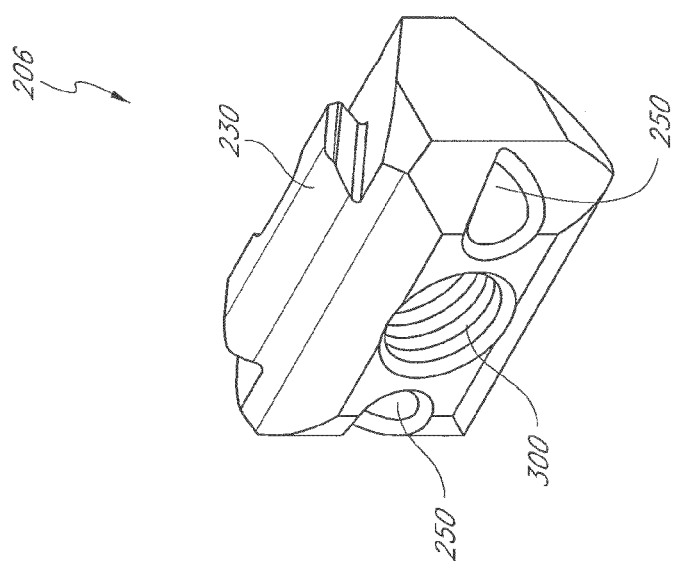
FIG. 28A is a front perspective view of a proximal wedge member of the intervertebral implant shown in FIG. 21A.

FIG. 28A-B illustrate perspective views of the proximal wedge member 206 of the implant 200. As described above, the proximal wedge member can include one or more anti-torque structures 250. Further, the guide members 230, 270 are also illustrated. The proximal wedge member 206 can comprise a central aperture 300 wherethrough an actuator shaft can be received. When actuator shaft 210 is used in an embodiment, the central aperture 300 can be threaded to correspond to the threads 294 of the actuator shaft 210. In other embodiments, the actuator shaft can engage other portions of the wedge member 206 for causing expansion or contraction thereof.

Figure 29A:
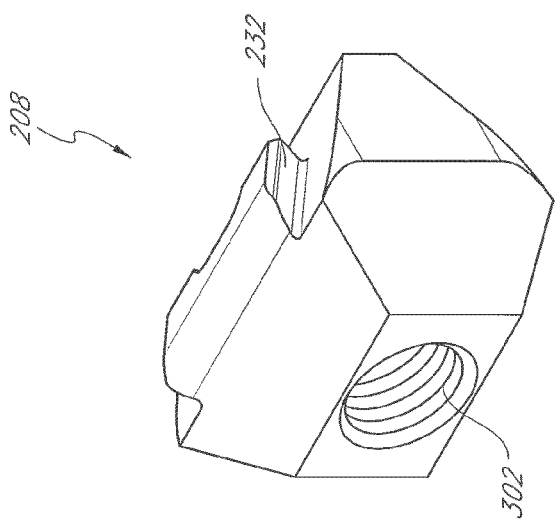
FIG. 29A is a front perspective view of a distal wedge member of the intervertebral implant shown in FIG. 21A.
Figure 29B:
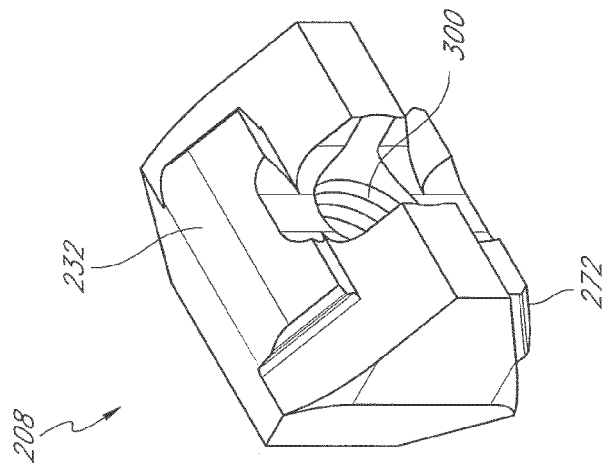
FIG. 29B is a rear perspective view of the distal wedge member of the intervertebral implant shown in FIG. 21A.

FIG. 29A-B illustrate perspective views of the distal wedge member 208 of the implant 200. As similarly discussed above with respect to the proximal wedge member 206, the guide members 232, 272 and a central aperture 302 of the proximal wedge member 206 are illustrated. The central aperture 302 can be configured to receive an actuator shaft therethrough. When actuator shaft 210 is used in an embodiment, the central aperture 302 can be threaded to correspond to the threads 294 of the actuator shaft 210. In other embodiments, the actuator shaft can engage other portions of the wedge member 208 for causing expansion or contraction thereof.

Figure 30:
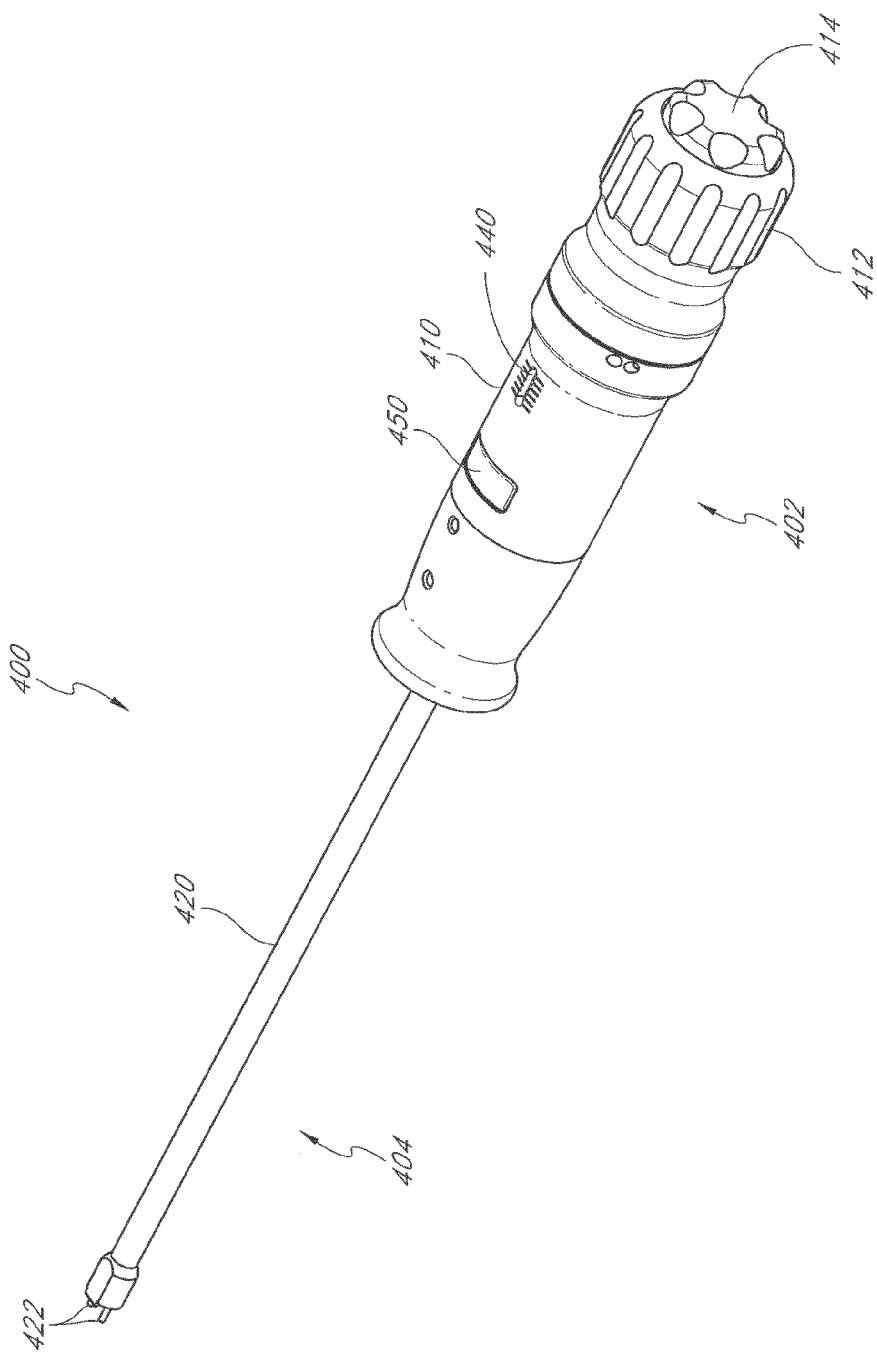
FIG. 30 is a perspective view of a deployment tool according to an embodiment.

Referring now to FIG. 30, there is illustrated a perspective view of a deployment tool 400 according to another embodiment. The tool 400 can comprise a handle section 402 and a distal engagement section 404. The handle portion 402 can be configured to be held by a user and can comprise various features to facilitate implantation and deployment of the implant.

According to an embodiment, the handle section 402 can comprise a fixed portion 410, and one or more rotatable portions, such as the rotatable deployment portion 412 and the rotatable tethering portion 414. In such an embodiment, the tethering portion 414 can be used to attach the implant to the tool 400 prior to insertion and deployment. The deployment portion 412 can be used to actuate the implant and rotate the actuator shaft thereof for expanding the implant. Then, after the implant is expanded and properly placed, the tethering portion 414 can again be used to untether or decouple the implant from the tool 400.

Further, the distal engagement section 404 can comprise a fixed portion 420, an anti-torque component 422, a tethering rod (element 424 shown in FIG. 31), and a shaft actuator rod (element 426 shown in FIG. 27) to facilitate engagement with and actuation of the implant 200. The anti-torque component 422 can be coupled to the fixed portion 420. As described above with reference to FIGS. 21A-B, in an embodiment, the implant 200 can comprise one or more anti-torque structures 250. The anti-torque component 422 can comprise one or more protrusions that engage the anti-torque structures 250 to prevent movement of the implant 200 when a rotational force is applied to the actuator shaft 210 via the tool 400. As illustrated, the anti-torque component 422 can comprise a pair of pins that extend from a distal end of the tool 400. However, it is contemplated that the implant 200 and tool 400 can be variously configured such that the anti-torque structures 250 and the anti-torque component 422 interconnect to prevent a torque being transferred to the implant 200. The generation of the rotational force will be explained in greater detail below with reference to FIG. 31, which is a side-cross sectional view of the tool 400 illustrating the interrelationship of the components of the handle section 402 and the distal engagement section 404.

Figure 31:
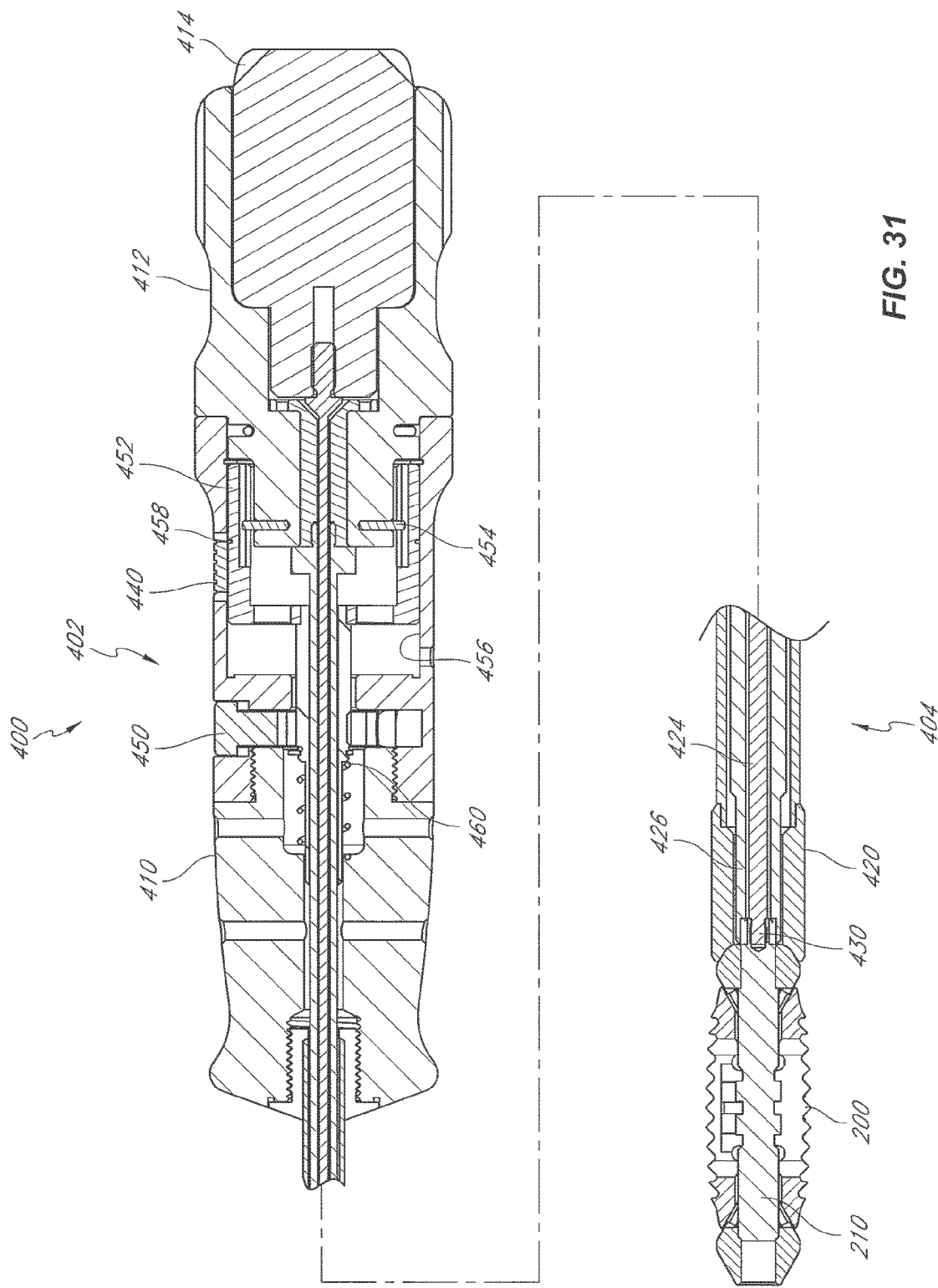
FIG. 31 is a side cross-sectional view of the deployment tool shown in FIG. 30 wherein an expandable implant is attached to a distal end thereof.

For example, as illustrated in FIG. 31, the fixed portion 410 of the handle section 402 can be interconnected with the fixed portion 420 of the distal engagement section 404. The distal engagement section 404 can be configured with the deployment portion 412 being coupled with the shaft actuator rod 426 and the tethering portion 414 being coupled with the tethering rod 424. Although these portions can be coupled to each other respectively, they can move independently of each other and independently of the fixed portions. Thus, while holding the fixed portion 410 of the handle section 402, the deployment portion 412 and the tethering portion 414 can be moved to selectively expand or contract the implant or to attach the implant to the tool, respectively. In the illustrated embodiment, these portions 412, 414 can be rotated to cause rotation of an actuator shaft 210 of an implant 200 engaged with the tool 400.

As shown in FIG. 31, the tether rod 424 can comprise a distal engagement member 430 being configured to engage a proximal end of the actuator shaft 210 of the implant 200 for rotating the actuator shaft 210 to thereby expand the implant from an unexpanded state to and expanded state. The tether rod 424 can be configured with the distal engagement member 430 being a threaded distal section of the rod 424 that can be threadably coupled to an interior threaded portion of the actuator shaft 210.

In some embodiments, the tool 400 can be prepared for a single-use and can be packaged with an implant preloaded onto the tool 400. This arrangement can facilitate the use of the implant and also provide a sterile implant and tool for an operation. Thus, the tool 400 can be disposable after use in deploying the implant.

Referring again to FIG. 30, an embodiment of the tool 400 can also comprise an expansion indicator gauge 440 and a reset button 450. The expansion indicator gauge 440 can be configured to provide a visual indication corresponding to the expansion of the implant 200. For example, the gauge 440 can illustrate an exact height of the implant 200 as it is expanded or the amount of expansion. As shown in FIG. 31, the tool 400 can comprise a centrally disposed slider element 452 that can be in threaded engagement with a thread component 454 coupled to the deployment portion 412.

In an embodiment, the slider element 452 and an internal cavity 456 of the tool can be configured such that the slider element 452 is provided only translational movement in the longitudinal direction of the tool 400. Accordingly, as the deployment portion 412 is rotated, the thread component 454 is also rotated. In such an embodiment, as the thread component 454 rotates and is in engagement with the slider component 452, the slider element 452 can be incrementally moved from an initial position within the cavity 456 in response to the rotation of the deployment portion 412. An indicator 458 can thus be longitudinally moved and viewed to allow the gauge 440 to visually indicate the expansion and/or height of the implant 200. In such an embodiment, the gauge 440 can comprises a transparent window through which the indicator 458 on the slider element 452 can be seen. In the illustrated embodiment, the indicator 458 can be a marking on an exterior surface of the slider element 452.

In embodiments where the tool 400 can be reused, the reset button 450 can be utilized to zero out the gauge 440 to a pre-expansion setting. In such an embodiment, the slider element 452 can be spring-loaded, as shown with the spring 460 in FIG. 31. The reset button 450 can disengage the slider element 452 and the thread component 454 to allow the slider element 452 to be forced back to the initial position.

Additional details and embodiments of an expandable implant can be found in U.S. patent application Ser. No. 2008/0140207, filed Dec. 7, 2007 as U.S. patent application Ser. No. 11/952,900, the entirety of which is hereby incorporated by reference herein.

Bone Rasp

Figure 32:
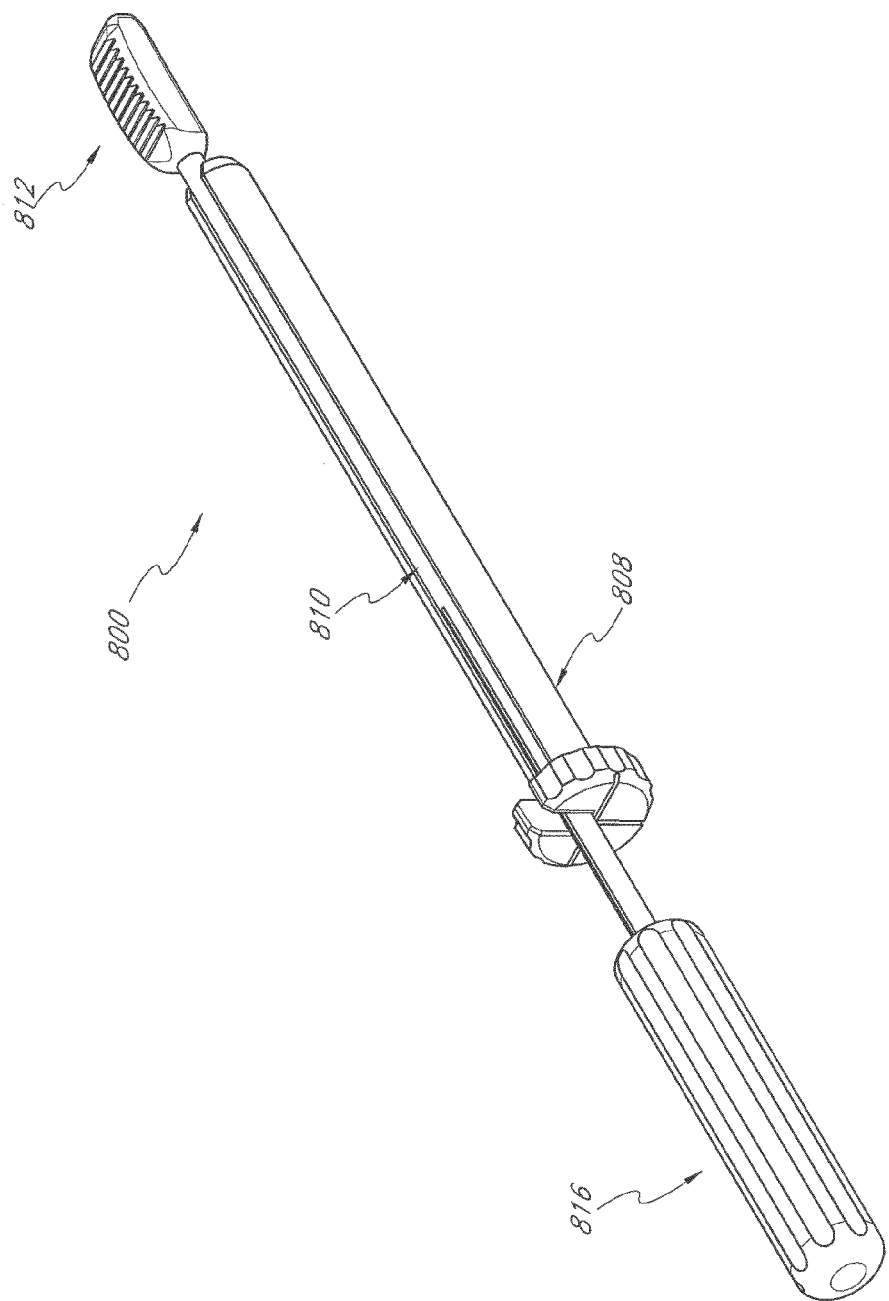
FIG. 32 is a perspective view of a rasp tool, according to an embodiment.

Another example of a surgical tool for use through the access cannula is a bone rasp. One embodiment of such an bone rasp can be found in FIG. 32. As shown in this figure, a rasp tool 800 can be configured to be inserted through the access cannula 30 into the intervertebral disc space. The rasping tool 800 can then be used to abrade or file the inferior surface of the superior vertebrae and/or the superior surface of the inferior vertebrae. The rasping tool 800 may comprise an elongated body 810 and a scraping component 812. A handle 816 may be proximally attached to the elongated body 810. As shown, the rasping tool 800 includes an open sleeve 808 within which the elongate body 810 is slidably received. This configuration may permit the elongated body 810 and scraping component 812 to slide relative to the open sleeve 808.

The entire assembly, including the elongate body 810, open sleeve 808, and scraping component 812 are dimensioned such that the rasping tool 800 can slide longitudinally within the access cannula 30. in use, the rasp tool 800 may be inserted through the access cannula until it reaches the intervertebral disc space. Using the handle 716, a physician may slide the elongate body 810 and scraping component 812 backward and forward, while the open sleeve 808 remains stationary relative to the access cannula 30. In other embodiments, the open sleeve 808 is omitted, and the elongate body 810 is inserted directly into the access cannula 30, and is dimensioned to slidably move within it. In certain embodiments, the elongate body 808 may freely rotate within the open sleeve 808, or within the access cannula 30, in order to permit the physician to rasp a surface at any desired angle. In other embodiments, the orientation of the elongate body 808 may be fixed, such that rasping is only permitted along a predetermined angle relative to the access cannula.

In certain embodiments, the rasping tool may be expandable. For example, a rasp tool 800 can be configured to define an unexpanded configuration. When the tool 800 is initially inserted into the working sleeve, the tool 800 can be positioned in the unexpanded configuration. After the tool 800 is advanced into the intervertebral disc, the tool 800 can be expanded to the expanded configuration.

The tool 800 can comprise an elongated body 810 and one or more scraping components 812. The scraping components 812 can each comprise an outer surface that is configured to scrape or create friction against the disc. For example, the outer surfaces can be generally arcuate and provide an abrasive force when in contact with the interior portion of the disc. In particular, it is contemplated that once the tool 800 is expanded, the scraping components 812 can rasp or scrape against the vertebral end plates of the disc from within an interior cavity formed in the disc. In this manner, the tool 800 can prepare the surfaces of the interior of the disc by removing any additional gelatinous nucleus material, as well as smoothing out the general contours of the interior surfaces of the disc. The rasping may thereby prepare the vertebral endplates for fit with the implant as well as to promote bony fusion between the vertebrae and the implant. Due to the preparation of the interior surfaces of the disc, the placement and deployment of the implant will tend to be more effective.

It is contemplated that the tool 800 can comprise an expansion mechanism that allows the scraping components 812 to move from the unexpanded to the expanded configuration. For example, the tool 800 can be configured such that the scraping components 812 expand from an outer dimension or height of approximately 9 mm to approximately 13 mm. In this regard, the expansion mechanism can be configured similarly to the expansion mechanisms of the implants disclosed herein, the disclosure for which is incorporated here and will not be repeated.

Further, it is contemplated that the scraping components 812 can comprise one or more surface structures, such as spikes, blades, apertures, etc. that allow the scraping components 812 to not only provide an abrasive force, but that also allowed the scraping components 812 to remove material from the disc. In this regard, as in any of the implementations of the method, a cleaning tool can be used to remove loosened, scraped, or dislodged disc material. Accordingly, in various embodiments of the methods disclosed herein, and embodiment of the tool 800 can be used to prepare the implant site (the interior cavity of the disc) to optimize the engagement of the implant with the surfaces of the interior of the disc (the vertebral end plates).

After the implant site has been prepared, the implant can be advanced through the second working sleeve into the disc cavity. Once positioned, the implant can be expanded to its expanded configuration. For example, the implant can be expanded from approximately 9 mm to approximately 12.5 mm. The surgeon can adjust the height and position of the implant as required. Additionally, other materials or implants can then be installed prior to the removal of the second working sleeve and closure of the implant site.

Graft Delivery Device

With reference now to FIGS. 33A to 34D, a bone graft delivery device is disclosed which may be inserted through the access cannula for use in the intervertebral space. For example, the bone graft material can be inserted into the intervertebral disc space in order to promote rapid fixation between the adjacent vertebrae. The bone graft material may be inserted before insertion of an intervertebral implant. Alternatively, the bone graft material may be inserted following insertion of the intervertebral implant. In some implementations, bone graft material is delivered both prior to and following insertion of the intervertebral implant. Bone graft material may be autologous, allograft, xenograft, or synthetic. In addition to bone graft material, other materials may be introduced to the treatment site, as desired. For example, bone morphogenetic proteins may be introduced with a carrier medium, such as a collagen, through use of the disclosed delivery device.

Figure 33A:
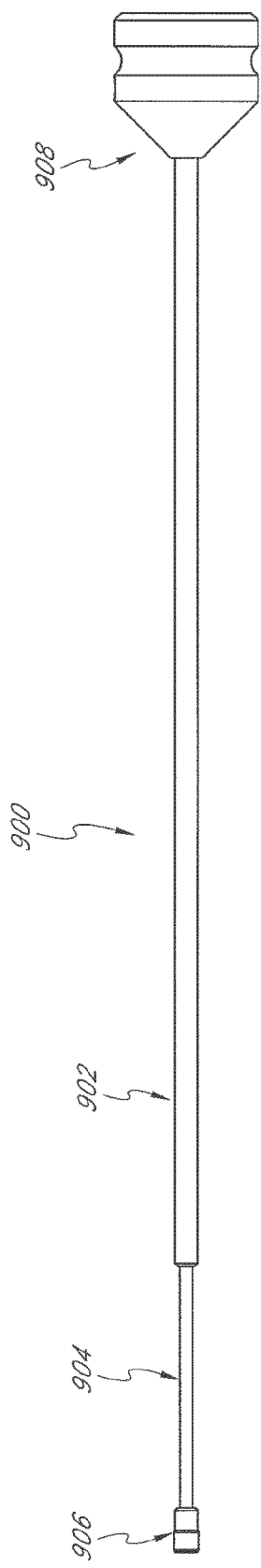
FIG. 33A is a plan view of a plunger assembly for a graft delivery system, according to an embodiment.
Figure 33B:
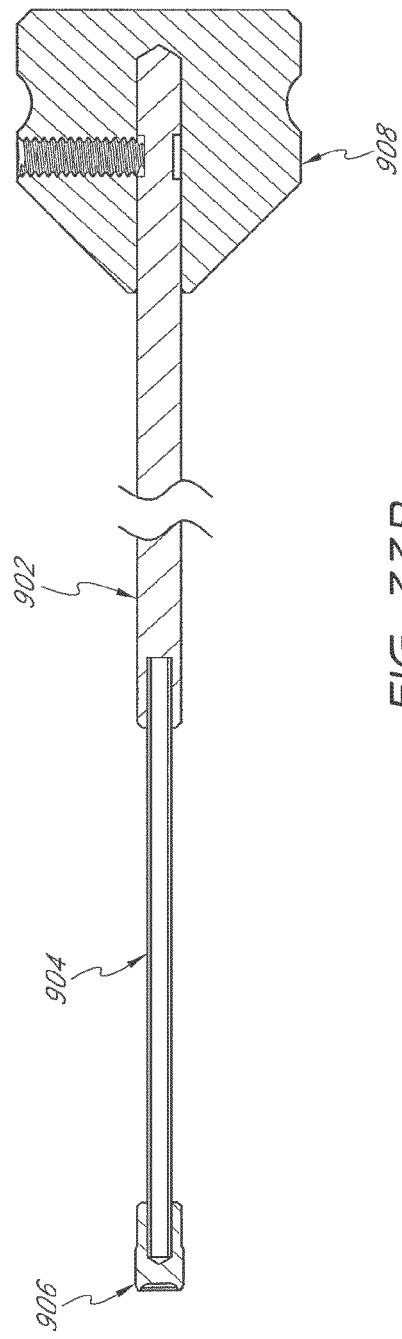
FIG. 33B is a longitudinal cross-sectional view of the plunger assembly shown in FIG. 33A.
Figure 34A:
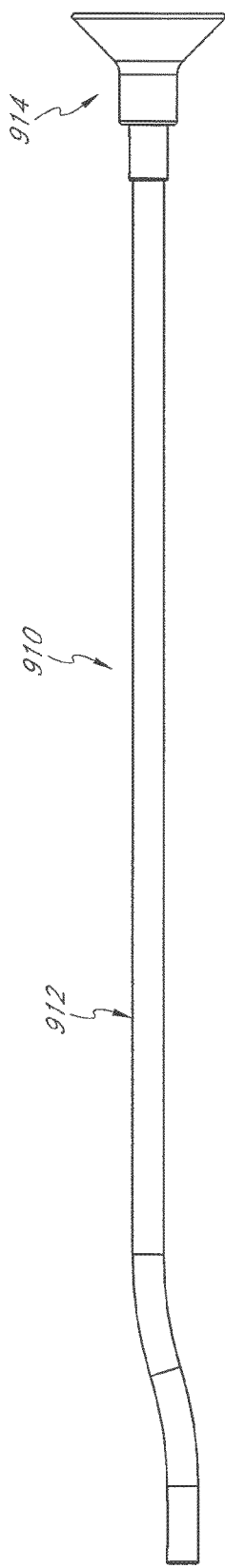
FIG. 34A is a plan view of a funnel assembly for a graft delivery system, according to an embodiment.
Figure 34B:
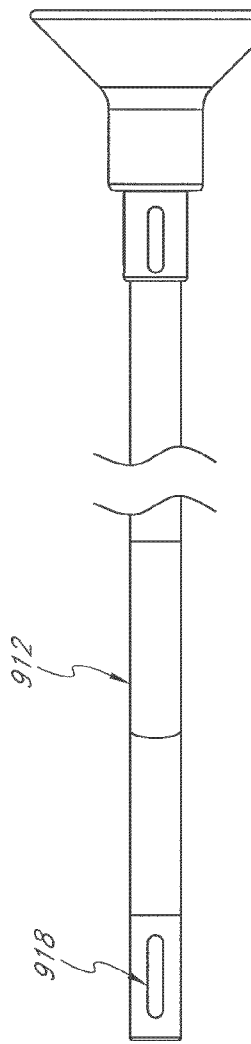
FIG. 34B is a schematic view of the funnel assembly shown in FIG. 34A.
Figure 34D:
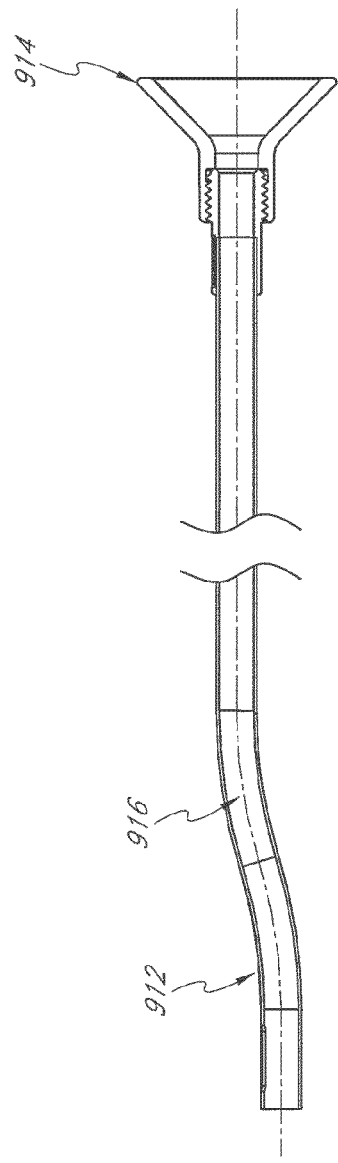
FIG. 34D is a longitudinal cross-sectional view of the funnel assembly shown in FIG. 34A.
Figure 34C:
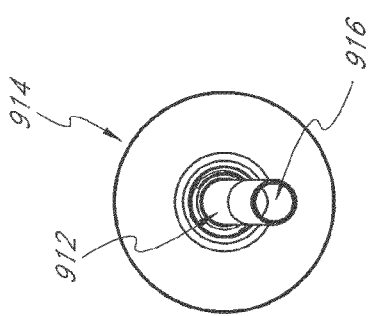
FIG. 34C is an end view of the funnel assembly shown in FIG. 34A.

FIGS. 33A and 33B show a plunger assembly 900. The plunger assembly 900 includes an elongate shaft 902. In some embodiments, the shaft 902 is substantially rigid. The plunger assembly 900 includes a distal tip 906, which is connected to the elongate shaft 902 by a flexible member 904. A plunger knob 908 is positioned at the proximal end of the plunger assembly 900.

FIGS. 34A-D show a funnel assembly 910. The funnel assembly 910 includes a bent shaft 912. The bent shaft 912 may be substantially straight along the majority of its length, with a bend positioned nearer the distal portion of the bent shaft 912. In other embodiments, a plurality of bends may be included in the bent shaft 912. The particular orientation of the bend may be adjusted to provide for improved access to the intervertebral disc space when the funnel assembly is inserted through the access cannula. A receptacle 914 is located at the proximal end of the funnel assembly 910.

The bent shaft 912 includes a central lumen 916 which runs from the opening of the receptacle at the proximal end to the distal opening of the funnel assembly 910. The plunger assembly 900 is configured to be slidably received within the funnel assembly 910. Accordingly, the dimensions of the distal tip 906, flexible member 904 and the elongate shaft 902 are such that they may slide into the opening at the receptacle 914 of the funnel assembly 910. As the plunger assembly 900 is advanced through the lumen 916 of the funnel assembly 910, the distal tip 906 may reach the bent portion of the bent shaft 912. Due to the pliable nature of flexible member 904, the distal tip 906 may be advanced along lumen 916 through the curve in bent shaft 912. The plunger knob 908 may be configured to be mated with the receptacle 914, such that when the plunger assembly 900 is fully advanced into the funnel assembly 910, the plunger knob 908 contacts the receptacle 914. As shown, the receptacle 914 has a hollow conical shape, with the plunger knob 908 having a corresponding conical surface. The shapes of both the receptacle 914 and plunger knob 908 may be varied, and need not be limited to conical shapes, nor even to corresponding shapes. Slot 918 is an opening on the outer surface of bent shaft 912, and may be positioned near the distal end of the funnel assembly 910. The slot 918 may provide for an additional aperture through which bone graft material may flow during injection to the treatment site, as described in more detail below.

In use, bone graft material is introduced into the lumen 916 of the funnel assembly 910. The bone graft material may either be introduced through the receptacle 914 at the proximal end, or it may be back-filled by inserting the bone graft material through the opening in the distal end of the funnel assembly 910. Upon insertion of the plunger assembly 900 into the funnel assembly 910, the distal tip 906 pushes the bone graft material along the length of the bent shaft 912 and eventually out of the funnel assembly 910.

It should also be noted that bone chips and/or autograft must be made into pieces small enough to flow through the funnel assembly 910. Otherwise, the funnel assembly 910 may become congested and the bone graft may not flow into the target site as desired.

Once the bone graft material is loaded into the funnel assembly, the bone graft material can be deployed at the target site. The funnel assembly can be inserted into the access cannula until the distal tip of the funnel assembly is positioned adjacent to the target site. The location of the distal tip of the funnel instrument can be modified to any desired location for deploying the graft material at the target site. Due to the bend in the funnel assembly 910, the device may be rotated within the access cannula in order to achieve different angles of approach. The bend may therefore provide for improved access to different regions of the intervertebral disc space. Then, inserting the plunger assembly 900 through the funnel assembly 910, a desired amount of graft material can be injected at the target site. In certain embodiments, the funnel assembly 910 and plunger assembly 900 can each be placed over a k-wire. The plunger assembly 900 can then be advanced into the funnel assembly 910 to deploy the graft into the disc.

As the bone graft material flows through the lumen 916 of funnel assembly 910, it passes slot 918 near the distal end of the bent tube 912. In some embodiments, the opening of slot 918 is smaller than the opening of lumen 916, such that, absent backpressure, bone graft material preferentially exits the funnel assembly 910 through the distal opening of lumen 916. As the target site is filled with bone graft material, however, it may become increasingly difficult to advance the plunger assembly 900 and introduce new bone graft material through the lumen 916. In the event that such resistance is present, some of the bone graft material may be forced through slot 918, thereby providing an alternate distribution route for the bone graft material. In certain embodiments, a plurality of slots 918 may be provided around the circumference of bent shaft 912. The position of slot 918 may be varied depending on the desired distribution of bone graft material at the treatment site. As discussed above, the funnel assembly 910 may be rotated within the access cannula, allowing for bone graft material exiting the slot 918 to be deposited in various locations at the treatment site.

Once the implant and, if applicable, bone graft material have been inserted into the intervertebral disc space, supplemental internal spinal fixation can be employed to facilitate fusion. For example, spinal fixation can include facet screw fixation systems, facet compression devices, and/or posterior pedicle screw and rod systems.

Although the embodiments shown herein depict a dilation introducer with three dilator tubes and one access cannula, other variations are possible. For instance, as noted above, a dilation introducer may include only two dilator tubes and an access cannula. In another embodiment, a dilation introducer may include four or more dilator tubes and an access cannula. In a modified arrangement, the access cannula would be replaced by a dilator tube, wherein the dilator tube with cutting flutes would remain in place, with the inner dilator tubes removed to provide access for surgical tools. The skilled artisan will readily ascertain that many variations of this sort are possible without departing from the scope of the present invention.

The specific dimensions of any of the embodiment disclosed herein can be readily varied depending upon the intended application, as will be apparent to those of skill in the art in view of the disclosure herein. Moreover, although the present inventions have been described in terms of certain preferred embodiments, other embodiments of the inventions including variations in the number of parts, dimensions, configuration and materials will be apparent to those of skill in the art in view of the disclosure herein. In addition, all features discussed in connection with any one embodiment herein can be readily adapted for use in other embodiments herein to form various combinations and subcombinations. The use of different terms or reference numerals for similar features in different embodiments does not imply differences other than those which may be expressly set forth. Accordingly, the present inventions are intended to be described solely by reference to the appended claims, and not limited to the preferred embodiments disclosed herein.

What is claimed is:

1. A method of performing an endoscopic procedure in an intervertebral disc space through a Kambin's triangle of a human, the method comprising the steps of:
    inserting a guide member through tissue of the human toward the intervertebral disc space along a generally transforaminal approach along a trajectory;
    applying an electrical current to the guide member during the inserting step; and
    during the applying step, determining that the guide member is approaching a nerve as the guide member is inserted through the tissue of the human during the inserting step;
    changing the trajectory to a changed trajectory, and driving the tube through tissue of the human toward the intervertebral disc space along the changed trajectory along the generally transforaminal approach toward the Kambin's triangle;
    introducing at least one dilator tube over the guide member;
    introducing an access cannula over the at least one dilator tube;
    removing the guide member and the at least one dilator tube; and
    performing the endoscopic procedure in the intervertebral disc space through the access cannula and through the Kambin's triangle.

2. The method claim 1, wherein the determining step comprises determining that a nerve of the Kambin's triangle has been stimulated by the electrical current when the electrically conductive instrument approaches the nerve.

3. The method of claim 2, wherein the determining step comprises the step of visually observing a visual indication that the guide member is approaching the nerve.

4. The method of claim 3, wherein the changing step removes the visual indication.

5. The method of claim 4, wherein the visual indication comprises a movement of a leg of the human.

6. The method of claim 1, wherein the driving step comprises driving the tube along a changed trajectory that extends through the Kambin's triangle.

7. The method of claim 6, wherein the step of performing the foraminoplasty comprises rotating a bone cutting instrument so as to remove bone.

8. The method of claim 1, comprising the step of performing a foraminoplasty under endoscopic visualization prior to the step of performing the endoscopic procedure.

9. The method of claim 8, wherein the step of rotating the bone cutting instrument comprises rotating the bone cutting instrument about an axis that extends along the changed trajectory.

10. The method of claim 9, wherein the endoscopic procedure comprises removing disc material from the intervertebral disc space.

11. The method of claim 1, wherein the at least one dilator tube comprises a plurality of dilator tubes, and the step of introducing the access cannula comprises introducing the access cannula over a largest one of the plurality of dilator tubes.

12. The method of claim 1, wherein the endoscopic procedure comprises inserting an intervertebral implant through the access cannula and into the intervertebral disc space, and subsequently expanding the intervertebral implant from a first height to a second height greater than the first height.

13. The method of claim 1, wherein the applying step comprises applying a constant current to the guide member.

14. The method of claim 1, wherein the applying step comprises varying an amount of the current to the guide member.

15. The method of claim 1, further comprising the step of attaching a pedicle screw to a pedicle of a vertebra.

* * * * *